(12) United States Patent
Obrecht et al.

(10) Patent No.: US 8,633,163 B2
(45) Date of Patent: Jan. 21, 2014

(54) TEMPLATE-FIXED PEPTIDOMIMETICS

(75) Inventors: Daniel Obrecht, Baettwil (CH); Frank Gombert, Binningen (CH); Steve J. Demarco, Dietgen (CH); Christian Ludin, Oberwil (CH); Alexander Lederer, Basel (CH); Christian Bisang, Basel (CH); Odile Sellier-Kessler, Baldersheim (FR); Francoise Jung, Huningue (FR); Reshmi Mukherjee, Pasadena, CA (US); Heiko Henze, Zurich (CH); Barbara Romagnoli, Binningen (CH)

(73) Assignee: POLYPHOR Ltd., Allschwil (CH)

( * ) Notice: Subject to any disclaimer, the term of this patent is extended or adjusted under 35 U.S.C. 154(b) by 946 days.

(21) Appl. No.: 12/524,862

(22) PCT Filed: Jan. 29, 2007

(86) PCT No.: PCT/CH2007/000038
§ 371 (c)(1),
(2), (4) Date: Dec. 3, 2009

(87) PCT Pub. No.: WO2008/092281
PCT Pub. Date: Aug. 7, 2008

(65) Prior Publication Data
US 2010/0093644 A1 Apr. 15, 2010

(51) Int. Cl.
| | |
|---|---|
| A61K 38/00 | (2006.01) |
| C07K 14/72 | (2006.01) |
| C07K 14/705 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl.
USPC ..................................... 514/20.6; 530/330

(58) Field of Classification Search
None
See application file for complete search history.

(56) References Cited

U.S. PATENT DOCUMENTS

| | | | |
|---|---|---|---|
| 5,811,548 A * | 9/1998 | Bannwarth et al. | ............. 544/32 |
| 6,878,804 B1 | 4/2005 | Robinson et al. | |
| 7,091,313 B2 | 8/2006 | Robinson et al. | |
| 7,253,146 B2 | 8/2007 | Obrecht et al. | |
| 7,417,024 B2 | 8/2008 | Obrecht et al. | |
| 7,582,604 B2 | 9/2009 | Vrijbloed et al. | |
| 2005/0181454 A1 | 8/2005 | Robinson et al. | |
| 2006/0234923 A1 | 10/2006 | Zumbrunn et al. | |
| 2007/0054840 A1 | 3/2007 | Vrijbloed et al. | |
| 2007/0078079 A1 | 4/2007 | Zumbrunn et al. | |
| 2009/0054345 A1 | 2/2009 | DeMarco et al. | |
| 2009/0118134 A1 | 5/2009 | Vrijbloed et al. | |

FOREIGN PATENT DOCUMENTS

| | | |
|---|---|---|
| WO | 01 16161 | 3/2001 |
| WO | 2004 096838 | 11/2004 |

\* cited by examiner

*Primary Examiner* — Cecilia J Tsang
*Assistant Examiner* — Zachary J Miknis
(74) *Attorney, Agent, or Firm* — Oblon, Spivak, McClelland, Maier & Neustadt, L.L.P.

(57) ABSTRACT

Template-fixed β-hairpin peptidomimetics of the general formula (I) wherein Z is a template-fixed chain of 4 α-amino acid residues which, depending on their positions in the chain (counted starting from the N-terminal amino acid) are Gly, or of certain types which, as the remaining symbols in the above formula, are defined in the description and the claims, and salts thereof, have the property to agonize or to antagonize GPCR receptors such as CXCR3, urotensin and CCR10. They can be used as medicaments to treat or prevent diseases such as cardiovascular disorders, dermatological disorders, endocrine system and hormone disorders, metabolic diseases, inflammatory diseases, neurological diseases, respiratory diseases, haematological diseases and cancer. These β-hairpin peptidomimetics can be manufactured by a process which is based on a mixed solid- and solution phase synthetic strategy.

(I)

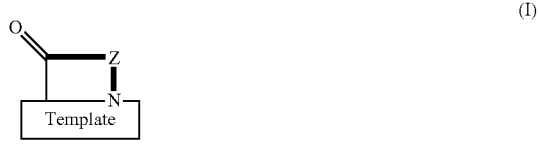

12 Claims, No Drawings

TEMPLATE-FIXED PEPTIDOMIMETICS

The present invention provides template-fixed β-hairpin peptidomimetics incorporating a template-fixed chain of 4 α-amino acid residues which, depending on their positions in the chain, are Gly or Pro or of certain types, as defined herein below. These template-fixed β-hairpin mimetics have an agonizing or antagonizing activity against G-protein-coupled receptors (GPCR's), particularly the urotensin, CXCR3 and the CCR10 receptor and show high selectivity against certain GPCR receptors. In addition, the present invention provides an efficient synthetic process by which these compounds can, if desired, be made in parallel library-format.

Many medically significant biological processes are mediated by signal transduction that involves GPCR's. The family of GPCRs include receptors for hormones, neurotransmitters growth factors and viruses (Th. Klabunde, G. Hessler, *ChemBioChem* 2002, 3, 928-44). Whereas for an additional 230 receptors the natural ligand is known, another 160, so-called orphan receptors, have been identified within the human genome, for which the (patho)physiological function is unknown (A. Wise, K. Gearing, S. Rees, *Drug Discovery Today*, 2002, 7, 235-46).

The GPCR's can be grouped into three major families: family A (rhodopsin-like or adrenergic-like family), family B (glucagon-receptor-like or secretin-receptor-like family), and family C (metabotropic glutamate receptors). Within each receptor family a certain sequence pattern (so-called fingerprint) and several structural features beyond the generally shared membrane topology are conserved (T. K. Attwood, *Trends Pharmacol. Sci* 2001, 22, 165-65). Family A is by far the largest class. GPCR's are membrane-bound, and characterized by a conserved seven helix transmembrane-spanning domain. Recently, the 3D structure of bovine rhodopsin by X-ray crystallography was reported (K. Palczewsky et al. *Science* 2000, 289, 739-45) as the first GPCR structure at atomic resolution. Based on this structure several models for other GPCR's have been reported using homology modeling (M. C. Gershengorn et al. *Endocrinology* 2001, 142, 2-10; S. Shacham et al. *Med. Res. Rev.* 2001, 21, 472-83).

Although over the past 15 years, nearly 350 therapeutic agents targeting GPCR receptors have been successfully introduced into the market (Th. Klabunde, G. Hessler, *ChemBioChem* 2002, 3, 928-44; G. Vauquelin et al. *Fundam. Clin. Pharmacol.* 2005, 19, 45-56), several toxicological problems which arose from mainly lack of selectivity of some of those drugs, need to be further investigated. Clearly there is a need for new selective compounds for treating or preventing diseases including, but not limited to, infections, cancers, allergies, cardiovascular and peripheral and central nervous system disorder.

The present invention describes a novel general approach to discover potent, selective and drugable ligands having agonizing or antagonizing activity against GPCR receptors. Within the scope of the present invention, this approach is particularly suited to discover ligands for peptidergic and protein-liganded GPCR's. Some of the peptidergic GPCR ligands/receptors that are of therapeutic relevance are:

Somatostatins (A. V. Schally et al. *Cell. Mol. Life. Sci.* 2004, 61, 1042-68), neurokinins, neurotensins (W. Rostene et al. *Encyclop. Biol. Chem.* 2004, 3, 3236; M. Boules et al. *Expert. Opin. Investig. Drugs* 2005, 14, 359-69; P. Kitabgi, *Curr. Opin. Drug Disc. Devel.* 2002, 5, 764-76), bradykinins (F. Marceau et al. *Nat. Rev. Drug Disc.* 2004, 3, 845-52), vasopressins (M. Ashton et al. *Comb. Chem. And High Throughput Screening* 2004, 7, 441-53), tachykinins, bombesins (E. R. Spindel et al. *Recent Progress in Hormone Research* 1993, 48, 365-91; R. T. Jensen et al. *Growth Factors, Peptides, and Receptors*, p. 225-237, Ed. By T. W. Moody, Plenum Press, New York, 1993; A. V. Schally et al. *Cell. Mol. Life. Sci.* 2004, 61, 1042-68), endothelins (G. Ertl et al. *Drugs* 2004, 64, 1029-40), urotensin II (F. D. Russell, *Pharmacol. Ther.* 2004, 103, 223-43), GH-RH (A. V. Schally et al. *Cell. Mol. Life. Sci.* 2004, 61, 1042-68), ghrelin (A. V. Schally et al. *Cell. Mol. Life. Sci.* 2004, 61, 1042-68; E. Ghio et al. *Clin. Endocrinol.* 2005, 62, 1-17), melanocortins (B. G. Irani et al. *Curr. Pharm. Des.* 2004, 10, 3443-79), glucagon-like peptide 1 (GLP-1, C. J. Small et al. *Curr. Drug Targets CNS Neurol. Disord.* 2004, 3, 379-88), peptide YY (PYY, C. J. Small et al. *Curr. Drug Targets CNS Neurol. Disord.* 2004, 3, 379-88), VIP (A. V. Schally et al. *Cell. Mol. Life. Sci.* 2004, 61, 1042-68), and protease-activated receptors 1 and 2 (PAR-1 and 2, H. G. Selnick et al. *Curr. Med. Chem. Cardiovasc. Hematol. Agents* 2003, 1, 47-59; V. S. Ossovskaya et al. *Physiol. Rev.* 2004, 84, 579-621; A. M. Coelho et al. *Curr. Med. Chem. Cardiovasc. Hematol. Agents* 2003, 1, 61-72; M. Steinhoff et al. *Endocrin. Rev.* 2005, 26, 1-43).

Among the proteinogenic GPCR ligands the therapeutically important family of roughly 60 chemokines (L. Bendall, *Histol. Histopathol.* 2005, 20, 907-26; Moser et al.) can be mentioned (e.g. CXCL-1, CXCL-2, CXCL-5, CXCL-8, CXCL-12).

In the compounds described below, a new strategy is introduced to stabilize β-hairpin conformations in backbone-cyclic β peptide mimetics exhibiting selective agonizing or antagonizing activity against G-protein-coupled receptors (GPCR's), particularly the urotensin, CXCR3 and the CCR10 receptor. This involves transplanting key hairpin sequence onto a template, whose function is to restrain the peptide loop backbone into a hairpin geometry.

Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441), but such molecules have not previously been evaluated or disclosed for development of antagonizing or agonizing activity against G-protein-coupled receptors (GPCR's), particularly the urotensin, CXCR3 and the CCR10 receptor. However, the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). These methods allow the synthesis and screening of large hairpin mimetic libraries, which in turn considerably facilitates structure-activity studies, and hence the discovery of new molecules with potent selective agonizing or antagonizing activity.

β-Hairpin peptidomimetics obtained by the approach described here are useful as anticancer agents or anti inflammatory agents or for treating or preventing cardiovascular and peripheral and central nervous system disorder.

The β-hairpin peptidomimetics of the present invention are compounds of the general formula

wherein
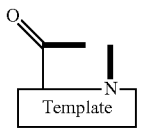
is a group of one of the formulae
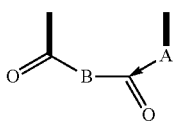
(a1)
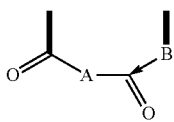
(a2)
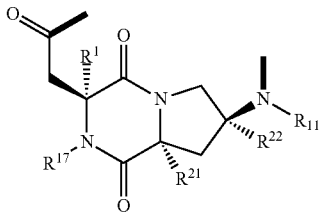
(b1)
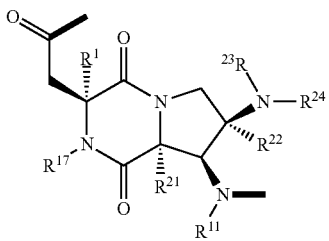
(b2)
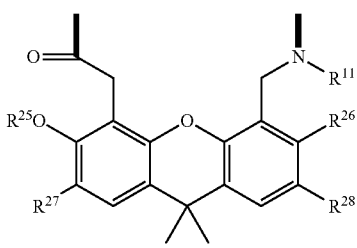
c1)
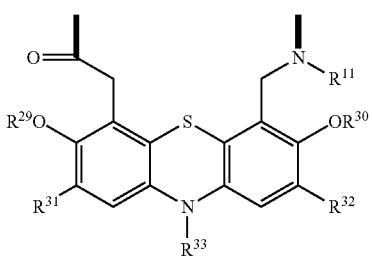
(c2)
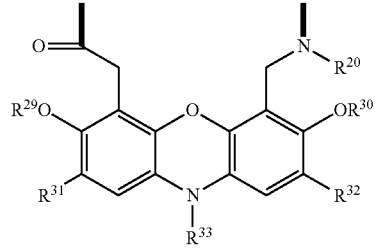
(c3)
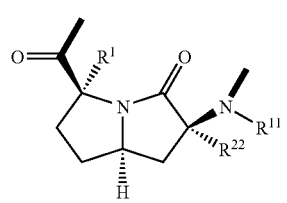
(d1)
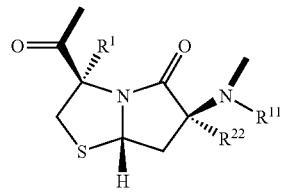
(d2)
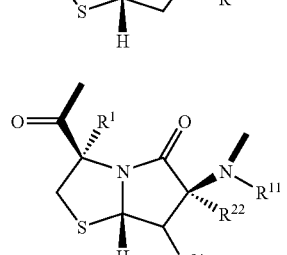
(d3)
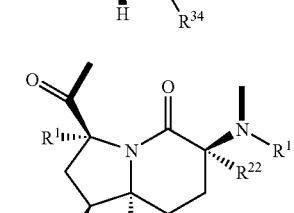
(e1)
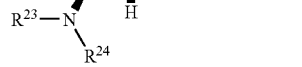
(e2)
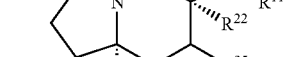
(e3)

-continued
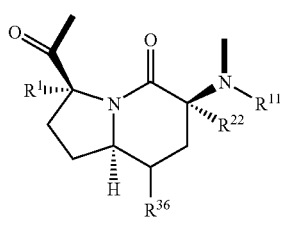
(e4)
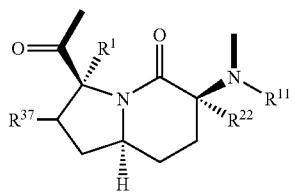
(e5)
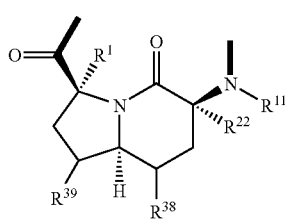
(e6)
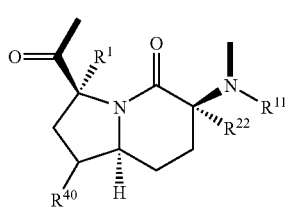
(e7)
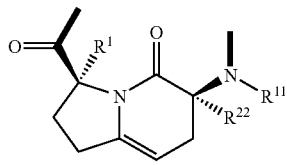
(e8)
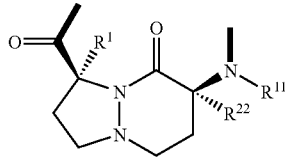
(e9)
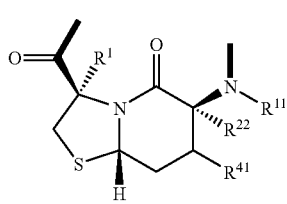
(e10)
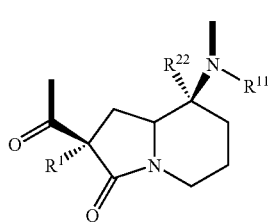
(e11)
-continued
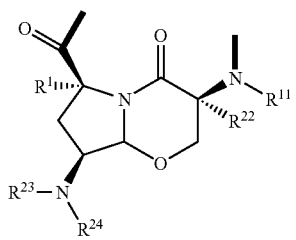
(e12)
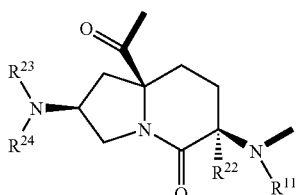
(e13)
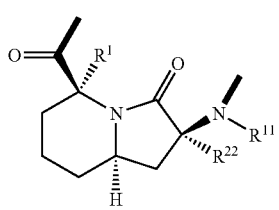
(f)
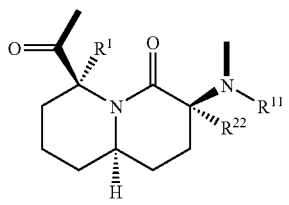
(g1)
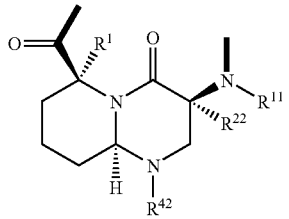
(g2)
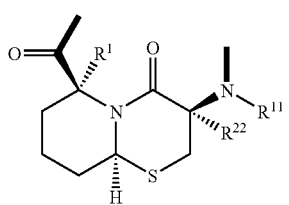
(g3)
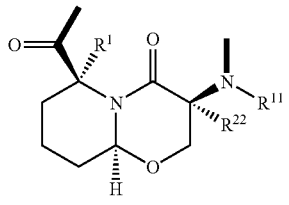
(g4)

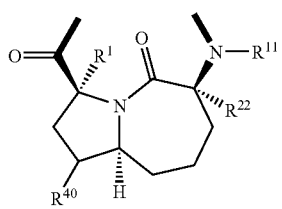 (h1)
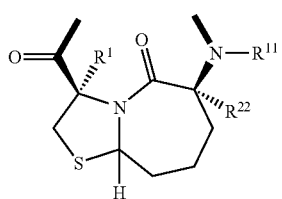 (h2)
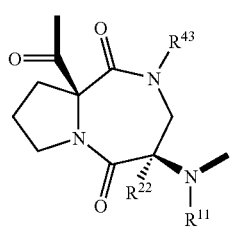 (h3)
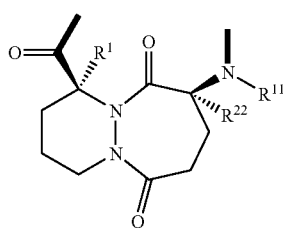 (i)
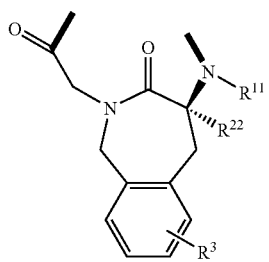 (k)
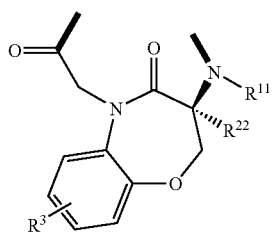 (l1)
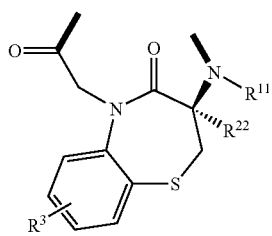 (l2)
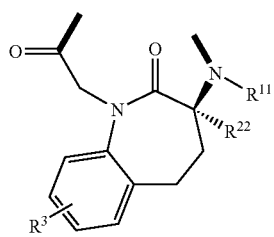 (l3)
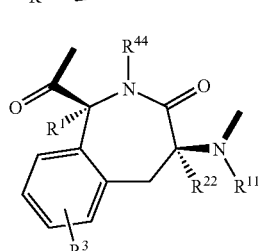 (l4)
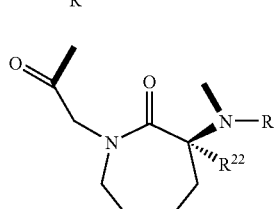 (m)
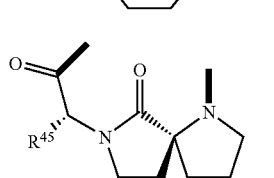 (n)
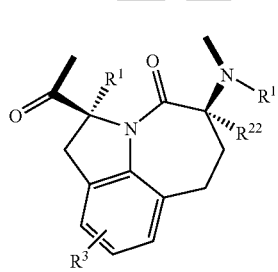 (o)
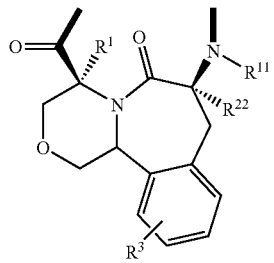 (p1)
(p2)

-continued
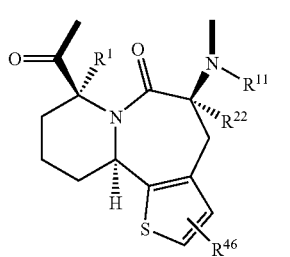
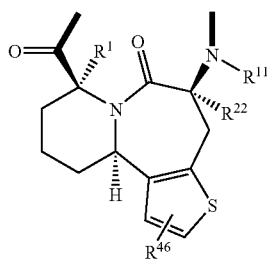
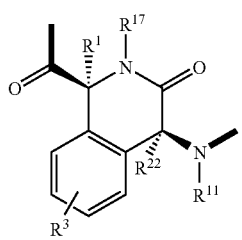
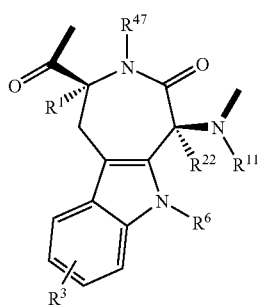
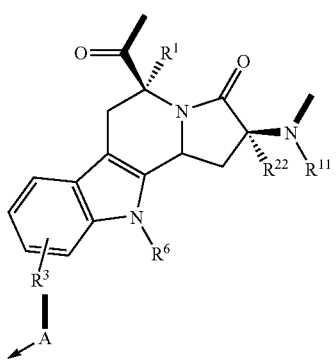
A is a group of one of the formulae
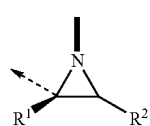
A1
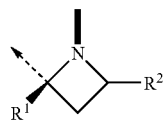 (p3)
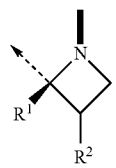 (p4)
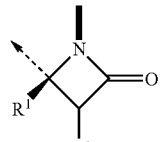 (q)
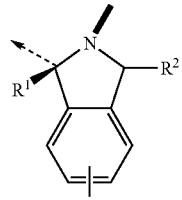 (r)
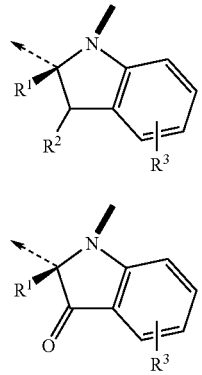 (s)
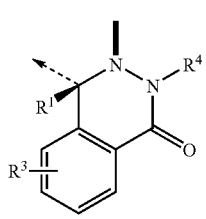
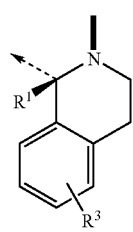
A2
A3
A4
A5
A6
A7
A8
A9

A10 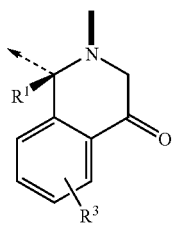
A11 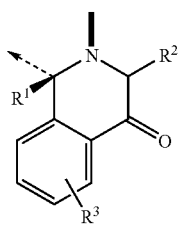
A12 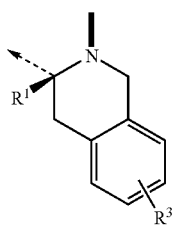
A13 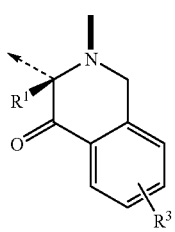
A14 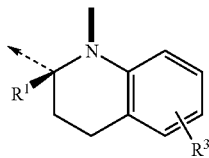
A15 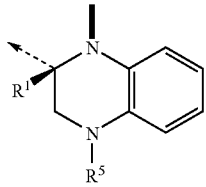
A16 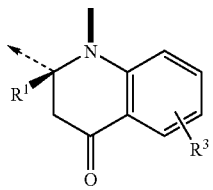
A17 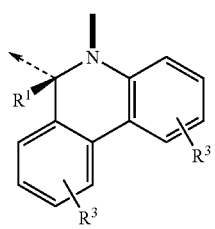
A18 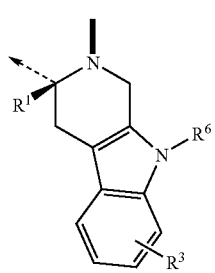
A19 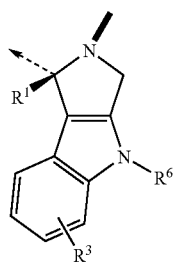
A20 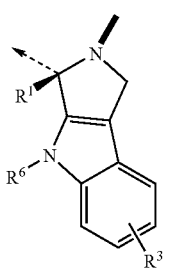
A21 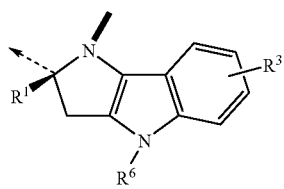
A22 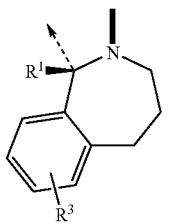

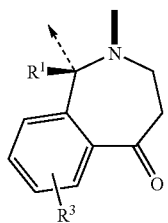 A23
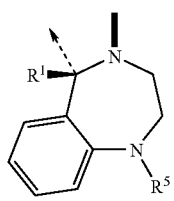 A24
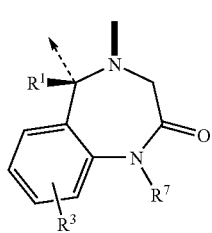 A25
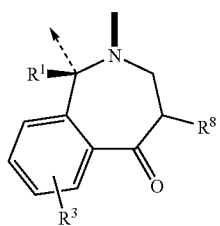 A26
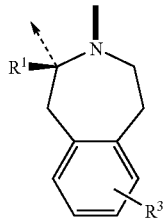 A27
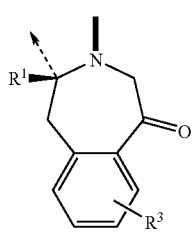 A28
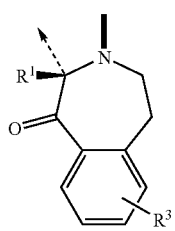 A29
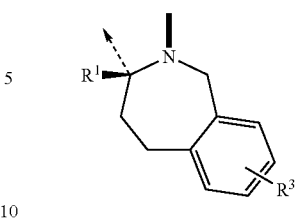 A30
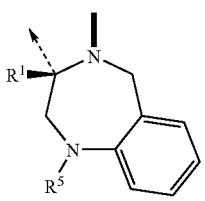 A31
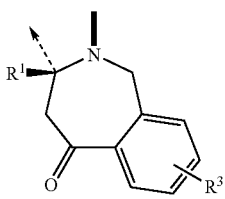 A32
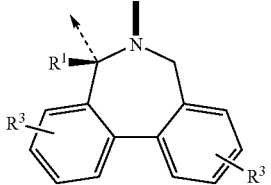 A33
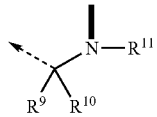 A34
A35
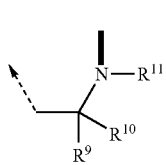 A36
A37
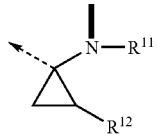 A38

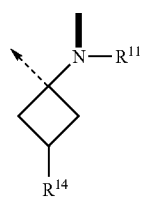 A39
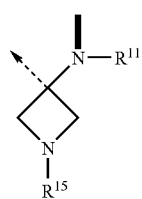 A40
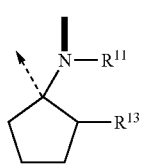 A41
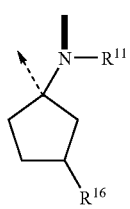 A42
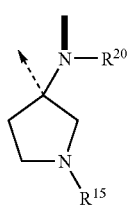 A43
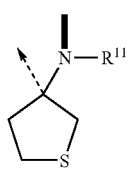 A44
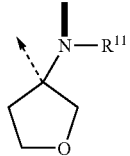 A45
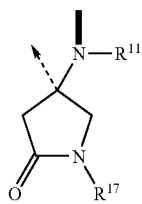 A46
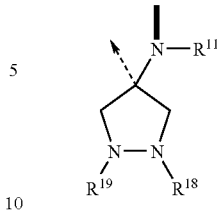 A47
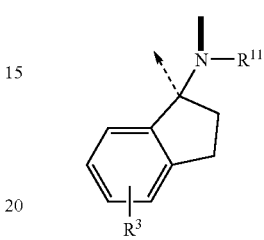 A48
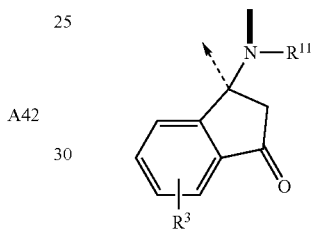 A49
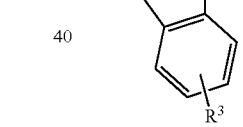 A50
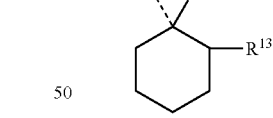 A51
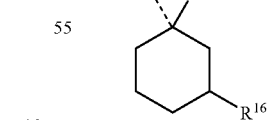 A52
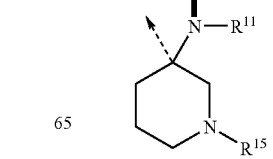 A53

-continued
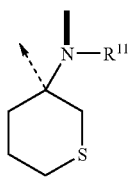
A54
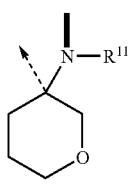
A55
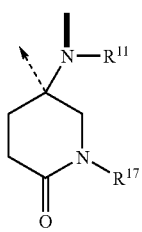
A56
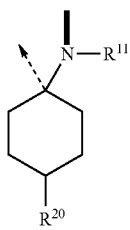
A57
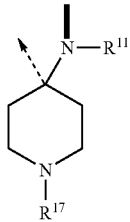
A58
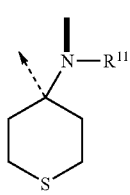
A59
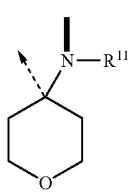
A60
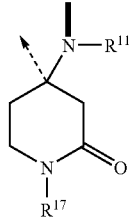
A61
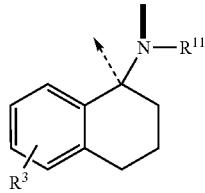
A62
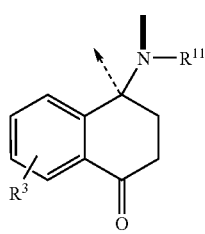
A63
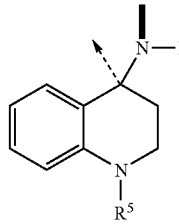
A64
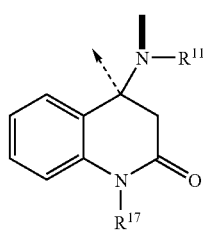
A65
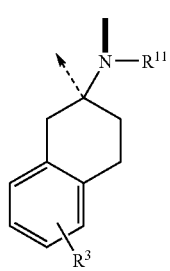
A66
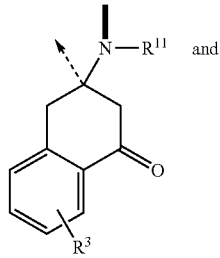 and
A67

-continued

A68

A69

A70

A71

B is the enantiomer of one of the groups A1 to A69 as shown hereinabove, $R^1$ is H; alkyl; alkenyl; —$(CH_2)_p(CHR^{53})_sOR^{47}$; —$(CH_2)_p(CHR^{53})_sSR^{48}$; —$(CH_2)_p(CHR^{53})_sNR^{23}R^{24}$; —$(CH_2)_p(CHR^{53})_sOCONR^{50}R^{67}$; —$(CH_2)_p(CHR^{53})_sNR^{11}CONR^{50}R^{51}$; —$(CH_2)_p(CHR^{53})_sNR^{11}COR^{56}$; —$(CH_2)_o(CHR^{53})_sCOOR^{49}$; —$(CH_2)_o(CHR^{53})_sCONR^{50}R^{51}$; —$(CH_2)_o(CHR^{53})_sPO(OR^{52})_2$; —$(CH_2)_o(CHR^{53})_sSO_2R^{54}$; or —$(CH_2)_o(CHR^{53})_sR^{69}$;

$R^2$ is H; alkyl; alkenyl; —$(CH_2)_p(CHR^{53})_sOR^{47}$; —$(CH_2)_p(CHR^{53})_sSR^{48}$; —$(CH_2)_p(CHR^{53})_sNR^{23}R^{24}$; —$(CH_2)_p(CHR^{53})_sOCONR^{50}R^{67}$; —$(CH_2)_p(CHR^{53})_sNR^{11}CONR^{50}R^{51}$; —$(CH_2)_p(CHR^{53})_sNR^{11}COR^{56}$; —$(CH_2)_o(CHR^{53})_sCOOR^{49}$; —$(CH_2)_o(CHR^{53})_sCONR^{50}R^{51}$; —$(CH_2)_o(CHR^{53})_sPO(OR^{52})_2$; —$(CH_2)_o(CHR^{53})_sSO_2R^{54}$; or —$(CH_2)_o(CHR^{53})_sR^{69}$;

$R^3$ is H; Cl; F; $CF_3$; CN; $NO_2$; lower alkyl; lower alkenyl; aryl; aryl-lower alkyl; —$(CH_2)_o(CHR^{53})_sOR^{47}$; —$(CH_2)_o(CHR^{53})_sSR^{48}$; —$(CH_2)_o(CHR^{53})NR^{23}R^{24}$; —$(CH_2)_o(CHR^{53})_sOCONR^{50}R^{67}$; —$(CH_2)_o(CHR^{53})_sNR^{11}CONR^{50}R^{51}$; —$(CH_2)_o(CHR^{53})_sNR^{11}COR^{56}$; —$(CH_2)_o(CHR^{53})_sCOOR^{49}$; —$(CH_2)_o(CHR^{53})_sCONR^{56}R^{51}$; —$(CH_2)_o(CHR^{53})_sPO(OR^{52})_2$; —$(CH_2)_o(CHR^{53})_sSO_2R^{54}$; —$(CH_2)_o(CHR^{53})_sCOR^{56}$; or —$(CH_2)_o(CHR^{53})_sR^{69}$;

$R^4$ is H; alkyl; alkenyl; —$(CH_2)_m(CHR^{53})_sOR^{47}$; —$(CH_2)_m(CHR^{53})_sSR^{48}$; —$(CH_2)_m(CHR^{53})_sNR^{23}R^{24}$; —$(CH_2)_m(CHR^{53})_sOCONR^{50}R^{67}$; —$(CH_2)_m(CHR^{53})_sNR^{11}CONR^{50}R^{51}$; —$(CH_2)_p(CHR^{53})_sNR^{11}COR^{56}$; —$(CH_2)_p(CHR^{53})_sCOOR^{49}$; —$(CH_2)_p(CHR^{53})_sCONR^{50}R^{51}$; —$(CH_2)_p(CHR^{53})_sPO(OR^{52})_2$; —$(CH_2)_p(CHR^{53})_sSO_2R^{54}$; or —$(CH_2)_o(CHR^{53})_sR^{69}$;

$R^5$ is H; alkyl; alkenyl; —$(CH_2)_m(CHR^{53})_sOR^{47}$; —$(CH_2)_m(CHR^{53})_sNR^{23}R^{24}$; —$(CH_2)_m(CHR^{53})_sOCONR^{50}R^{67}$; —$(CH_2)_m(CHR^{53})_sNR^{11}CONR^{50}R^{51}$; —$(CH_2)_m(CHR^{53})_sNR^{11}COR^{56}$; —$(CH_2)_q(CHR^{53})_sCOOR^{49}$; —$(CH_2)_q(CHR^{53})_sCONR^{50}R^{51}$; —$(CH_2)_q(CHR^{53})_sPO(OR^{52})_2$; —$(CH_2)_q(CHR^{53})_sSO_2R^{54}$; or —$(CH_2)_o(CHR^{53})_sR^{69}$;

$R^6$ is H; alkyl; alkenyl; —$(CH_2)_m(CHR^{53})_sOR^{47}$; —$(CH_2)_m(CHR^{53})_sNR^{23}R^{24}$; —$(CH_2)_m(CHR^{53})_sOCONR^{50}R^{67}$; —$(CH_2)_m(CHR^{53})_sNR^{11}CONR^{50}R^{51}$; —$(CH_2)_m(CHR^{53})_sNR^{11}COR^{56}$; —$(CH_2)_o(CHR^{53})_sCOOR^{49}$; —$(CH_2)_o(CHR^{53})_sCONR^{50}R^{51}$; —$(CH_2)_o(CHR^{53})_sPO(OR^{52})_2$; —$(CH_2)_o(CHR^{53})_sSO_2R^{54}$; or —$(CH_2)_o(CHR^{53})_sR^{69}$;

$R^7$ is H; alkyl; alkenyl; —$(CH_2)_m(CHR^{53})_sOR^{47}$; —$(CH_2)_m(CHR^{53})_sSR^{48}$; —$(CH_2)_m(CHR^{53})_sNR^{23}R^{24}$; —$(CH_2)_m(CHR^{53})_sOCONR^{50}R^{67}$; —$(CH_2)_m(CHR^{53})_sNR^{11}CONR^{50}R^{51}$; —$(CH_2)_m(CHR^{53})_sNR^{11}COR^{56}$; —$(CH_2)_r(CHR^{53})_sCOOR^{49}$; —$(CH_2)_r(CHR^{53})_sCONR^{50}R^{51}$; —$(CH_2)_r(CHR^{53})_sPO(OR^{52})_2$; —$(CH_2)_r(CHR^{53})_sSO_2R^{54}$; or —$(CH_2)_r(CHR^{53})_sR^{69}$;

$R^8$ is H; alkyl; alkenyl; —$(CH_2)_o(CHR^{53})_sOR^{47}$; —$(CH_2)_o(CHR^{53})_sNR^{23}R^{24}$; —$(CH_2)_o(CHR^{53})_sOCONR^{50}R^{67}$; —$(CH_2)_o(CHR^{53})_sNR^{11}CONR^{50}R^{51}$; —$(CH_2)_o(CHR^{53})_sNR^{11}COR^{56}$; —$(CH_2)_o(CHR^{53})_sCOOR^{49}$; —$(CH_2)_o(CHR^{53})_sCONR^{50}R^{51}$; —$(CH_2)_o(CHR^{53})_sPO(OR^{52})_2$; —$(CH_2)_o(CHR^{53})_sSO_2R^{54}$; or —$(CH_2)_o(CHR^{53})_sR^{69}$;

$R^9$ is alkyl; alkenyl; —$(CH_2)_p(CHR^{53})_sOR^{47}$; —$(CH_2)_p(CHR^{53})_sSR^{48}$; —$(CH_2)_p(CHR^{53})_sNR^{23}R^{24}$; —$(CH_2)_p(CHR^{53})_sOCONR^{50}R^{67}$; —$(CH_2)_p(CHR^{53})_sNR^{11}CONR^{50}R^{51}$; —$(CH_2)_p(CHR^{53})_sNR^{11}COR^{56}$; —$(CH_2)_p(CHR^{53})_sCOOR^{49}$; —$(CH_2)_p(CHR^{53})_sCONR^{50}R^{51}$; —$(CH_2)_p(CHR^{53})_sPO(OR^{52})_2$; —$(CH_2)_p(CHR^{53})_sSO_2R^{54}$; or —$(CH_2)_o(CHR^{53})_sR^{69}$;

$R^{10}$ is lower alkyl; —$(CH_2)_p(CHR^{53})_sOR^{47}$; —$(CH_2)_p(CHR^{53})_sSR^{48}$; —$(CH_2)_p(CHR^{53})_sNR^{23}R^{24}$; —$(CH_2)_p(CHR^{53})_sOCONR^{50}R^{67}$; —$(CH_2)_p(CHR^{53})_sNR^{11}CONR^{50}R^{51}$; —$(CH_2)_p(CHR^{53})_sNR^{11}COR^{56}$; —$(CH_2)_p(CHR^{53})_sCOOR^{49}$; —$(CH_2)_p(CHR^{53})_sCONR^{50}R^{51}$; —$(CH_2)_p(CHR^{53})_sPO(OR^{52})_2$; —$(CH_2)_p(CHR^{53})_sSO_2R^{62}$; or —$(CH_2)_o(CHR^{53})_sR^{69}$; or $R^9$ and $R^{10}$ taken together can form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—;

$R^{11}$ is H; alkyl; alkenyl; or aryl-lower alkyl;

$R^{12}$ is H; alkyl; alkenyl; —$(CH_2)_o(CHR^{53})_sOR^{47}$; —$(CH_2)_o(CHR^{53})_sSR^{48}$; —$(CH_2)_o(CHR^{53})_sNR^{23}R^{24}$; —$(CH_2)_o(CHR^{53})_sOCONR^{50}R^{67}$; —$(CH_2)_o(CHR^{53})_sNR^{11}CONR^{50}R^{51}$; —$(CH_2)_o(CHR^{53})_sNR^{11}COR^{56}$; —$(CH_2)_o(CHR^{53})_sCOOR^{49}$; —$(CH_2)_o(CHR^{53})_sCONR^{50}R^{51}$; —$(CH_2)_o(CHR^{53})_sPO(OR^{52})_2$; —$(CH_2)_o(CHR^{53})_sSO_2R^{54}$; or —$(CH_2)_o(CHR^{53})_sR^{69}$;

$R^{13}$ is H; alkyl; alkenyl; —$(CH_2)_o(CHR^{53})_sOR^{47}$; —$(CH_2)_o(CHR^{53})_sSR^{48}$; —$(CH_2)_o(CHR^{53})_sNR^{23}R^{24}$; —$(CH_2)_o(CHR^{53})_sOCONR^{50}R^{67}$; —$(CH_2)_o(CHR^{53})_sNR^{11}CONR^{50}R^{51}$; —$(CH_2)_o(CHR^{53})_sNR^{11}COR^{56}$; —$(CH_2)_o(CHR^{53})_sCOOR^{49}$; —$(CH_2)_o(CHR^{53})_sCONR^{50}R^{51}$; —$(CH_2)_o(CHR^{53})_sPO(OR^{52})_2$; —$(CH_2)_o(CHR^{53})_sSO_2R^{54}$; or —$(CH_2)_o(CHR^{53})_sR^{69}$;

$R^{14}$ is H; alkyl; alkenyl; —$(CH_2)_o(CHR^{53})_sOR^{47}$; —$(CH_2)_o(CHR^{53})_sSR^{48}$; —$(CH_2)_o(CHR^{53})_sNR^{23}R^{24}$; —$(CH_2)_o(CHR^{53})_sOCONR^{50}R^{67}$; —$(CH_2)_o(CHR^{53})_sNR^{11}CONR^{50}R^{51}$; —$(CH_2)_o(CHR^{53})_sNR^{11}COR^{56}$; —$(CH_2)_o(CHR^{53})_sCOOR^{49}$; —$(CH_2)_o(CHR^{53})_sCONR^{50}R^{51}$; —$(CH_2)_o(CHR^{53})_sPO(OR^{52})_2$; —$(CH_2)_o(CHR^{53})_sSO_2R^{54}$; or —$(CH_2)_o(CHR^{53})_sR^{69}$;

$R^{15}$ is H; alkyl; alkenyl; —$(CH_2)_m(CHR^{53})_sOR^{47}$; —$(CH_2)_m(CHR^{53})_sSR^{48}$; —$(CH_2)_m(CHR^{53})_sNR^{23}R^{24}$; —$(CH_2)_m(CHR^{53})_sOCONR^{50}R^{67}$; —$(CH_2)_m(CHR^{53})_sNR^{11}CONR^{51}R^{52}$; —$(CH_2)_m(CHR^{53})_sNR^{11}COR^{56}$; —$(CH_2)_o(CHR^{53})_sCOOR^{49}$; —$(CH_2)_o(CHR^{53})_s$ CONR$^{50}$R$^{51}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{53}$)$_s$R$^{69}$;

R$^{16}$ is H; alkyl; alkenyl; —(CH$_2$)$_o$(CHR$^{53}$)$_s$OR$^{47}$; —(CH$_2$)$_o$(CHR$^{53}$)$_s$SR$^{48}$; —(CH$_2$)$_o$(CHR$^{53}$)$_s$NR$^{23}$R$^{24}$; —(CH$_2$)$_o$(CHR$^{53}$)$_s$OCONR$^{50}$R$^{67}$; —(CH$_2$)$_o$(CHR$^{53}$)$_s$NR$^{11}$CONR$^{51}$R$^{52}$; —(CH$_2$)$_o$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{50}$R$^{51}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{53}$)$_s$R$^{69}$;

R$^{17}$ is H; alkyl; alkenyl; —(CH$_2$)$_m$(CHR$^{53}$)$_s$OR$^{47}$; —(CH$_2$)$_m$(CHR$^{53}$)$_s$SR$^{48}$; —(CH$_2$)$_m$(CHR$^{53}$)$_s$NR$^{23}$R$^{24}$; —(CH$_2$)$_m$(CHR$^{53}$)$_s$OCONR$^{50}$R$^{67}$; —(CH$_2$)$_m$(CHR$^{53}$)$_s$NR$^{11}$CONR$^{50}$R$^{51}$; —(CH$_2$)$_m$(CHR$^{53}$)$_s$NR$^{11}$COR$^{56}$; —(CH$_2$)$_r$(CHR$^{53}$)$_s$COOR$^{49}$; —(CH$_2$)$_r$(CHR$^{53}$)$_s$CONR$^{50}$R$^{51}$; —(CH$_2$)$_r$(CHR$^{53}$)$_s$PO(OR$^{52}$)$_2$; —(CH$_2$)$_r$(CHR$^{53}$)$_s$SO$_2$R$^{54}$; or —(CH$_2$)$_o$(CHR$^{53}$)$_s$R$^{69}$;

R$^{18}$ is H; alkyl; alkenyl; —(CH$_2$)$_m$(CHR$^{53}$)$_s$OR$^{47}$; —(CH$_2$)$_m$(CHR$^{53}$)$_s$SR$^{48}$; —(CH$_2$)$_m$(CHR$^{53}$)$_s$NR$^{23}$R$^{24}$; —(CH$_2$)$_m$(CHR$^{53}$)$_s$OCONR$^{50}$R$^{67}$; —(CH$_2$)$_m$(CHR$^{53}$)$_s$NR$^{11}$CONR$^{50}$R$^{51}$; —(CH$_2$)$_m$(CHR$^{53}$)$_s$NR$^{11}$COR$^{56}$; —(CH$_2$)$_r$(CHR$^{53}$)$_s$COOR$^{49}$; —(CH$_2$)$_r$(CHR$^{53}$)$_s$CONR$^{50}$R$^{51}$; —(CH$_2$)$_r$(CHR$^{53}$)$_s$PO(OR$^{52}$)$_2$; —(CH$_2$)$_r$(CHR$^{53}$)$_s$SO$_2$R$^{54}$; or —(CH$_2$)$_q$(CHR$^{53}$)$_s$R$^{69}$;

R$^{19}$ is H; alkyl; alkenyl; —(CH$_2$)$_m$(CHR$^{53}$)$_s$OR$^{47}$; —(CH$_2$)$_m$(CHR$^{53}$)$_s$SR$^{48}$; —(CH$_2$)$_m$(CHR$^{53}$)$_s$NR$^{23}$R$^{24}$; —(CH$_2$)$_m$(CHR$^{53}$)$_s$OCONR$^{50}$R$^{67}$; —(CH$_2$)$_m$(CHR$^{53}$)$_s$NR$^{11}$CONR$^{50}$R$^{51}$; —(CH$_2$)$_m$(CHR$^{53}$)$_s$NR$^{11}$COR$^{56}$; —(CH$_2$)$_r$(CHR$^{53}$)$_s$COOR$^{49}$; —(CH$_2$)$_r$(CHR$^{53}$)$_s$CONR$^{50}$R$^{51}$; —(CH$_2$)$_r$(CHR$^{53}$)$_s$PO(OR$^{52}$)$_2$; —(CH$_2$)$_r$(CHR$^{53}$)$_s$SO$_2$R$^{54}$; or —(CH$_2$)$_q$(CHR$^{53}$)$_s$R$^{69}$; or R$^{18}$ and R$^{19}$ taken together can form: —(CH$_2$)$_{2-6}$—; —(CH$_2$)$_r$O(CH$_2$)$_r$—; —(CH$_2$)$_r$S(CH$_2$)$_r$—; or —(CH$_2$)$_r$NR$^{57}$(CH$_2$)$_r$—;

R$^{20}$ is H; alkyl; alkenyl; —(CH$_2$)$_o$(CHR$^{53}$)$_s$OR$^{47}$; —(CH$_2$)$_o$(CHR$^{53}$)$_s$SR$^{48}$; —(CH$_2$)$_o$(CHR$^{53}$)$_s$NR$^{23}$R$^{24}$; —(CH$_2$)$_o$(CHR$^{53}$)$_s$OCONR$^{50}$R$^{67}$; —(CH$_2$)$_o$(CHR$^{53}$)$_s$NR$^{11}$CONR$^{50}$R$^{51}$; —(CH$_2$)$_o$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{50}$R$^{51}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{53}$)$_s$R$^{69}$;

R$^{21}$ is H; alkyl; alkenyl; —(CH$_2$)$_p$(CHR$^{53}$)$_s$OR$^{47}$; —(CH$_2$)$_p$(CHR$^{53}$)$_s$SR$^{48}$; —(CH$_2$)$_p$(CHR$^{53}$)$_s$NR$^{23}$R$^{24}$; —(CH$_2$)$_p$(CHR$^{53}$)$_s$OCONR$^{50}$R$^{67}$; —(CH$_2$)$_p$(CHR$^{53}$)$_s$NR$^{11}$CONR$^{50}$R$^{51}$; —(CH$_2$)$_p$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{59}$R$^{51}$; —(CH$_2$)$_o$(CHR$^{53}$)$_s$PO(OR$^{52}$)$_2$; —(CH$_2$)$_r$(CHR$^{53}$)$_s$SO$_2$R$^{54}$; or —(CH$_2$)$_r$(CHR$^{53}$)$_s$R$^{69}$;

R$^{22}$ is H; lower alkyl; lower alkenyl, or aryl-lower alkyl;

R$^{23}$ is H; alkyl; alkenyl; —(CH$_2$)$_m$(CHR$^{53}$)$_s$OR$^{47}$; —(CH$_2$)$_m$(CHR$^{53}$)$_s$NR$^{24}$R$^{55}$; —(CH$_2$)$_m$(CHR$^{53}$)$_s$OCONR$^{50}$R$^{67}$; —(CH$_2$)$_m$(CHR$^{53}$)$_s$NR$^{11}$CONR$^{50}$R$^{51}$; —(CH$_2$)$_m$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{50}$R$^{51}$; —(CH$_2$)$_o$(CHR$^{53}$)$_s$COR$^{56}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{53}$)$_s$R$^{69}$;

R$^{24}$ is H; lower alkyl; aryl, or aryl-lower alkyl; or

R$^{23}$ and R$^{24}$ taken together can form: —(CH$_2$)$_{2-6}$—; —(CH$_2$)$_2$O—(CH$_2$)$_2$—; —(CH$_2$)$_2$S(CH$_2$)$_2$—; or —(CH$_2$)$_2$NR$^{57}$(CH$_2$)$_2$—;

R$^{25}$ is H; alkyl; alkenyl; —(CH$_2$)$_m$(CHR$^{53}$)$_s$OR$^{47}$; —(CH$_2$)$_m$(CHR$^{53}$)$_s$NR$^{23}$R$^{24}$; —(CH$_2$)$_m$(CHR$^{53}$)$_s$OCONR$^{50}$R$^{67}$; —(CH$_2$)$_m$(CHR$^{53}$)$_s$NR$^{11}$CONR$^{50}$R$^{51}$; —(CH$_2$)$_m$(CHR$^{53}$)$_s$NR$^{11}$COR$^{56}$; —(CH$_2$)$_p$(CHR$^{53}$)$_s$COOR$^{49}$; —(CH$_2$)$_p$(CHR$^{53}$)$_s$CONR$^{50}$R$^{51}$; —(CH$_2$)$_p$(CHR$^{53}$)$_s$PO(OR$^{52}$)$_2$; —(CH$_2$)$_p$(CHR$^{53}$)$_s$SO$_2$R$^{54}$; or —(CH$_2$)$_p$(CHR$^{53}$)$_s$R$^{69}$;

R$^{26}$ is H; alkyl; alkenyl; —(CH$_2$)$_o$(CHR$^{53}$)$_s$OR$^{47}$; —(CH$_2$)$_o$(CHR$^{53}$)$_s$NR$^{23}$R$^{24}$; —(CH$_2$)$_o$(CHR$^{53}$)$_s$OCONR$^{50}$R$^{67}$; —(CH$_2$)$_o$(CHR$^{53}$)$_s$NR$^{11}$CONR$^{50}$R$^{51}$; —(CH$_2$)$_o$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{50}$R$^{51}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{53}$)$_s$R$^{69}$;

R$^{27}$ is H; F; Br; Cl; NO$_2$; CF$_3$; CN; OCF$_3$; OCHF$_2$; lower alkyl; —(CH$_2$)$_p$(CHR$^{53}$)$_s$OR$^{47}$; —(CH$_2$)$_p$(CHR$^{53}$)$_s$NR$^{23}$R$^{24}$; —(CH$_2$)$_p$(CHR$^{53}$)$_s$OCONR$^{50}$R$^{67}$; —(CH$_2$)$_p$(CHR$^{53}$)$_s$NR$^{11}$CONR$^{50}$R$^{51}$; —(CH$_2$)$_p$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{50}$R$^{51}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{53}$)$_s$R$^{69}$;

R$^{28}$ is H; F; Br; Cl; NO$_2$; CF$_3$; CN; alkyl; alkenyl; OCF$_3$; OCHF$_2$; —(CH$_2$)$_p$(CHR$^{53}$)$_s$OR$^{47}$; —(CH$_2$)$_p$(CHR$^{53}$)$_s$NR$^{23}$R$^{24}$; —(CH$_2$)$_p$(CHR$^{53}$)$_s$OCONR$^{50}$R$^{67}$; —(CH$_2$)$_p$(CHR$^{53}$)$_s$NR$^{11}$CONR$^{50}$R$^{51}$; —(CH$_2$)$_p$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{50}$R$^{51}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{53}$)$_s$R$^{69}$;

R$^{29}$ is H; alkyl; alkenyl; or aryl-lower alkyl;

R$^{30}$ is H; alkyl; alkenyl; or aryl-lower alkyl;

R$^{31}$ is H; F; Br; Cl; NO$_2$; CF$_3$; CN; OCF$_3$; OCHF$_2$; alkyl; alkenyl; —(CH$_2$)$_p$(CHR$^{53}$)$_s$OR$^{47}$; —(CH$_2$)$_p$(CHR$^{53}$)$_s$NR$^{23}$R$^{24}$; —(CH$_2$)$_p$(CHR$^{53}$)$_s$OCONR$^{50}$R$^{67}$; —(CH$_2$)$_p$(CHR$^{53}$)$_s$NR$^{11}$CONR$^{50}$R$^{51}$; —(CH$_2$)$_p$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{50}$R$^{51}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{53}$)$_s$R$^{69}$;

R$^{32}$ is H; F; Br; Cl; NO$_2$; CF$_3$; CN; OCF$_3$; OCHF$_2$; alkyl; alkenyl; —(CH$_2$)$_p$(CHR$^{53}$)$_s$OR$^{47}$; —(CH$_2$)$_p$(CHR$^{53}$)$_s$NR$^{23}$R$^{24}$; —(CH$_2$)$_p$(CHR$^{53}$)$_s$OCONR$^{50}$R$^{67}$; —(CH$_2$)$_p$(CHR$^{53}$)$_s$NR$^{11}$CONR$^{50}$R$^{51}$; —(CH$_2$)$_p$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{50}$R$^{51}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{53}$)$_s$R$^{69}$;

R$^{33}$ is H; alkyl; alkenyl; —(CH$_2$)$_m$(CHR$^{53}$)$_s$OR$^{47}$; —(CH$_2$)$_m$(CHR$^{53}$)$_s$NR$^{23}$R$^{24}$; —(CH$_2$)$_m$(CHR$^{53}$)$_s$OCONR$^{50}$R$^{67}$; —(CH$_2$)$_m$(CHR$^{53}$)$_s$NR$^{11}$CONR$^{50}$R$^{51}$; —(CH$_2$)$_m$(CHR$^{53}$)$_s$NR$^{11}$COR$^{56}$; —(CH$_2$)$_o$(CHR$^{53}$)$_s$COOR$^{49}$; —(CH$_2$)$_o$(CHR$^{53}$)$_s$CONR$^{50}$R$^{51}$; —(CH$_2$)$_o$(CHR$^{53}$)$_s$PO(OR$^{52}$)$_2$; —(CH$_2$)$_o$(CHR$^{53}$)$_s$SO$_2$R$^{54}$; or —(CH$_2$)$_o$(CHR$^{63}$)$_s$R$^{69}$;

R$^{34}$ is H; alkyl; alkenyl; —(CH$_2$)$_o$(CHR$^{53}$)$_s$OR$^{47}$; or —(CH$_2$)$_o$(CHR$^{53}$)$_p$R$^{69}$;

R$^{35}$ is H; alkyl; alkenyl; —(CH$_2$)$_o$(CHR$^{53}$)$_s$OR$^{47}$; or —(CH$_2$)$_o$(CHR$^{63}$)$_p$R$^{69}$;

R$^{36}$ is H; alkyl; alkenyl; —(CH$_2$)$_o$(CHR$^{53}$)$_s$OR$^{47}$; or —(CH$_2$)$_o$(CHR$^{53}$)$_p$R$^{69}$;

R$^{37}$ is H; alkyl; alkenyl; —(CH$_2$)$_o$(CHR$^{53}$)$_s$OR$^{47}$; or —(CH$_2$)$_o$(CHR$^{53}$)$_p$R$^{69}$;

R$^{38}$ is H; alkyl; alkenyl; —(CH$_2$)$_o$(CHR$^{53}$)$_s$OR$^{47}$; or —(CH$_2$)$_o$(CHR$^{53}$)$_p$R$^{69}$;

R$^{39}$ is H; alkyl; alkenyl; —(CH$_2$)$_o$(CHR$^{63}$)$_s$OR$^{47}$; or —(CH$_2$)$_o$(CHR$^{53}$)$_p$R$^{69}$;

R$^{40}$ is H; alkyl; alkenyl; —(CH$_2$)$_o$(CHR$^{53}$)$_s$OR$^{47}$; or —(CH$_2$)$_o$(CHR$^{63}$)$_p$R$^{69}$;

R$^{41}$ is H; alkyl; alkenyl; —(CH$_2$)$_o$(CHR$^{53}$)$_s$OR$^{47}$; or —(CH$_2$)$_o$(CHR$^{53}$)$_p$R$^{69}$;

R$^{42}$ is lower alkyl; lower alkenyl; or aryl-lower alkyl;

R$^{43}$ is H; lower alkyl; aryl; lower alkenyl; or aryl-lower alkyl;

R$^{44}$ is H; alkyl; alkenyl; —(CH$_2$)$_m$(CHR$^{53}$)$_s$OR$^{47}$; —(CH$_2$)$_m$(CHR$^{53}$)$_s$SR$^{48}$; —(CH$_2$)$_m$(CHR$^{53}$)$_s$NR$^{23}$R$^{24}$; —(CH$_2$)$_m$(CHR$^{53}$)$_s$OCONR$^{50}$R$^{67}$; —(CH$_2$)$_m$(CHR$^{53}$)$_s$NR$^{11}$CONR$^{50}$R$^{51}$; —(CH$_2$)$_m$(CHR$^{53}$)$_s$NR$^{11}$COR$^{56}$; —(CH$_2$)$_r$(CHR$^{53}$)$_s$COOR$^{49}$; —(CH$_2$)$_r$(CHR$^{53}$)$_s$ $CONR^{50}R^{51}$; $-(CH_2)_r(CHR^{53})_sPO(OR^{52})_2$; $-(CH_2)_r(CHR^{53})_sSO_2R^{54}$; or $-(CH_2)_o(CHR^{53})_sR^{69}$;

$R^{45}$ is H; alkyl; alkenyl; $-(CH_2)_p(CHR^{53})_sOR^{47}$; $-(CH_2)_p(CHR^{63})_sNR^{23}R^{24}$; $-(CH_2)_p(CHR^{53})_sOCONR^{40}R^{67}$; $-(CH_2)_p(CHR^{53})_sNR^{11}CONR^{51}R^{52}$; $-(CH_2)_p(CHR^{53})_sNR^{11}COR^{56}$; $-(CH_2)_p(CHR^{53})_sCOOR^{49}$; $-(CH_2)_p(CHR^{53})_sCONR^{50}R^{51}$; $-(CH_2)_p(CHR^{53})_sPO(OR^{52})_2$; $-(CH_2)_p(CHR^{53})_sSO_2R^{54}$; or $-(CH_2)_o(CHR^{53})_sR^{69}$;

$R^{46}$ is H; alkyl; alkenyl; $-(CHR^{53})_sCOOR^{49}$; $-(CHR^{53})_sCONR^{50}R^{51}$; $-(CHR^{53})_sPO(OR^{52})_2$; $-(CHR^{53})_sSOR^{54}$; or $-(CHR^{53})_sR^{69}$;

$R^{47}$ is H; lower alkyl; lower alkenyl; aryl-lower alkyl; $-(CH_2)_m(CHR^{53})_sOR^{49}$; $-(CH_2)_m(CHR^{53})_sNR^{23}R^{24}$; $-(CH_2)_m(CHR^{53})_sOCONR^{50}R^{67}$; $-(CH_2)_m(CHR^{53})_sNR^{11}CONR^{50}R^{51}$; $-(CH_2)_m(CHR^{53})_sNR^{11}COR^{56}$; $-(CH_2)_o(CHR^{53})_sCOOR^{49}$; $-(CH_2)_o(CHR^{53})_sCONR^{50}R^{51}$; or $-(CH_2)_o(CHR^{53})_sR^{69}$;

$R^{48}$ is H; lower alkyl; lower alkenyl; aryl-lower alkyl; $-(CH_2)_m(CHR^{53})_sOR^{49}$; $-(CH_2)_m(CHR^{53})_sNR^{23}R^{24}$; $-(CH_2)_m(CHR^{53})_sOCONR^{50}R^{67}$; $-(CH_2)_m(CHR^{53})_sNR^{11}CONR^{50}R^{51}$; $-(CH_2)_m(CHR^{53})_sNR^{11}COR^{56}$; $-(CH_2)_o(CHR^{53})_sCOOR^{49}$; or $-(CH_2)_o(CHR^{53})_sCONR^{50}R^{51}$;

$R^{49}$ is H; lower alkyl; lower alkenyl; aryl lower alkyl; or heteroaryl lower alkyl;

$R^{50}$ is H; lower alkyl; lower alkenyl; aryl; heteroaryl; aryl-lower alkyl; or heteroaryl-lower alkyl;

$R^{51}$ is H; lower alkyl; lower alkenyl; aryl; heteroaryl; aryl-lower alkyl; or heteroaryl-lower alkyl; or $R^{50}$ and $R^{51}$ taken together can form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$;

$R^{52}$ is H; lower alkyl; lower alkenyl; aryl; or aryl-lower alkyl;

$R^{53}$ is H, alkyl; alkenyl; aryl; heteroaryl; aryl-lower alkyl; heteroaryl-lower alkyl; $-(CH_2)_pOR^{47}$; $-(CH_2)_pOCONR^{50}R^{67}$; $-(CH_2)_pNR^{11}CONR^{50}R^{51}$; $-(CH_2)_pNR^{11}COR^{56}$; $-(CH_2)_oCOOR^{49}$; $-(CH_2)_oCONR^{56}R^{51}$; or $-(CH_2)_oPO(OR^{52})_2$;

$R^{54}$ is lower alkyl; lower alkenyl; aryl, heteroaryl; or aryl-lower alkyl;

$R^{55}$ is H; lower alkyl; lower alkenyl; aryl, heteroaryl; aryl-lower alkyl; heteroaryl-lower alkyl; $-COR^{56}$; $-COOR^{49}$; $-CONR^{50}R^{51}$; $-SO_2R^{54}$; or $-PO(OR^{52})_2$; or $R^{24}$ and $R^{55}$ taken together can form: $-(CH_2)_{2-6}-$; $-(CH_2)_2O(CH_2)_2-$; $-(CH_2)_2S(CH_2)_2-$; or $-(CH_2)_2NR^{57}(CH_2)_2-$;

$R^{56}$ is H; lower alkyl; lower alkenyl; $-(CH_2)_p(CHR^{53})_sOR^{57}$; $-(CH_2)_p(CHR^{53})_sSR^{58}$; $-(CH_2)_p(CHR^{53})_sNR^{24}R^{55}$; $-(CH_2)_p(CHR^{53})_sOCONR^{50}R^{67}$; $-(CH_2)_p(CHR^{53})_sNR^{11}CONR^{50}R^{51}$; $-(CH_2)_p(CHR^{53})_sNR^{11}COR^{56}$; or $-(CH_2)_p(CR^{53})_sR^{69}$;

$R^{57}$ is H; lower alkyl; lower alkenyl; aryl, aryl-lower alkyl; heteroaryl-lower alkyl; $-COR^{56}$; $-COOR^{49}$; or $-CONR^{50}R^{51}$;

$R^{58}$ is H; lower alkyl; lower alkenyl; aryl; aryl-lower alkyl; heteroaryl-lower alkyl; or $-CONR^{50}R^{51}$;

$R^{59}$ is H; Cl; Br; F; $NO_2$; $CF_3$; CN; $OCF_3$; $OCHF_2$; $-N^{24}COR^{56}$; lower alkyl; or lower alkenyl;

$R^{60}$ is H; Cl; Br; F; $NO_2$; $CF_3$; CN; $OCF_3$; $OCHF_2$; $-N^{24}COR^{56}$; lower alkyl; or lower alkenyl;

$R^{61}$ is H; Cl; Br; F; $NO_2$; $CF_3$; CN; $OCF_3$; $OCHF_2$; $-N^{24}COR^{56}$; lower alkyl; or lower alkenyl;

$R^{62}$ is H; Cl; Br; F; $NO_2$; $CF_3$; CN; $OCF_3$; $OCHF_2$; $-N^{24}COR^{56}$; lower alkyl; or lower alkenyl;

with the proviso that at least two of $R^{59}$, $R^{60}$, $R^{61}$ and $R^{62}$ are H $R^{63}$ is H; lower alkyl; lower alkenyl; $-(CH_2)_p(CHR^{53})_sOR^{67}$; $-(CH_2)_p(CHR^{53})_sSR^{67}$; $-(CH_2)_p(CHR^{53})_sNR^{23}R^{24}$; $-(CH_2)_p(CHR^{53})_sOCONR^{50}R^{67}$; $-(CH_2)_p(CHR^{53})_sNR^{11}CONR^{50}R^{51}$; $-(CH_2)_p(CHR^{53})_sNR^{11}COR^{56}$; $-(CH_2)_o(CHR^{53})_sCOOR^{67}$; $-(CH_2)_o(CH_2R^{53})_sCONR^{50}R^{51}$; $-(CH_2)_o(CH_2R^{53})_sPO(OR^{54})_2$; $-(CH_2)_o(CH_2R^{53})_sSO_2R^{54}$; or $-(CH_2)_o(CH_2R^{53})_sR^{69}$;

m is 2-4; o is 0-4; p is 1-4; q is 0-2; r is 1 or 2; s is 0 or 1;

Z is a chain of 4 α-amino acid residues, the positions of said amino acid residues in said chain being counted starting from the N-terminal amino acid, whereby these amino acid residues are, depending on their position in the chain, Gly or Pro or of one of the types

C: $-NR^{11}CH(R^{64})CO-$;

D: $-NR^{11}CH(R^{65})CO-$;

E: $-NR^{11}CH(R^{66})CO-$;

F: $-NR^{11}CH(R^{76})CO-$;

$R^{64}$ is H; lower alkyl; lower alkenyl; $-(CH_2)_p(CHR^{78})_sOR^{77}$; or $-(CH_2)_p(CHR^{78})_sSR^{77}$;

$R^{65}$ is $-(CH_2)_oR^{69}$; $-(CH_2)_rO(CH_2)_oR^{69}$; $-(CH_2)_rS(CH_2)_oR^{69}$; or $-(CH_2)_rNR^{11}(CH_2)_oR^{69}$;

$R^{66}$ is $-(CH_2)_pNR^{70}R^{71}$; $-(CH_2)_pNR^{69}R^{72}$; $-(CH_2)_pC(=NR^{72})NR^{76}R^{71}$; $-(CH_2)_pC(=NOR^{42})NR^{70}R^{71}$; $-(CH_2)_pC(=NNR^{70}R^{71})NR^{70}R^{71}$; $-(CH_2)_pNR^{72}C(=NR^{72})NR^{70}R^{71}$; $-(CH_2)_pN=C(NR^{70}R^{72})NR^{71}R^{72}$; $-(CH_2)_pC_6H_4NR^{70}R^{71}$; $-(CH_2)_pC_6H_4NR^{69}R^{72}$; $-(CH_2)_pC_6H_4C(=NR^{72})NR^{70}R^{71}$; $-(CH_2)_pC_6H_4C(=NOR^{42})NR^{70}R^{71}$; $-(CH_2)_pC_6H_4C(=NNR^{70}R^{71})NR^{70}R^{71}$; $-(CH_2)_pC_6H_4NR^{72}C(=NR^{72})NR^{70}R^{71}$; $-(CH_2)_pC_6H_4N=C(NR^{70}R^{72})NR^{71}R^{72}$; $-(CH_2)_rO(CH_2)_mNR^{70}R^{71}$; $-(CH_2)_rO(CH_2)_mNR^{69}R^{72}$; $-(CH_2)_rO(CH_2)_pC(=NR^{72})NR^{70}R^{71}$; $-(CH_2)_rO(CH_2)_pC(=NOR^{42})NR^{70}R^{71}$; $-(CH_2)_rO(CH_2)_pC(=NNR^{70}R^{71})NR^{70}R^{71}$; $-(CH_2)_rO(CH_2)_mNR^{72}C(=NR^{72})NR^{70}R^{71}$; $-(CH_2)_rO(CH_2)_mN=C(NR^{70}R^{72})NR^{71}R^{72}$; $-(CH_2)_rO(CH_2)_pC_6H_4CNR^{70}R^{71}$; $-(CH_2)_rO(CH_2)_pC_6H_4C(=NR^{72})NR^{70}R^{71}$; $-(CH_2)_rO(CH_2)_pC_6H_4C(=NOR^{42})NR^{70}R^{71}$; $-(CH_2)_rO(CH_2)_pC_6H_4C(=NNR^{70}R^{71})NR^{70}R^{71}$; $-(CH_2)_rO(CH_2)_pC_6H_4NR^{72}C(=NR^{72})NR^{70}R^{71}$; $-(CH_2)_rS(CH_2)_mNR^{70}R^{71}$; $-(CH_2)_rS(CH_2)_mNR^{69}R^{72}$; $-(CH_2)_rS(CH_2)_pC(NR^{72})NR^{70}R^{71}$; $-(CH_2)_rS(CH_2)_pC(=NOR^{42})NR^{70}R^{71}$; $-(CH_2)_rS(CH_2)_pC(=NNR^{70}R^{71})NR^{70}R^{71}$; $-(CH_2)_rS(CH_2)_mNR^{72}C(=NR^{72})NR^{70}R^{71}$; $-(CH_2)_rS(CH_2)_mN=C(NR^{70}R^{72})NR^{71}R^{72}$; $-(CH_2)_rS(CH_2)_pC_6H_4CNR^{70}R^{71}$; $-(CH_2)_rS(CH_2)_pC_6H_4C(=NR^{72})NR^{70}R^{71}$; $-(CH_2)_rS(CH_2)_pC_6H_4C(=NOR^{42})NR^{70}R^{71}$; $-(CH_2)_rS(CH_2)_pC_6H_4C(=NNR^{70}R^{71})NR^{70}R^{71}$; $-(CH_2)_rS(CH_2)_pC_6H_4NR^{72}C(=NR^{72})NR^{70}R^{71}$; $-(CH_2)_pNR^{72}COR^{56}$; $-(CH_2)_pNR^{72}COR^{69}$;

$R^{67}$ is lower alkyl; lower alkenyl; or aryl-lower alkyl; or $R^{50}$ and $R^{67}$ taken together can form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; or $R^{68}$ is H; lower alkyl; lower alkenyl; aryl-lower alkyl; $-(CH_2)_oOR^{64}$; $-(CH_2)_oSR^{64}$; $-(CH_2)_oNR^{23}R^{24}$; $-(CH_2)_oOCONR^{50}R^{67}$; $-(CH_2)_oNR^{11}CONR^{50}R^{51}$; $-(CH_2)_oNR^{11}COR^{56}$; $-(CH_2)_oCOOR^{67}$; $-(CH_2)_oCONR^{50}R^{51}$; $-(CH_2)_oPO(OR^{52})_2$; $-(CH_2)_oSO_2R^{54}$; or $-(CH_2)_oCOR^{56}$;

$R^{69}$ is $-C_6R^{59}R^{60}R^{61}R^{62}R^{68}$; or a heteroaryl group of one of the formulae

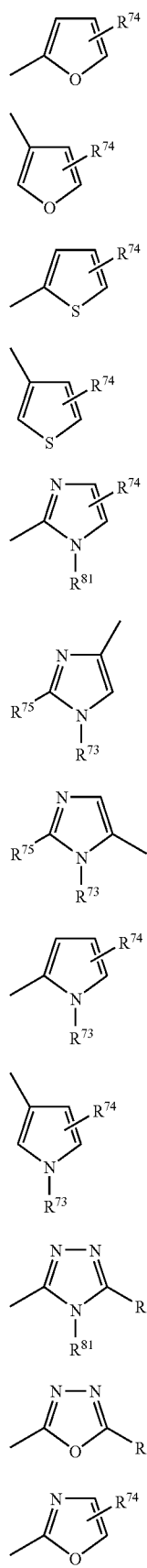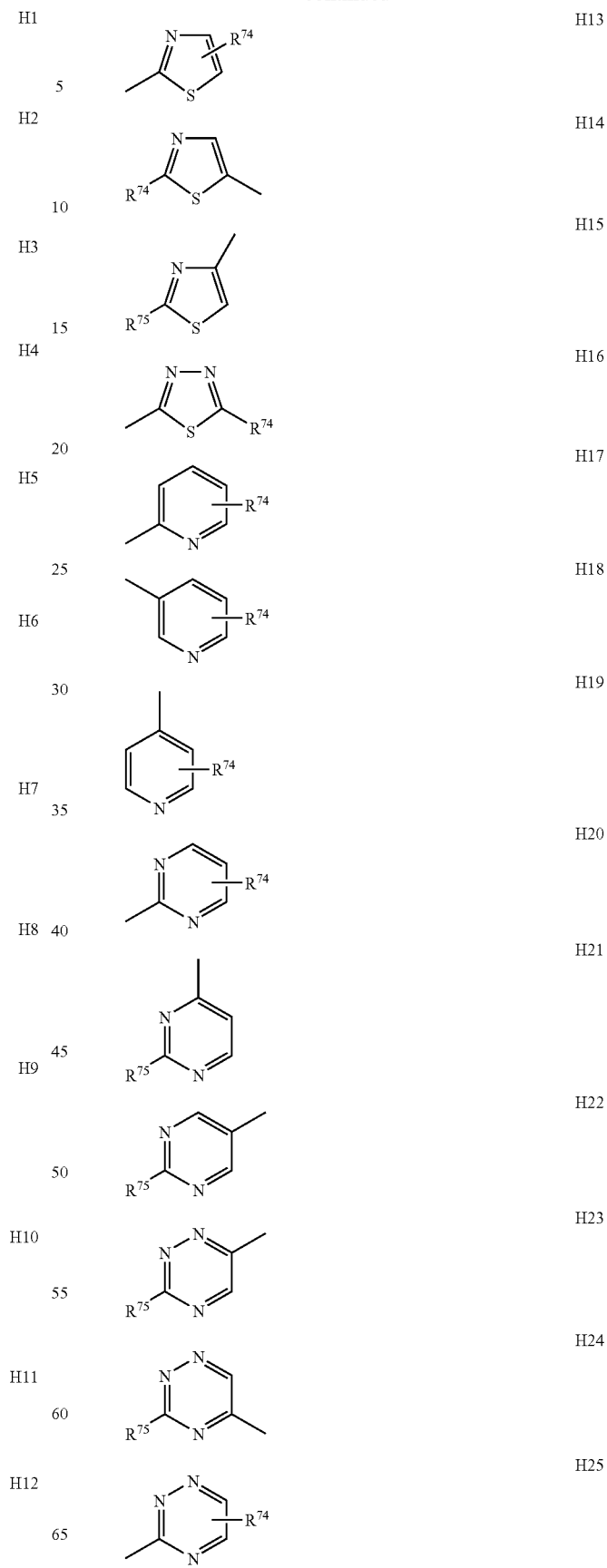

27
-continued
H26 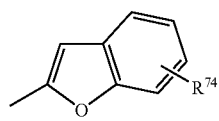
H27 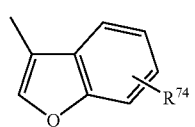
H28 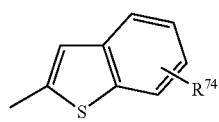
H29 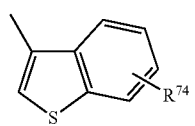
H30 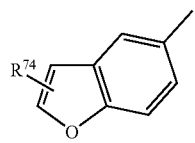
H31 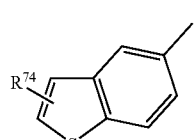
H32 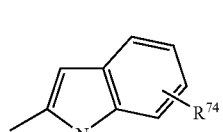
H33 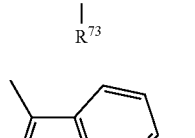
H34 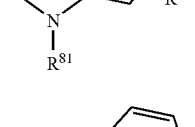
H35 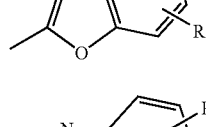
H36 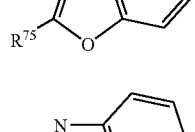
28
-continued
H37 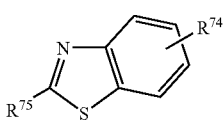
H38 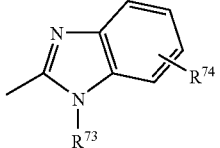
H39 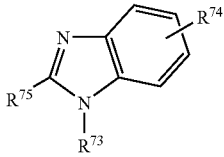
H40 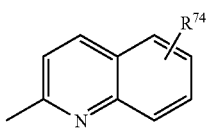
H41 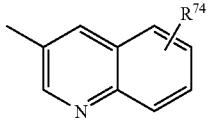
H42 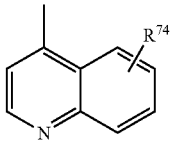
H43 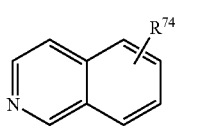
H44 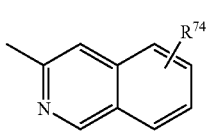
H45 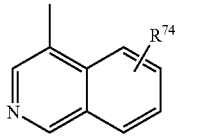
H46 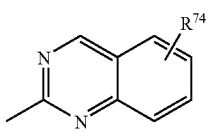
H47 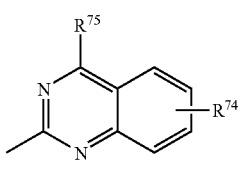

H48

[chemical structure with R74, R75]

H49

[chemical structure with R74]

H50

[chemical structure with R74]

H51

[chemical structure with R74, R75]

H52

[chemical structure with R74]

H53

[chemical structure with R74]

H54

[chemical structure with R74]

$R^{70}$ is H; lower alkyl; aryl; or aryl-lower alkyl;
$R^{69}$ and $R^{72}$ taken together can form: $-(CH_2)_{2-6}-$; $-(CH_2)_2 O(CH_2)_2-$; $-(CH_2)_2S(CH_2)_2-$; or $-(CH_2)_2 NR^{49}(CH_2)_2-$;
$R^{71}$ is H; lower alkyl; aryl; or aryl-lower alkyl; or
$R^{70}$ and $R^{71}$, taken together, can be $-(CH_2)_{2-7}-$; $-(CH_2)_2 O(CH_2)_2-$; or $-(CH_2)_2NR^{57}(CH_2)_2-$;
$R^{72}$ is H; or lower alkyl;
$R^{73}$ is H; lower alkyl; or aryl-lower alkyl;
$R^{74}$ is H; lower alkyl; aryl; heteroaryl; or aryl-lower alkyl; or
$R^{75}$ is H; lower alkyl; aryl; or $-NR^{70}R^{71}$;
$R^{76}$ is $-(CH_2)_p(CHR^{79})_sOH$; $-(CH_2)_p(CHR^{79})_s CONR^{70}R^{71}$; $-(CH_2)_p(CHR^{79})_sCOOR^{49}$; $-(CH_2)_p (CHR^{79})_sNR^{72}CONR^{70}R^{71}$; $-(CH_2)_p(CHR^{79})_s NR^{11}COR^{56}$; $-(CH_2)_pC_6H_4CONR^{70}R^{71}$; or $-(CH_2)_p C_6H_4NR^{72}CONR^{70}R^{71}$;
$R^{77}$ is lower alkyl; or lower alkenyl;
$R^{78}$ is H; alkyl; alkenyl; $-(CH_2)_pOR^{77}$; or $-(CH_2)_pSR^{77}$;
$R^{79}$ is H; alkyl; alkenyl; aryl; heteroaryl; aryl-lower alkyl; $-(CH_2)_pOR^{77}$; $-(CH_2)_pOCONR^{50}R^{67}$; $-(CH_2)_p NR^{11}CONR^{50}R^{67}$; $-(CH_2)_pNR^{11}COR^{56}$; $-(CH_2)_o COOR^{49}$; $-(CH_2)_oCONR^{50}R^{51}$; $-(CH_2)_oPO(OR^{52})_2$; or $-(CH_2)_oSO_2R^{54}$;

with the proviso that in said chain of 4 α-amino acid residues Z the amino acid residues in positions 1 to 4 are:

P1: of type C, or of type D or of type E, or of type F; or the residue is Gly;
P2: of type E, or of type C, or of type D; or the residue is Gly or Pro;
P3: of type C or of type E or of type D or of type F; or the residue is Gly or Pro;
P4: of type C, or of type D or of type E, or of type F, or the residue is Gly, at P2 and P3 also D-isomers being possible;

and pharmaceutically acceptable salts thereof.

In accordance with the present invention these β-hairpin peptidomimetics can be prepared by a process which comprises (a) coupling an appropriately functionalized solid support with a compound of the general formula

II

[structure with OH, O=, X, N, Template]

wherein

[structure with O=, N, Template]

is as defined above and X is an N-protecting group or, alternatively, if

[structure with O=, N, Template]

is to be group (a1) or (a2), above, (aa) coupling said appropriately functionalized solid support with an appropriately N-protected derivative of an amino acid of the general formula

HOOC—B—H          III or

HOOC-A-H          IV wherein B and A are as defined above, any functional group which may be present in said N-protected amino acid derivative being likewise appropriately protected;

(ab) removing the N-protecting group from the product thus obtained; and (ac) coupling the product thus obtained with an appropriately N-protected derivative of an amino acid of the above general formula IV and, respectively, III, any functional group which may be present in said N-protected amino acid derivative being likewise appropriately protected;

(b) removing the N-protecting group from the product obtained in step (a), or (ac);
(c) coupling the product thus obtained with an appropriately N-protected derivative of that amino acid which in the desired end-product is in position 4, any functional group which may be present in said N-protected amino acid derivative being likewise appropriately protected;
(d) removing the N-protecting group from the product thus obtained;
(e) coupling the product thus obtained with an appropriately N-protected derivative of that amino acid which in the desired end-product is one position farther away from position 4, any functional group which may be present in said N-protected amino acid derivative being likewise appropriately protected;
(f) removing the N-protecting group from the product thus obtained;
(g) repeating steps (e) and (f) until all amino acid residues have been introduced;
(h) if desired, selectively deprotecting one or several protected functional group(s) present in the molecule and appropriately substituting the reactive group(s) thus liberated;
(i) detaching the product thus obtained from the solid support;
(j) cyclizing the product cleaved from the solid support;
(k) removing any protecting groups present on functional groups of any members of the chain of amino acid residues and, if desired, any protecting group(s) which may in addition be present in the molecule; and
(l) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

The peptidomimetics of the present invention can also be enantiomers of the compounds of formula I. These enantiomers can be prepared by a modification of the above process in which enantiomers of all chiral starting materials are used.

As used in this description, the term "alkyl", taken alone or in combinations, designates saturated, straight-chain or branched hydrocarbon radicals having up to 24, preferably up to 12, carbon atoms, optionally substituted with halogen. Similarly, the term "alkenyl" designates straight chain or branched hydrocarbon radicals having up to 24, preferably up to 12, carbon atoms and containing at least one or, depending on the chain length, up to four olefinic double bonds, optionally substituted with halogen. The term "lower" designates radicals and compounds having up to 6 carbon atoms. Thus, for example, the term "lower alkyl" designates saturated, straight-chain or branched hydrocarbon radicals having up to 6 carbon atoms, such as methyl, ethyl, n-propyl, isopropyl, n-butyl, sec.-butyl, isobutyl, tert.-butyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $OCF_3OCHF_2$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{69}$.

The structural element -A-CO— designates amino acid building blocks which in combination with the structural element —B—CO— form templates (a1) and (a2). Templates (a) through (s) constitute building blocks which have an N-terminus and a C-terminus oriented in space in such a way that the distance between those two groups may lie between 4.0-5.5 A. A peptide chain Z is linked to the C-terminus and the N-terminus of the templates (a) through (s) via the corresponding N- and C-termini so that the template and the chain form a cyclic structure such as that depicted in formula I. In a case as here where the distance between the N- and C-termini of the template lies between 4.0-5.5 A the template will induce the H-bond network necessary for the formation of a β-hairpin conformation in the peptide chain Z. Thus template and peptide chain form a β hairpin mimetic.

The β-hairpin conformation is highly relevant for the agonizing or antagonizing activity activity of the β-hairpin mimetics of the present invention. The β-hairpin stabilizing conformational properties of the templates (a) through (s) play a key role not only for the agonizing or antagonizing activity but also for the synthesis process defined hereinabove, as incorporation of the templates at the beginning of the linear protected peptide precursors enhances cyclization yields significantly.

Building blocks A1-A71 belong to a class of amino acids wherein the N-terminus is a secondary amine forming part of a ring. Among the genetically encoded amino acids only proline falls into this class. The configuration of building block A1 through A71 is (D), and they are combined with a building block —B—CO— of (L)-configuration A1 through A69. Preferred combinations for templates (a1) are $^D$A1-CO—$^L$B—CO— to $^D$A71-CO—$^L$B—CO—. Thus, for example, $^D$Pro-$^L$Tic constitutes the prototype of templates (a1). Less preferred, but possible are combinations —CO—$^D$B—CO-$^L$A1-CO— to —$^D$B—CO$^L$A71-CO— forming templates (a2). Thus, for example, $^L$-Pro-$^D$Tic constitutes the prototype of template (a2).

It will be appreciated that building blocks -A1-CO— to -A71-CO— in which A has (D)-configuration, are carrying a group $R^1$ at the α-position to the N-terminus. The preferred values for $R^1$ are H and lower alkyl with the most preferred values for $R^1$ being H and methyl. It will be recognized by those skilled in the art, that A1-A71 are shown in (D)-configuration which, for $R^1$ being H and methyl, corresponds to the (R)-configuration. Depending on the priority of other values for $R^1$ according to the Cahn, Ingold and Prelog-rules, this configuration may also have to be expressed as (S).

In addition to $R^1$ building blocks -A1-CO— to -A33-CO— can carry an additional substituent designated as $R^2$ to $R^8$. This additional substituent can be H, and if it is other than H, it is preferably a small to medium-sized aliphatic or aromatic group. Examples of preferred values for $R^2$ to $R^8$ are:

$R^2$: H; lower alkyl; lower alkenyl; $(CH_2)_pOR^{47}$ (where $R^{47}$: lower alkyl; or lower alkenyl); $(CH_2)_pSR^{48}$ (where $R^{48}$: lower alkyl; or lower alkenyl); $(CH_2)_pNR^{23}R^{24}$ (where $R^{23}$: lower alkyl; or lower alkenyl; $R^{24}$: H; or lower alkyl; $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2$ $NR^{49}(CH_2)_2$—; $R^{49}$: H; or lower alkyl); $(CH_2)_p$ $OCONR^{50}R^{67}$ (where $R^{50}$: H; or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_p$ $NR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2$ $NR^{49}(CH_2)_2$—; where $R^{49}$: H; or lower alkyl); —$(CH_2)_pN(R^{11})COR^{56}$(where: $R^{11}$: H; or lower alkyl; $R^{56}$: lower alkyl; or lower alkenyl); —$(CH_2)_o$ $COOR^{49}$ (where $R^{49}$: lower alkyl; or lower alkenyl);

—(CH$_2$)$_o$CONR$^{50}$R$^{51}$ (where R$^{50}$: lower alkyl; or lower alkenyl; and R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$PO(OR$^{52}$)$_2$ (where R$^{52}$: lower alkyl; or lower alkenyl); —(CH$_2$)$_o$SO$_2$R$^{54}$ (where R$^{54}$: lower alkyl; or lower alkenyl); or —(CH$_2$)$_q$C$_6$H$_4$R$^3$ (where R$^3$: H; F; CF$_3$; lower alkyl; lower alkenyl; or lower alkoxy).

R$^3$: H; F; Cl; CF$_3$, OCF$_3$; OCHF$_2$; lower alkyl; lower alkenyl; —(CH$_2$)$_o$OR$^{48}$ (where R$^{48}$: lower alkyl; or lower alkenyl); (CH$_2$)$_o$SR$^{43}$ (where R$^{43}$: lower alkyl; or lower alkenyl); —(CH$_2$)$_o$NR$^{23}$R$^{24}$ (where R$^{23}$: lower alkyl; or lower alkenyl; R$^{24}$: H; or lower alkyl; or R$^{23}$ and R$^{24}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$OCONR$^{50}$R$^{67}$ (where R$^{50}$: H; or lower alkyl; or lower alkenyl; R$^{67}$: lower alkyl; or R$^{50}$ and R$^{67}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$NR$^{11}$CONR$^{50}$R$^{51}$ (where R$^{11}$: H; or lower alkyl; R$^{50}$: H; or lower alkyl; or lower alkenyl; R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$N(R$^{11}$)COR$^{56}$ (where: H; or lower alkyl; R$^{56}$: lower alkyl; or lower alkenyl); —(CH$_2$)$_o$COOR$^{49}$ (where R$^{49}$: lower alkyl; or lower alkenyl); —(CH$_2$)$_o$CONR$^{50}$R$^{51}$ (where R$^{50}$: lower alkyl; or lower alkenyl; and R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$; H; or lower alkyl); —(CH$_2$)$_o$PO(OR$^{52}$)$_2$ (where R$^{52}$: lower alkyl; or lower alkenyl); —(CH$_2$)$_o$SO$_2$R$^{54}$ (where R$^{54}$: lower alkyl; or lower alkenyl); or —(CH$_2$)$_q$C$_6$H$_4$R$^3$ (where R$^3$: H; F; Cl; CF$_3$; OCF$_3$; OCHF$_2$; lower alkyl; lower alkenyl; or lower alkoxy).

R$^4$: H; lower alkyl; lower alkenyl; —(CH$_2$)$_m$OR$^{47}$ (where R$^{47}$: lower alkyl; or lower alkenyl); —(CH$_2$).SR$^{48}$ (where R$^{48}$: lower alkyl; or lower alkenyl); —(CH$_2$)$_m$NR$^{23}$R$^{24}$ (where R$^{23}$: lower alkyl; or lower alkenyl; R$^{24}$: H; or lower alkyl; or R$^{23}$ and R$^{24}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_m$OCONR$^{50}$R$^{67}$ (where R$^{50}$: H; or lower alkyl; or lower alkenyl; R$^{67}$: lower alkyl; or R$^{50}$ and R$^{67}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_m$NR$^{11}$CONR$^{50}$R$^{51}$ (where R$^{11}$: H; or lower alkyl; R$^{50}$: H; or lower alkyl; or lower alkenyl; R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$ NR$^{49}$(CH$_2$)$_2$—; where R$^{49}$: H; or lower alkyl); —(CH$_2$)$_m$N(R$^{11}$)COR$^{56}$(where: R$^{11}$: H; or lower alkyl; R$^{56}$: lower alkyl; or lower alkenyl); —(CH$_2$)$_o$COOR$^{49}$ (where R$^{49}$: lower alkyl; or lower alkenyl); —(CH$_2$)$_o$CONR$^{50}$R$^{51}$ (where R$^{50}$: lower alkyl; or lower alkenyl; and R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$PO(OR$^{52}$)$_2$ (where R$^{52}$: lower alkyl; or lower alkenyl); —(CH$_2$)$_o$SO$_2$R$^{54}$ (where R$^{54}$: lower alkyl; or lower alkenyl); or —(CH$_2$)$_q$C$_6$H$_4$R$^3$ (where R$^3$: H; F; Cl; CF$_3$; OCF$_3$; OCHF$_2$; lower alkyl; lower alkenyl; or lower alkoxy).

R$^5$: H; lower alkyl; lower alkenyl; —(CH$_2$)$_m$OR$^{47}$ (where R$^{47}$: lower alkyl; or lower alkenyl); —(CH$_2$)$_m$SR$^{48}$ (where R$^{43}$: lower alkyl; or lower alkenyl); —(CH$_2$).NR$^{23}$R$^{24}$ (where R$^{23}$: lower alkyl; or lower alkenyl; R$^{24}$: H; or lower alkyl; or R$^{23}$ and R$^{24}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_m$OCONR$^{50}$R$^{67}$ (where R$^{50}$: H; or lower alkyl; or lower alkenyl; R$^{67}$: lower alkyl; or R$^{50}$ and R$^{67}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_m$NR$^{11}$CONR$^{50}$R$^{51}$ (where R$^{11}$: H; or lower alkyl; R$^{50}$: H; or lower alkyl; or lower alkenyl; R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$ NR$^{49}$(CH$_2$)$_2$—; where R$^{49}$: H; or lower alkyl); —(CH$_2$)$_m$N(R$^{11}$)COR$^{56}$ (where: R$^{11}$: H; lower alkyl; R$^{56}$: lower alkyl; or lower alkenyl); —(CH$_2$)$_o$COOR$^{49}$ (where R$^{49}$: lower alkyl; or lower alkenyl); —(CH$_2$)$_o$CONR$^{50}$R$^{51}$ (where R$^{50}$: lower alkyl; or lower alkenyl; and R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$PO(OR$^{52}$)$_2$ (where R$^{52}$: lower alkyl; or lower alkenyl); —(CH$_2$)$_o$SO$_2$R$^{54}$ (where R$^{54}$: lower alkyl; or lower alkenyl); —(CH$_2$)$_q$C$_6$H$_4$R$^3$ (where R$^3$: H; F; Cl; CF$_3$; OCF$_3$; OCHF$_2$; lower alkyl; lower alkenyl; or lower alkoxy).

R$^6$: H; lower alkyl; lower alkenyl; —(CH$_2$)$_m$0R$^{47}$ (where R$^{47}$: lower alkyl; or lower alkenyl); —(CH$_2$)$_m$SR$^{48}$ (where R$^{43}$: lower alkyl; or lower alkenyl); —(CH$_2$)$_m$NR$^{17}$R$^{23}$ (where R$^{23}$: lower alkyl; or lower alkenyl; R$^{24}$: H; or lower alkyl; or R$^{23}$ and R$^{24}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_m$OCONR$^{50}$R$^{67}$ (where R$^{50}$: H; or lower alkyl; or lower alkenyl; R$^{67}$: lower alkyl; or R$^{50}$ and R$^{67}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_m$NR$^{11}$CONR$^{50}$R$^{51}$ (where R$^{11}$: H; or lower alkyl; R$^{50}$: H; or lower alkyl; or lower alkenyl; R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$ NR$^{49}$(CH$_2$)$_2$—; where R$^{49}$: H; or lower alkyl); —(CH$_2$)$_m$N(R$^{11}$)COR$^{56}$ (where: R$^{11}$: H; or lower alkyl; R$^{56}$: lower alkyl; or lower alkenyl); —(CH$_2$)$_o$COOR$^{49}$ (where R$^{49}$: lower alkyl; or lower alkenyl); —(CH$_2$)$_o$CONR$^{50}$R$^{51}$ (where R$^{50}$: lower alkyl; or lower alkenyl; and R$^{51}$: H; or lower alkyl; or R$^{50}$ and R$^{51}$ taken together form: —(CH$_2$)$_{2-6}$—; —(CH$_2$)$_2$O(CH$_2$)$_2$—; (CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$PO(OR$^{52}$)$_2$ (where R$^{52}$: lower alkyl; or lower alkenyl); —(CH$_2$)$_o$SO$_2$R$^{54}$ (where R$^{54}$: lower alkyl; or lower alkenyl); or —(CH$_2$)$_q$ C$_6$H$_4$R$^3$ (where R$^3$: H; F; Cl; CF$_3$; OCF$_3$; OCHF$_2$; lower alkyl; lower alkenyl; or lower alkoxy).

R$^7$: H; lower alkyl; lower alkenyl; —(CH$_2$)$_m$OR$^{47}$ (where R$^{47}$: lower alkyl; or lower alkenyl); —(CH$_2$).SR$^{48}$ (where R$^{48}$: lower alkyl; or lower alkenyl); —(CH$_2$).NR$^{23}$R$^{24}$ (where R$^{23}$: lower alkyl; or lower alkenyl; R$^{24}$: H; or lower alkyl; or R$^{23}$ and R$^{24}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_m$OCONR$^{50}$R$^{67}$ (where R$^{50}$: H; or lower alkyl; or lower alkenyl; R$^{67}$: lower alkyl; or R$^{50}$ and R$^{67}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_m$NR$^{11}$CONR$^{50}$R$^{51}$ (where R$^{11}$: H; or lower alkyl; R$^{50}$: H; or lower alkyl; or lower alkenyl; R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$ NR$^{49}$(CH$_2$)$_2$—; where R$^{49}$: H; or lower alkyl); —(CH$_2$)$_m$N(R$^{11}$)COR$^{56}$ (where: R$^{11}$: H; or lower alkyl; R$^{56}$: lower alkyl; or lower alkenyl); —(CH$_2$)$_r$COOR$^{49}$ (where R$^{49}$: lower alkyl; or lower alkenyl); —(CH$_2$)$_r$CONR$^{50}$R$^{51}$ (where R$^{50}$: lower alkyl; or lower alkenyl; and R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_r$PO(OR$^{52}$)$_2$ (where R$^{52}$: lower alkyl; or lower alkenyl); —(CH$_2$)$_o$SO$_2$R$^{54}$ (where R$^{54}$: lower alkyl; or lower alkenyl); or —(CH$_2$)$_q$C$_6$H$_4$R$^3$ (where R$^3$: H; F; Cl; CF$_3$; OCF$_3$; OCHF$_2$; lower alkyl; lower alkenyl; or lower alkoxy).

R$^8$: H; lower alkyl; lower alkenyl; —(CH$_2$)$_o$OR$^{47}$ (where R$^{47}$: lower alkyl; or lower alkenyl); —(CH$_2$)$_o$SR$^{48}$ (where R$^{48}$: lower alkyl; or lower alkenyl); —(CH$_2$)$_o$NR$^{23}$R$^{24}$ (where R$^{23}$: lower alkyl; or lower alkenyl; R$^{24}$: H; or lower alkyl; or R$^{23}$ and R$^{24}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$OCONR$^{50}$R$^{67}$ (where R$^{50}$: H; or lower alkyl; or lower alkenyl; R$^{67}$: lower alkyl; or R$^{50}$ and R$^{67}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$NR$^{11}$CONR$^{50}$R$^{51}$ (where R$^{11}$: H; or lower alkyl; R$^{50}$: H; or lower alkyl; or lower alkenyl; R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$ NR$^{49}$(CH$_2$)$_2$—; where R$^{49}$: H; or lower alkyl); —(CH$_2$)$_o$N(R$^{11}$)COR$^{56}$ (where: R$^{11}$: H; or lower alkyl; R$^{56}$: lower alkyl; or lower alkenyl); —(CH$_2$)$_o$COOR$^{49}$ (where R$^{49}$: lower alkyl; or lower alkenyl); —(CH$_2$)$_o$CONR$^{50}$R$^{51}$ (where R$^{50}$: lower alkyl; or lower alkenyl; and R$^{51}$: H; or lower alkyl; or R$^{50}$ and R$^{51}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_o$PO(OR$^{52}$)$_2$ (where R$^{52}$: lower alkyl; or lower alkenyl); —(CH$_2$)$_o$SO$_2$R$^{54}$ (where R$^{54}$: lower alkyl; or lower alkenyl); or —(CH$_2$)$_q$C$_6$H$_4$R$^3$ (where R$^3$: H; F; Cl; CF$_3$; OCF$_3$; OCHF$_2$; lower alkyl; lower alkenyl; or lower alkoxy).

Among the building blocks A1 to A71 the following are preferred: A2 with R$^2$ being H, A12 with R$^3$ being H, A69, A70 with R$^2$ being H, or A71 with R$^5$ being H.

Most preferred are building blocks of type A71':

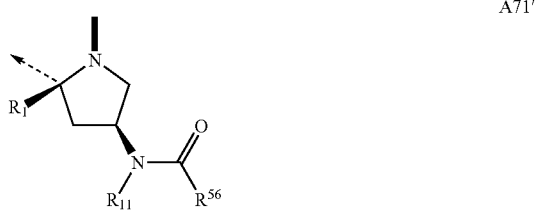

A71' wherein R$^{11}$ is H or lower alkyl; and R$^{56}$ is alkyl; alkenyl; aryl; aryl-lower alkyl; or heteroaryl-lower alkyl; especially those wherein R$^{56}$ is n-hexyl (A71'-1); n-heptyl (A71'-2); 4-(phenyl)benzyl (A71'-3); diphenylmethyl (A71'-4); 3-amino-propyl (A71'-5); 5-amino-pentyl (A71'-6); methyl (A71'-7); ethyl (A71'-8); isopropyl (A71'-9); isobutyl (A71'-10); n-propyl (A71'-11); cyclohexyl (A71'-12); cyclohexylmethyl (A71'-13); n-butyl (A71'-14); phenyl (A71'-15); benzyl (A71'-16); (3-indolyl)methyl (A71'-17); 2-(3-indolyl)ethyl (A71'-18); (4-phenyl)phenyl (A71'-19); and n-nonyl (A71'-20).

Building block A34 belongs to the class of open-chain α-substituted α-amino acids, building blocks A35 and A36 to the corresponding β-amino acid analogues and building blocks A37-A71 to the cyclic analogues of A34. Such amino acid derivatives have been shown to constrain small peptides in well defined reverse turn or U-shaped conformations (C. M. Venkatachalam, *Biopolymers*, 1968, 6, 1425-1434; W. Kabsch, C Sander, *Biopolymers* 1983, 22, 2577). Such building blocks or templates are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks -A34-CO— to A68-CO— in combination with a building block —B—CO— of L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714).

Thus, for the purposes of the present invention templates (a1) and (a2) can also consist of -A34-CO— to A71-CO— where building block A34 to A71 is of (D)-configuration, in combination with a building block B—CO— of (L)-configuration.

Preferred values for R$^{11}$ in A34 to A71 are H or lower alkyl with methyl being most preferred. Preferred values for R$^9$-R$^{20}$ in building blocks A34 to A68 are the following:

R$^9$: lower alkyl.

R$^{10}$: lower alkyl; lower alkenyl; —(CH$_2$)$_p$OR$^{47}$ (where R$^{47}$: lower alkyl; or lower alkenyl); —(CH$_2$)$_p$SR$^{48}$ (where R$^{48}$: lower alkyl; or lower alkenyl); —(CH$_2$)$_p$NR$^{23}$R$^{24}$ (where R$^{23}$: lower alkyl; or lower alkenyl; R$^{24}$: H; or lower alkyl; or R$^{23}$ and R$^{24}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_p$OCONR$^{50}$R$^{67}$ (where R$^{50}$: H; or lower alkyl; or lower alkenyl; R$^{67}$: lower alkyl; or R$^{50}$ and R$^{67}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl); —(CH$_2$)$_p$ $NR^{11}CONR^{51}R^{52}$ (where $R^{11}$: H; or lower alkyl; $R^{51}$: H; or lower alkyl; or lower alkenyl; $R^{82}$: H; or lower alkyl; or $R^{51}$ and $R^{52}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_pN(R^{11})COR^{56}$ (where: $R^{20}$: H; or lower alkyl; $R^{56}$: lower alkyl; or lower alkenyl); $-(CH_2)_pCOOR^{49}$ (where $R^{49}$: lower alkyl; or lower alkenyl); $-(CH_2)_pCONR^{50}R^{51}$ (where $R^{50}$: lower alkyl; or lower alkenyl; and $R^{51}$: H; or lower alkyl; or $R^{50}$ and $R^{51}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_pPO(OR^{52})_2$ (where $R^{52}$: lower alkyl; or lower alkenyl); $-(CH_2)_pSO_2R^{54}$ (where $R^{54}$: lower alkyl; or lower alkenyl); or $-(CH_2)_qC_6H_4R^3$ (where $R^3$: H; F; Cl; $CF_3$; $OCF_3$; $OCHF_2$; lower alkyl; lower alkenyl; or lower alkoxy).

$R^{11}$ is H or lower alkyl;

$R^{12}$: H; lower alkyl; lower alkenyl; $-(CH_2)_oOR^{47}$ (where $R^{47}$: lower alkyl; or lower alkenyl); $-(CH_2)_oSR^{48}$ (where $R^{48}$: lower alkyl; or lower alkenyl); $-(CH_2)_oNR^{23}R^{24}$ (where $R^{23}$: lower alkyl; or lower alkenyl; $R^{24}$: H; or lower alkyl; or $R^{23}$ and $R^{24}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oOCONR^{50}R^{67}$ (where $R^{50}$: H; or lower alkyl; or lower alkenyl; $R^{67}$: lower alkyl; or $R^{50}$ and $R^{67}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oNR^{11}CONR^{51}R^{52}$ (where $R^{11}$: H; or lower alkyl; $R^{50}$: H; or lower alkyl; or lower alkenyl; $R^{81}$: H; or lower alkyl; or $R^{50}$ and $R^{51}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oN(R^{11})COR^{56}$ (where: $R^{11}$: H; or lower alkyl; $R^{56}$: lower alkyl; or lower alkenyl); $-(CH_2)_oCOOR^{49}$ (where $R^{49}$: lower alkyl; or lower alkenyl); $-(CH_2)_oCONR^{50}R^{51}$ (where $R^{50}$: lower alkyl; or lower alkenyl; and $R^{51}$: H; lower alkyl; or $R^{50}$ and $R^{51}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oPO(OR^{52})_2$ (where $R^{52}$: lower alkyl; or lower alkenyl); $(CH_2)_oSO_2R^{54}$ (where $R^{54}$: lower alkyl; or lower alkenyl); or $(CH_2)_qC_6H_4R^3$ (where $R^3$: H; F; Cl; $CF_3$; $OCF_3$; $OCHF_2$; lower alkyl; lower alkenyl; or lower alkoxy).

$R^{13}$: lower alkyl; lower alkenyl; $-(CH_2)_oOR^{47}$ (where $R^{47}$: lower alkyl; or lower alkenyl); $-(CH_2)_oSR^{48}$ (where $R^{48}$: lower alkyl; or lower alkenyl); $-(CH_2)_oNR^{23}R^{24}$ (where $R^{23}$: lower alkyl; or lower alkenyl; $R^{24}$: H; or lower alkyl; or $R^{23}$ and $R^{24}$ taken together form: $(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oOCONR^{50}R^{67}$ (where $R^{50}$: H; or lower alkyl; or lower alkenyl; $R^{67}$: lower alkyl; or $R^{50}$ and $R^{67}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oN(R^{11})COR^{56}$ (where: $R^{20}$: H; or lower alkyl; $R^{56}$: lower alkyl; or lower alkenyl); $-(CH_2)_oCOOR^{49}$ (where $R^{49}$: lower alkyl; or lower alkenyl); $-(CH_2)_oCONR^{50}R^{51}$ (where $R^{50}$: lower alkyl, or lower alkenyl; and $R^{51}$: H; lower alkyl; or $R^{50}$ and $R^{51}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oPO(OR^{52})_2$ (where $R^{52}$: lower alkyl; or lower alkenyl); $-(CH_2)_oSO_2R^{54}$ (where $R^{54}$: lower alkyl; or lower alkenyl); or $-(CH_2)_qC_6H_4R^3$ (where $R^3$: H; F; Cl; $CF_3$; $OCF_3$; $OCHF_2$; lower alkyl; lower alkenyl; or lower alkoxy).

$R^{14}$: H; lower alkyl; lower alkenyl; $-(CH_2)_oOR^{47}$ (where $R^{47}$: lower alkyl; or lower alkenyl); $-(CH_2)_oSR^{48}$ (where $R^{48}$: lower alkyl; or lower alkenyl); $-(CH_2)_oNR^{23}R^{24}$ (where $R^{23}$: lower alkyl; or lower alkenyl; $R^{24}$: H; or lower alkyl; or $R^{23}$ and $R^{24}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oOCONR^{50}R^{67}$ (where $R^{50}$: H; or lower alkyl; or lower alkenyl; $R^{67}$: lower alkyl; or $R^{50}$ and $R^{67}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oN(R^{11})COR^{56}$ (where: $R^{11}$: H; or lower alkyl; $R^{56}$: lower alkyl; or lower alkenyl); particularly favoured are $NR^{11}CO$ lower alkyl ($R^{11}$=H; or lower alkyl); $-(CH_2)_oCOOR^{49}$ (where $R^{49}$: lower alkyl; or lower alkenyl); $-(CH_2)_oCONR^{50}R^{51}$ (where $R^{50}$: lower alkyl, or lower alkenyl; and $R^{51}$: H; lower alkyl; or $R^{50}$ and $R^{51}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oPO(OR^{52})_2$ (where $R^{52}$: lower alkyl; or lower alkenyl); $-(CH_2)_oSO_2R^{54}$ (where $R^{54}$: lower alkyl; or lower alkenyl); or $-(CH_2)_qC_6H_4R^3$ (where $R^3$: H; F; Cl; $CF_3$; $OCF_3$; $OCHF_2$; lower alkyl; lower alkenyl; or lower alkoxy);

$R^{15}$ is $R^{11}$;

$R^{16}$ lower alkyl; lower alkenyl; $-(CH_2)_oOR^{47}$ (where $R^{47}$: lower alkyl; or lower alkenyl); $-(CH_2)_oSR^{48}$ (where $R^{48}$: lower alkyl; or lower alkenyl); $-(CH_2)_oNR^{23}R^{24}$ (where $R^{23}$: lower alkyl; or lower alkenyl; $R^{24}$: H; or lower alkyl; or $R^{23}$ and $R^{24}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oOCONR^{50}R^{67}$ (where $R^{50}$: H; or lower alkyl; or lower alkenyl; $R^{67}$: lower alkyl; or $R^{50}$ and $R^{67}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); $-(CH_2)_oN(R^{11})COR^{56}$ (where: $R^1$: H; or lower alkyl; $R^{56}$: lower alkyl; or lower alkenyl); particularly favoured are $NR^{20}CO$ lower alkyl ($R^{20}$=H; or lower alkyl); $-(CH_2)_oCOOR^{49}$ (where $R^{49}$: lower alkyl; or lower alkenyl); $-(CH_2)_oCONR^{50}R^{51}$ (where $R^{50}$: lower alkyl, or lower alkenyl; and $R^{51}$: H; lower alkyl; or $R^{50}$ and $R^{51}$ taken together form: $-(CH_2)_{2-6}-$; $-(CH_2)_2O(CH_2)_2-$; $-(CH_2)_2S(CH_2)_2-$; or $-(CH_2)_2NR^{49}(CH_2)_2-$; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; $OCF_3$; $OCHF_2$; lower alkyl; lower alkenyl; or lower alkoxy);

$R^{17}$: H; lower alkyl; lower alkenyl; —$(CH_2)_mOR^{47}$ (where $R^{47}$: lower alkyl; or lower alkenyl); —$(CH_2)_mNR^{17}R^{23}$ (where $R^{17}$: lower alkyl; or lower alkenyl; $R^{23}$: H; or lower alkyl; or $R^{17}$ and $R^{23}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mOCONR^{50}R^{67}$ (where $R^{50}$: H; or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mN(R^{11})COR^{11}$ (where: $R^{20}$: H; or lower alkyl; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl; or lower alkenyl; and $R^{51}$: H; lower alkyl; or $R^{50}$ and $R^{51}$ taken together form: —$(CH_2)_{2-6}$—; —$(CH_2)_2S(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; $OCF_3$; $OCHF_2$ lower alkyl; lower alkenyl; or lower alkoxy).

$R^{18}$: H; lower alkyl; lower alkenyl; —$(CH_2)_mOR^{47}$ (where $R^{47}$: lower alkyl; or lower alkenyl); —$(CH_2).NR^{23}R^{24}$ (where $R^{23}$: lower alkyl; or lower alkenyl; $R^{23}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mOCONR^{50}R^{67}$ (where $R^{50}$: H; or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; or —$(CH_2)_2NR^{49}(CH_2)_2$—; where $R^{49}$: H; or lower alkyl); —$(CH_2)_mNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mN(R^{11})COR^{56}$ (where: $R^{11}$: H; or lower alkyl; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl; or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; $OCF_3$; $OCHF_2$ lower alkyl; lower alkenyl; or lower alkoxy).

$R^{19}$: H; lower alkyl; lower alkenyl; —$(CH_2)_mOR^{47}$ (where $R^{47}$: lower alkyl; or lower alkenyl); —$(CH_2).NR^{23}R^{24}$ (where $R^{17}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mOCONR^{50}R^{67}$ (where $R^{50}$: H; or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; or —$(CH_2)_2NR^{49}(CH_2)_2$—; where $R^{49}$: H; or lower alkyl); —$(CH_2)_mNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mN(R^{11})COR^{56}$ (where: $R^{11}$: H; or lower alkyl; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl; or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; $OCF_3$; $OCHF_2$; lower alkyl; lower alkenyl; or lower alkoxy).

Alternatively, $R^{18}$ and $R^{19}$ taken together can be —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl).

$R^{20}$ is $R^{14}$;

For templates (b) to (s), such as (b1) and (c1), the preferred values for the various symbols are the following:

$R^3$: H; F; Cl; $CF_3$; lower alkyl; lower alkenyl; —$(CH_2)_oOR^{47}$ (where $R^{47}$: lower alkyl; or lower alkenyl); —$(CH_2)_oSR^{48}$ (where $R^{48}$: lower alkyl; or lower alkenyl); —$(CH_2)_oNR^{23}R^{24}$ (where $R^{23}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oOCONR^{50}R^{67}$ (where $R^{50}$: H; or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oNR^{11}CONR^{50}R^{51}$ (where $R^{11}$: H; or lower alkyl; $R^{50}$: H; or lower alkyl; or lower alkenyl; $R^{82}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oN(R^{11})COR^{56}$ (where: $R^{11}$: H; or lower alkyl; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl; or lower alkenyl; and $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; $OCF_3$; $OCHF_2$; lower alkyl; lower alkenyl; or lower alkoxy).

$R^{11}$: H; or lower alkyl.

$R^{21}$: H; lower alkyl; lower alkenyl; —$(CH_2)_pOR^{47}$ (where $R^{47}$: lower alkyl; or lower alkenyl); —$(CH_2)_pNR^{23}R^{24}$ (where $R^{23}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pOCONR^{50}R^{67}$ (where $R^{50}$: H;

or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pNR^{11}CONR^{50}R^{51}$ (where H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pN(R^{11})COR^{56}$ (where: $R^{11}$: H; or lower alkyl; $R^{56}$: lower alkyl; or lower alkenyl); —$(CH_2)_oCOOR^{49}$ (where $R^{49}$: lower alkyl; or lower alkenyl); (—$CH_2)_oCONR^{50}R^{51}$ (where $R^{50}$: lower alkyl, or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_rC_6H_4R^3$ (where $R^3$: H; F; Cl; $CF_3$; $OCF_3$; $OCHF_2$; lower alkyl; lower alkenyl; or lower alkoxy); most preferred is —$CH_2CONR^{50}R^{51}$ ($R^{50}$: H; or lower alkyl; $R^{51}$: lower alkyl; or lower alkenyl).

$R^{22}$: H, methyl.

$R^{23}$: H; lower alkyl; lower alkenyl; —$(CH_2)_mOR^{47}$ (where $R^{47}$: lower alkyl; or lower alkenyl); —$(CH_2)_mNR^{23}R^{24}$ (where $R^{23}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); $(CH_2)_mOCONR^{50}R^{67}$ (where $R^{50}$: lower alkyl; or lower alkenyl; $R^{67}$: H; or lower alkyl; or $R^{50}$ and $R^{67}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mN(R^{11})COR^{56}$ (where: $R^{11}$: H; or lower alkyl; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl, or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl).

$R^{24}$: H; or lower alkyl.

$R^{25}$: H; lower alkyl; lower alkenyl; —$(CH_2)_mOR^{47}$ (where $R^{47}$: lower alkyl; or lower alkenyl); —$(CH_2)_mNR^{23}R^{24}$ (where $R^{23}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mOCONR^{50}R^{67}$ (where $R^{50}$: H; or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mN(R^{11})COR^{56}$ (where: $R^{11}$: H; or lower alkyl; $R^{56}$: lower alkyl; or lower alkenyl); —$(CH_2)_o$ $COOR^{49}$ (where $R^{49}$: lower alkyl; or lower alkenyl); —$(CH_2)_oCONR^{50}R^{51}$ (where $R^{50}$: lower alkyl; or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; lower alkyl); or $(CH_2)_pC_6H_4R^3$ (where $R^3$: H; F; Cl; $CF_3$; $OCF_3$; $OCHF_2$; lower alkyl; lower alkenyl; or lower alkoxy).

$R^{26}$: lower alkyl; lower alkenyl; aryl-lower alkyl; or$(CH_2)_pC_6H_4R^3$ (where $R^3$: H; F; Cl; $CF_3$; $OCF_3$; $OCHF_2$; lower alkyl; lower alkenyl; or lower alkoxy).

$R^{27}$: H; lower alkyl; lower alkenyl; —$(CH_2)_pOR^{47}$ (where $R^{47}$: lower alkyl; or lower alkenyl); —$(CH_2)_pNR^{23}R^{24}$ (where $R^{23}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pOCONR^{50}R^{67}$ (where $R^{50}$: H; or lower alkyl; or lower alkenyl; $R^{67}$: lower alkyl; or $R^{50}$ and $R^{67}$ taken together folio: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pN(R^{11})COR^{56}$ (where: $R^H$: H; or lower alkyl; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl, or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; $OCF_3$; $OCHF_2$; lower alkyl; lower alkenyl; or lower alkoxy).

$R^{28}$: H; lower alkyl; lower alkenyl; —$(CH_2)_pOR^{47}$ (where $R^{47}$: lower alkyl; or lower alkenyl); —$(CH_2)_pNR^{23}R^{24}$ (where $R^{23}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pOCONR^{50}R^{67}$ (where $R^{50}$: H; or lower alkyl; or lower alkenyl; $R^{67}$: lower alkyl; or $R^{17}$ and $R^{78}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{52}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pN(R^{11})COR^{56}$ (where: $R^{11}$: H; or lower alkyl; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl, or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; lower alkyl; lower alkenyl; or lower alkoxy).

$R^{29}$: H; lower alkyl; lower alkenyl; $OCF_3$; $OCHF_2$; aryl-lower alkyl.

$R^{30}$: lower alkyl; lower alkenyl; or aryl-lower alkyl.

$R^{31}$: H; lower alkyl; lower alkenyl; —$(CH_2)_pOR^{47}$ (where $R^{47}$: lower alkyl; or lower alkenyl); —$(CH_2)_pNR^{23}R^{24}$ (where $R^{23}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pOCONR^{50}R^{67}$ (where $R^{50}$: H; or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pN(R^{11})COR^{56}$ (where: $R^{11}$: H; or lower alkyl; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl, or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; $OCF_3$; $OCHF_2$; lower alkyl; lower alkenyl; or lower alkoxy).

$R^{32}$: H; lower alkyl; lower alkenyl; —$(CH_2)_pOR^{47}$ (where $R^{47}$: lower alkyl; or lower alkenyl); —$(CH_2)_pNR^{23}R^{24}$ (where $R^{23}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_pOCONR^{50}R^{67}$ (where $R^{50}$: H; or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); $(CH_2)_pNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_3$—; or —$(CH_2)_2NR^{49}(CH_2)_2$—; where $R^{49}$: H; or lower alkyl); —$(CH_2)_pN(R^{11})COR^{56}$ (where: $R^{11}$: H; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl, or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; $OCF_3$; $OCHF_2$; lower alkyl; lower alkenyl; or lower alkoxy).

$R^{33}$: H; lower alkyl; lower alkenyl; —$(CH_2)_mOR^{47}$ (where $R^{47}$: lower alkyl; or lower alkenyl); —$(CH_2)_mSR^{48}$ (where $R^{48}$: lower alkyl; or lower alkenyl); —$(CH_2)$.$NR^{23}R^{24}$ (where $R^{23}$: lower alkyl; or lower alkenyl; $R^{24}$: H; or lower alkyl; or $R^{23}$ and $R^{24}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mOCONR^{50}R^{67}$ (where $R^{50}$: H; or lower alkyl; or lower alkenyl; $R^{67}$: lower alkyl; or $R^{50}$ and $R^{67}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_mNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)$.$N(R^{11})COR^{56}$ (where: $R^{11}$: H; or lower alkyl; $R^{56}$: lower alkyl; or lower alkenyl); —$(CH_2)_oCOOR^{49}$ (where $R^{49}$: lower alkyl; or lower alkenyl); —$(CH_2)_oCONR^{50}R^{51}$ (where $R^{50}$: lower alkyl; or lower alkenyl; and $R^{51}$: H; lower alkyl; or $R^{50}$ and $R^{51}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); —$(CH_2)_oPO(OR^{52})_2$ (where $R^{52}$: lower alkyl; or lower alkenyl); —$(CH_2)_oSO_2R^{54}$ (where $R^{54}$: lower alkyl; or lower alkenyl); or —$(CH_2)_qC_6H_4R^3$ (where $R^3$: H; F; Cl; $CF_3$; $OCF_3$; $OCHF_2$; lower alkyl; lower alkenyl; or lower alkoxy).

$R^{34}$: H; lower alkyl; lower alkenyl; or —$(CH_2)_oC_6H_4R^3$ (where $R^3$: H; F; Cl; $CF_3$; $OCF_3$; $OCHF_2$; lower alkyl; lower alkenyl; or lower alkoxy).

$R^{35}$ is $R^{34}$.

$R^{36}$: H; $(CH_2)oOR^{47}$ (where $R^{47}$: lower alkyl; or lower alkenyl); —$(CH_2)_oC_6H_4R^3$ (where $R^3$: H; F; Cl; $CF_3$; $OCF_3$; $OCHF_2$; lower alkyl; lower alkenyl; or lower alkoxy).

$R^{37}$ is $R^{34}$.

$R^{38}$ is $R^{34}$.

$R^{39}$ is $R^{34}$.

$R^{40}$ is $R^{34}$.

$R^{41}$ is $R^{34}$.

$R^{42}$: H; $(CH_2)oOR^{47}$ (where $R^{47}$: lower alkyl; or lower alkenyl);

$R^{43}$ is $R^{17}$.

$R^{44}$ is $R^{17}$.

$R^{45}$ is $R^{12}$.

$R^{46}$: H; lower alkyl; —$(CH_2)_oCOOR^{49}$ (where $R^{49}$: lower alkyl; or lower alkenyl); —$(CH_2)_oCONR^{50}R^{51}$ (where $R^{50}$: lower alkyl; or lower alkenyl; and $R^{51}$: H; lower alkyl; or $R^{50}$ and $R^{31}$ taken together form: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); or $(CH_2)_sC_6H_4R^3$ (where $R^3$: H; F; Cl; $CF_3$; $CF_3$; $OCF_3$; $OCHF_2$; lower alkyl; lower alkenyl; or lower alkoxy).

Among the building blocks A34 to A68 the following are preferred: A38 with $R^{22}$ being H, A39, A40, A41 with $R^{22}$ being H, A42 and A43.

The building block —B—CO— within templates (a1) and (a2) designates an L-amino acid residue. Preferred values for B are enantiomers of groups A2 with $R^2$ being H. and A 12 with $R^3$ being H. Most preferred are

| | |
|---|---|
| Tic | L-3-amino-1,2,3,4-tetrahydroisoquinoline-3-carboxylic acid; and |
| Azt | L-azetidine-2-carboxylic acid |

The peptidic chain Z of the β-hairpin mimetics described herein is generally defined in terms of amino acid residues belonging to one of the following groups:

| | | |
|---|---|---|
| Group C | —NR$^{11}$CH(R$^{64}$)CO—; | "hydrophobic: small to medium-sized" |
| Group D | —NR$^{11}$CH(R$^{65}$)CO—; | "hydrophobic: large aromatic or heteroaromatic" |
| Group E | —NR$^{11}$CH(R$^{66}$)CO—; | "polar-cationic" and "urea-derived" |
| Group F | —NR$^{11}$CH(R$^{76}$)CO—; | "polar-non-charged or anionic" |

Furthermore, Gly can also be an amino acid residue in chain Z.

Group C comprises amino acid residues with small to medium-sized hydrophobic side chain groups according to the general definition for substituent R$^{64}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized amino acids include alanine, isoleucine, leucine, methionine and valine.

Group D comprises amino acid residues with aromatic and heteroaromatic side chain groups according to the general definition for substituent R$^{65}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl- or aryl phosphonates- and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent R$^{69}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl- or aryl phosphonates- and phosphates or tertiary amines. Genetically encoded heteroaromatic amino acids include tryptophan and histidine.

Group E comprises amino acids containing side chains with polar-cationic (e.g. amino, guanidino, amidino and, acylamino-derived residues according to the general definition for substituent R$^{66}$. Polar-cationic refers to a basic side chain which is protonated at physiological pH. Genetically encoded polar-cationic amino acids include arginine, lysine, and histidine.

Group F comprises amino acids containing side chains with polar-non-charged or anionic residues according to the general definition for substituent R$^{76}$. A polar-non-charged or anionic residue refers to a hydrophilic side chain that is uncharged and, respectively anionic at physiological pH (carboxylic acids being included), but that is not repelled by aqueous solutions. Such side chains typically contain hydrogen bond donor groups such as (but not limited to) primary and secondary amides, carboxylic acids and esters, primary and secondary amines, thiols, alcohols, phosphonates, phosphates, ureas or thioureas. Citrulline is an example for an urea derived amino acid residue. These groups can form hydrogen bond networks with water molecules. In addition they may also contain hydrogen bond acceptor groups such as (but not limited to) ethers, thioethers, esters, tetriary amides, carboxylic acids and carboxylates, alkyl- or aryl phosphonates- and phosphates or tertiary amines. Genetically encoded polar-non-charged amino acids include asparagine, cysteine, glutamine, serine and threonine, but also aspartic acid, glutamic acid, and citrulline.

Most preferred amino acid residues in chain Z are those derived from natural α-amino acids. Hereinafter follows a list of amino acids which, or the residues of which, are suitable for the purposes of the present invention, the abbreviations corresponding to generally adopted usual practice:

| three letter code | | one letter code |
|---|---|---|
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |
| Pro | L-Proline | P |
| $^D$Pro | D-Proline | $^D$P |
| Ser | L-Serine | S |
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:

| | |
|---|---|
| Cit | L-Citrulline |
| Orn | L-Ornithine |
| tBuA | L-t-Butylalanine |
| Sar | Sarcosine |
| Pen | L-Penicillamine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC (NH$_2$)=NH) | L-meta-Guanidinophenylalanine |
| Phe(pNHC (NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |

-continued

| | |
|---|---|
| 2Cl-Phe | L-2-Chlorophenylalanine |
| 3,4Cl₂-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | 1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | N-Acetyllysine |
| Dpr | 2,3-Diaminopropionic acid |
| A₂Bu | 2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-(4-phenyl)phenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| 4-AmPyrr1 | (2S,4S)-4-Amino-pyrrolidine-L-carboxylic acid |
| 4-AmPyrr2 | (2S,4R)-4-Amino-pyrrolidine-L-carboxylic acid |
| 4-PhePyrr1 | (2S,5R)-4-Phenyl-pyrrolidine-L-carboxylic acid |
| 4-PhePyrr2 | (2S,5S)-4-Phenyl-pyrrolidine-L-carboxylic acid |
| 5-PhePyrr1 | (2S,5R)-5-Phenyl-pyrrolidine-L-carboxylic acid |
| 5-PhePyrr2 | (2S,5S)-5-Phenyl-pyrrolidine-L-carboxylic acid |
| Pro(4-OH)1 | (4S)-L-Hydroxyproline |
| Pro(4-OH)2 | (4R)-L-Hydroxyproline |
| Pip | L-Pipecolic acid |
| ᴰPip | D-Pipecolic acid |
| OctG | L-Octylglycine |
| NGly | N-Methylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |
| DimK | L-(N',N'Dimethyl)-lysine |
| Lpzp | L-Piperazinic acid |
| Dpzp | D-Piperazinic acid |
| Isorn | L-(N',N'-diisobutyl)-ornithine |
| PipAla | L-2-(4'-piperidinyl)-alanine |
| PirrAla | L-2-(3'-pyrrolidinyl)-alanine |
| Ampc | 4-Amino-piperidine-4-carboxylic acid |
| NMeR | L-N-Methylarginine |
| NMeK | L-N-Methyllysine |
| NMePhe | L-N-Methylphenylalanine |
| BnG | N-Benzylglycine |
| (4-OH)BnG | N-4-Hydroxy-benzylglycine |
| IaG | N-Isoamylglycine |
| IbG | N-Isobutlyglycine |
| Azt | L-azetidine-2-carboxylic acid |

Particularly preferred residues for group C are:

| | |
|---|---|
| Ala | L-Alanine |
| Ile | L-Isoleucine |
| Leu | L-Leucine |
| Met | L-Methionine |
| Val | L-Valine |
| tBuA | L-t-Butylalanine |
| t-BuG | L-tert.-Butylglycine |
| Cha | L-Cyclohexylalanine |
| C₄al | L-3-Cyclobutylalanine |
| C₅al | L-3-Cyclopentylalanine |
| Nle | L-Norleucine |
| hCha | L-Homo-cyclohexylalanine |
| OctG | L-Octylglycine |

-continued

| | |
|---|---|
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |
| Azt | L-azetidine-2-carboxylic acid |

Particularly preferred residues for group D are:

| | |
|---|---|
| His | L-Histidine |
| Phe | L-Phenylalanine |
| Trp | L-Tryptophan |
| Tyr | L-Tyrosine |
| Phg | L-Phenylglycine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl₂-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Thi | L-β-2-Thienylalanine |
| Tza | L-2-Thiazolylalanine |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hPhe | L-Homo-phenylalanine |
| Bpa | L-4-Benzoylphenylalanine |
| PirrAla | L-2-(3'-pyrrolidinyl)-alanine |
| NMePhe | L-N-Methylphenylalanine |
| 4-PyrAla | L-2-(4'Pyridyl)-alanine |

Particularly preferred residues for group E are

| | |
|---|---|
| Arg | L-Arginine |
| Lys | L-Lysine |
| Orn | L-Ornithine |
| Dpr | L-2,3-Diaminopropionic acid |
| A₂Bu | L-2,4-Diaminobutyric acid |
| Dbu | (S)-2,3-Diaminobutyric acid |
| Phe(pNH₂) | L-para-Aminophenylalanine |
| Phe(mNH₂) | L-meta-Aminophenylalanine |
| Phe(oNH₂) | L-ortho-Aminophenylalanine |
| hArg | L-Homo-arginine |
| Phe(mC(NH₂)=NH) | L-meta-Amidinophenylalanine |
| Phe(pC(NH₂)=NH) | L-para-Amidinophenylalanine |
| Phe(mNHC (NH₂)=NH) | L-meta-Guanidinophenylalanine |
| Phe(pNHC (NH₂)=NH) | L-para-Guanidinophenylalanine |
| DimK | L-(N',N'Dimethyl)-lysine |
| Isorn | L-(N',N'-diisobutyl)-ornithine |
| NMeR | L-N-Methylarginine |
| NMeK | L-N-Methyllysine |
| OrnPyr | L-2-Amino-5-[(2'carbonylpyrazine)]amino-pentanoic |
| PipAla | L-2-(4'-piperidinyl)-alanine |

Particularly preferred residues for group F are

| | |
|---|---|
| Asn | L-Asparagine |
| Asp | L-Aspartic acid |
| Cys | L-Cysteine |
| Gln | L-Glutamine |
| Glu | L-Glutamic acid |
| Ser | L-Serine |
| Thr | L-Threonine |

-continued

| | |
|---|---|
| Cit | L-Citrulline |
| Pen | L-Penicillamine |
| AcLys | L-N$^\varepsilon$-Acetyllysine |
| hCys | L-Homo-cysteine |
| hSer | L-Homo-serine |

Generally, the peptidic chain Z within the β-hairpin mimetics of the invention comprises 4 amino acid residues. The positions P1 to P4 of each amino acid residue in the chain Z are unequivocally defined as follows: P1 represents the first amino acid in the chain Z that is coupled with its N-terminus to the C-terminus of the templates (b)-(s), or of group —B—CO— in template (a1), or of group -A-CO— in template (a2); and P4 represents the last amino acid in the chain Z that is coupled with its C-terminus to the N-terminus of the templates (b)-(s), or of group -A-CO— in template (a1), or of group —B—CO— in template (a2), Each of the positions P1 to P4 will contain an amino acid residue belonging to one of the above types C D, E, F, or being Gly, as follows:

The α-amino acid residues in positions 1 to 4 of the chain Z are preferably:

P1: of type C, or of type D or of type E or of type F or the residue is Gly;
P2: of type D or of type E or of type C or the residue is Gly;
P3: of type D or of type E or the residue is Gly;
P4: of type C, or of type D or of type E or of type F, or the residue is Gly;

at P2 and P3 also D-isomers being possible.

The α-amino acid residues in positions 1 to 4 are most preferably:

| | |
|---|---|
| P1: | Phe, Ile, Gln, Thr, Trp, Glu, Tyr; |
| P2: | Trp, Lys, $^D$Val; |
| P3: | Lys, Tyr, Arg, Trp; |
| P4: | Tyr, His, Gly, Ala, Orn, Lys; |

Particularly preferred β-peptidomimetics of the invention include those described in Examples 2 and 15.

The processes of the invention can advantageously be carried out as parallel array syntheses to yield libraries of template-fixed β-hairpin peptidomimetics of the above general formula I. Such parallel syntheses allow one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, preferably 1-5%, divinylbenzene; polystyrene coated with polyethyleneglycol spacers (Tentagel$^R$); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (Rink H, *Tetrahedron Lett.* 1987, 28, 3783-3790). Linkers of this kind form amides of the carboxyl group of the amino acids; examples of resins functionalized by such linker structures include 4-[(((2,4-dimethoxyphenyl) Fmoc-aminomethyl)phenoxyacetamido)aminomethyl] PS resin, 4-[(((2,4-dimethoxyphenyl)Fmoc-aminomethyl)phenoxyacetamido)aminomethyl]-4-methylbenzydrylamine PS resin (Rink amide MBHA. PS Resin), and 4-[(((2,4-dimethoxyphenyl)Fmoc-aminomethyl)phenoxyacetamido) aminomethyl]benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl) Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin$^R$ linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the processes of the invention can be advantageously carried out as described herein below but it will be immediately apparent to those skilled in the art how these procedures will have to be modified in case it is desired to synthesize one single compound of the above formula I.

A number of reaction vessels (normally 24 to 192, typically 96) equal to the total number of compounds to be synthesized by the parallel method are loaded with 25 to 1000 mg, preferably 100 mg, of the appropriate functionalized solid support which is preferably derived from polystyrene cross-linked with 1 to 3% of divinylbenzene, or from Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin$^R$ linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the processes of the invention include the super acid labile 4-(2,4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e.g. also in the side-chain of lysine)

| | |
|---|---|
| Cbz | benzyloxycarbonyl |
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Trt | triphenymethyl or trityl | for the carboxyl group (as is present e.g. also in the side-chain of aspartic and glutamic acid) by conversion into esters with the alcohol components

| | |
|---|---|
| tBu | tert.-butyl |
| Bn | benzyl |
| Me | methyl |
| Ph | phenyl |
| Pac | Phenacyl |
| | Allyl |
| Tse | trimethylsilylethyl |
| Tce | trichloroethyl; | for the guanidino group (as is present e.g. in the side-chain of arginine)

| | |
|---|---|
| Pmc | 2,2,5,7,8-pentamethylchroman-6-sulfonyl |
| Ts | tosyl (i.e. p-toluenesulfonyl) |
| Cbz | benzyloxycarbonyl |
| Pbf | 2,2,4,6,7-pentamethyldihydrobenzofuran-5-sulfonyl | for the hydroxy group (as is present e.g. in the side-chain of threonine and serine)

| | |
|---|---|
| tBu | tert.-butyl |
| Bn | benzyl |
| Trt | trityl | and for the mercapto group (as is present e.g. in the side-chain of cysteine)

| | |
|---|---|
| Acm | acetamidomethyl |
| tBu | tert.-butyl |
| Bn | benzyl |
| Trt | trityl |
| Mtr | 4-methoxytrityl. |

The 9-fluorenylmethoxycarbonyl-(Fmoc)-protected amino acid derivatives are preferably used as the building blocks for the construction of the template-fixed β-hairpin loop mimetics of formula I. For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, Castro et al., *Tetrahedron Lett.* 1975, 14, 1219-1222; *Synthesis,* 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-) 1,1,3,3-tetramethyluronium tetrafluoroborate (TBTU), or hexafluorophosphate (HBTU, Knorr et al., *Tetrahedron Lett.* 1989, 30, 1927-1930); these phosphonium and uronium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s).

Washing procedures are repeated up to about 50 times (preferably about 10 times), monitoring the efficiency of reagent, solvent, and by-product removal by methods such as TLC, GC, LC-MS or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

After detachment of the fully protected linear peptide from the solid support the individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefor. The aqueous layer is collected and evaporated to dryness, and the fully deprotected cyclic peptide derivative of formula I is obtained as end-product.

Depending on its purity, this peptide derivative can be used directly for biological assays, or it has to be further purified, for example by preparative HPLC.

As mentioned earlier, it is thereafter possible, if desired, to convert a fully deprotected product of formula I thus obtained into a pharmaceutically acceptable salt or to convert a pharmaceutically acceptable, or unacceptable, salt thus obtained into the corresponding free compound of formula I or into a different, pharmaceutically acceptable, salt. Any of these operations can be carried out by methods well known in the art.

The starting materials used in the process of the invention, pre-starting materials therefore, and the preparation of these starting and pre-starting materials will now be discussed in detail.

Building blocks of type A can be synthesized according to the literature methods described below. The corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron (Report)* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press, Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163-1179; R. M. Williams, "Synthesis of optically active α-amino acids", *Tetrahedron Organic Chemistry Series*, Vol. 7, J. E. Baldwin, P. D. Magnus (Eds.), Pergamon Press, Oxford 1989, Chapter 7, p. 257-2'79). Hydrolytic enzymes involve hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press, Oxford 1989).

Building blocks A1 through A 17 and their preparation have been described previously, as indicated in the following table:

| Building block as mentioned herein | Preparation, including starting and pre-starting materials as described in International Application PCT/EP02/01711 of the same applicants, published as WO 02/070547 |
|---|---|
| A1 | A1 |
| A2 | A2 |
| A3 | A3 |
| A4 | A4 |
| A5 | A12 |
| A6 | A13 |
| A7 | A14 |
| A8 | A19 |
| A9 | A29 |
| A10 | A30 |
| A11 | A31 |
| A12 | A32 |
| A13 | A33 |
| A14 | A34 |
| A15 | A35 |
| A16 | A36 |
| A17 | A37 |

A18: See B. A. Steinbaugh, H. W. Hamilton, W. C. Patt, S. T. Rundalo, B. L. Batley, E. A. Lunney, M. J. Ryan, G H. W. Hicks, *Bioorg. Meet. Chem. Lett.* 1994, 4, 2023-8.

A19: See synthesis described in Scheme 1. Starting materials such as 1 can be prepared according to: M. L. Bennasar, A. Torrens, M. Rubiralta, J. Bosch, D. S. Grierson, H.-P. Husson, *Heterocycles* 1989, 29, 745-60.

Scheme 1

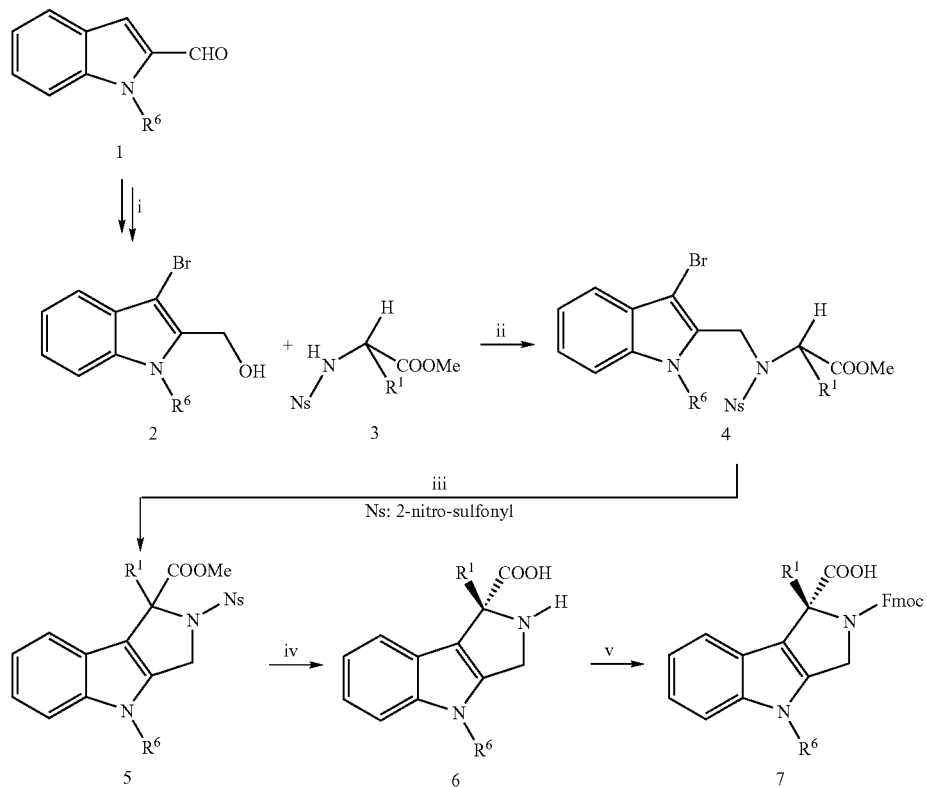

i: NBS, CH$_2$Cl$_2$; then NaBH$_4$, MeOH; ii: DIAD, PPh$_3$, THF; iii: tBuONa, [Pd(dba)$_2$], 2,2'-bis(diphenyl-phosphanyl)-1,1'-binaphthalene (BINAP), dioxane, 95-100° (see R. Freund et al. Helv. Chim. Acta 2000, 83, 1247-1255); iv: resolution (e.g. lipase); then Cs$_2$CO$_3$, PhSH, CH$_3$CN; v: FmocOSu, Na$_2$CO$_3$, H$_2$O, dioxane A20: See synthesis described in Scheme 2. Starting materials such as 8 can be prepared according to: M. Somei, S. Sayama, K. Naka, F. Yamada, *Heterocycles* 1988, 27, 1585-7. For the Pd-catalyzed cyclization of N-substituted 3-bromo-indoles see: H. Zhang, R. C. Larock, *J. Org. Chem.* 2002, 67, 7048-56; ibid, *Org. Lett.* 2002, 4, 3035-38.

Scheme 2

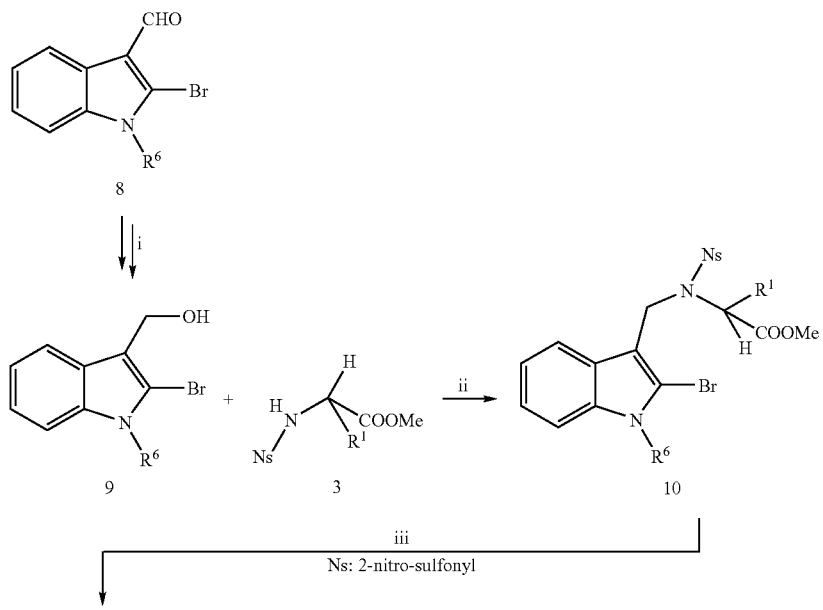

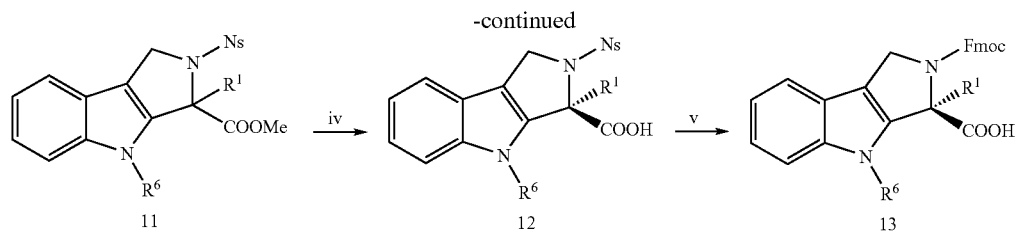

i: NaBH$_4$, MeOH; ii: DIAD, PPh$_3$, THF; iii: tBuONa, [Pd(dba)$_2$, 2,2′−bis(diphenyl-phosphanyl)-1,1′-binaphthalene (BINAP), dioxane, 95-100° (see R. Freund et al. Helv. Chim. Acta 2000, 83, 1247-1255);
iv: resolution (e.g. lipase or esterase); then Cs$_2$CO$_3$, PhSH, CH$_3$CN; v: FmocOSu, Na$_2$CO$_3$, H$_2$O, dioxane A21: See synthesis described in Scheme 3.

Scheme 3

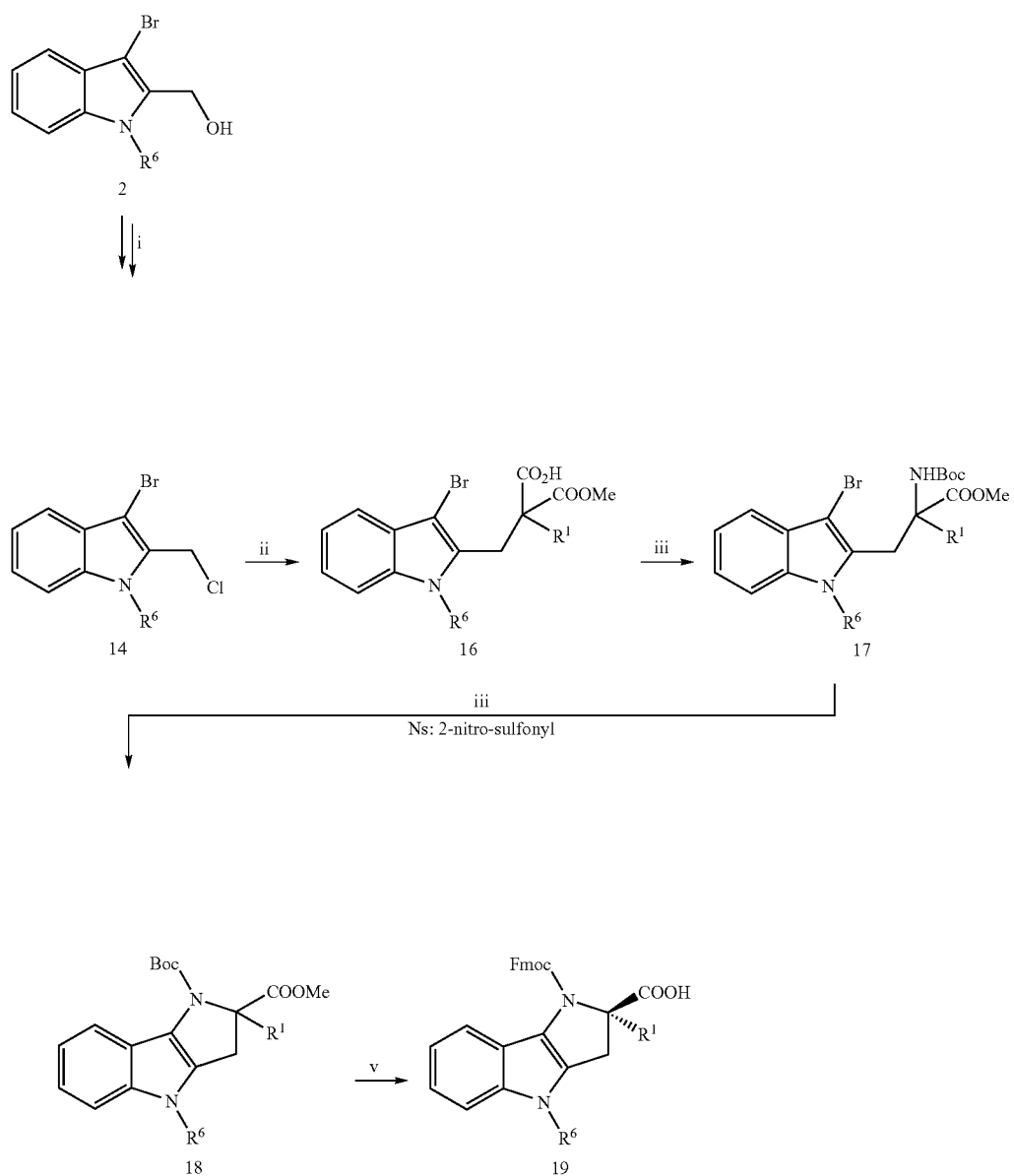

Ns: 2-nitro-sulfonyl i: CCl$_4$, THF, PPh$_3$; ii: NaH, CHR$^1$(COOMe)COOSiMe$_3$ (15), THF; iii: DPPA, tBuOH, toluene;
iv: tBuONa, [Pd(dba)$_2$, 2,2′−bis(diphenyl-phosphanyl)-1,1′-binaphthalene (BINAP), dioxane;
v: resolution (e.g. lipase or esterase); then TFA, CH$_2$Cl$_2$, H$_2$O;
then FmocOSu, Na$_2$CO$_3$, H$_2$O, dioxane Building blocks A22 through A66 and their preparation have been described previously, as indicated in the following table:

| Building block as mentioned herein | Preparation, including starting and pre-starting materials as described in International Application PCT/EP02/01711 of the same applicants, published as WO 02/070547 |
|---|---|
| A22 | A58 |
| A23 | A59 |
| A24 | A60 |
| A25 | A61 |
| A26 | A62 |
| A27 | A63 |
| A28 | A64 |
| A29 | A65 |
| A30 | A66 |
| A31 | A67 |
| A32 | A68 |
| A33 | A69 |
| A34 | A70 |
| A35 | A71 |
| A36 | A72 |
| A37 | A73 |
| A38 | A74 |
| A39 | A75 |
| A40 | A76 |
| A41 | A77 |
| A42 | A78 |
| A43 | A79 |
| A44 | A80 |
| A45 | A81 |
| A46 | A82 |
| A47 | A83 |
| A48 | A84 |
| A49 | A85 |
| A50 | A86 |
| A51 | A87 |
| A52 | A88 |
| A53 | A89 |
| A54 | A90 |
| A55 | A91 |
| A56 | A92 |
| A57 | A93 |
| A58 | A94 |
| A59 | A95 |
| A60 | A96 |
| A61 | A97 |
| A62 | A98 |
| A63 | A99 |
| A64 | A100 |
| A65 | A101 |
| A66 | A102 |

A67: Compounds of this type can be prepared starting from the corresponding 4-hydroxy-β-tetralones and subsequent oxidation of the alcohol with e.g. $MnO_2$ according to general method described in International Application PCT/EP02/01711 of the same applicants, published as WO 02/070547 A1 (Scheme 28)

A68: Compounds of this type can be prepared starting from the corresponding N-substituted tetrahydroquinoline-3-ones according to general method described in International Application PCT/EP02/01711 of the same applicants, published as WO 02/070547 A1 (Scheme 28).

A69: See C. J. Blankley, J. S. Kaltenbronn, D. E. DeJohn, A. Werner, L. R. Bennett, G. Bobowski, U. Krolls, D. R. Johnson, W. M. Pearlman, M. L. Hoefle, A. D. Essenburg, D. M. Cohen, H. R. Kaplan, *J. Med. Chem.* 1987, 30, 992-8. See Beilstein Registry Number 6054327.

A70: The preparation of these starting and pre-starting materials are described in International Application PCT/EP02/01711 of the same applicants, published as WO 02/070547 A1 (A5).

A71: The preparation of these starting and pre-starting materials are described in International Application PCT/EP02/01711 of the same applicants, published as WO 02/070547 A1 (A8).

Templates of type (b1): The preparation of these starting and pre-starting materials are described in International Application PCT/EP02/01711 of the same applicants, published as WO 02/070547 A1 (b1).

Templates of type (b2): The preparation of these starting and pre-starting materials are described in International Application PCT/EP02/01711 of the same applicants, published as WO 02/070547 A1 (b2).

Templates of type (c1): The preparation of these starting and pre-starting materials are described in International Application PCT/EP02/01711 of the same applicants, published as WO 02/070547 A1 (c1).

Templates of type (c2): The preparation of these starting and pre-starting materials are described in International Application PCT/EP02/01711 of the same applicants, published as WO 02/070547 A1 (c2).

Templates of type (c3): The preparation of these starting and pre-starting materials are described in International Application PCT/EP02/01711 of the same applicants, published as WO 02/070547 A1 (c3).

Templates (d1) can be prepared according to: J. E. Baldwin, R. T. Freedman, Ch. Lowe, Ch. Schofield, E. Lee, *Tetrahedron*, 1989, 45, 4537-4550; M. Angiolini, S Araneo, L. Belvisi, E. Cesarotti, A. Checca, L. Crippa, L. Manzoni, C. Scolastico, *Eur. J. Org. Chem.* 2000, 2571-2581; M. Shimizu, H. Nemoto, H. Kakuda, H. Takahata, *Heterocycles*, 2003, 59, 245-255; D. S. Karanewsky, X. Bai, S. T. Linton, J. F. Krebs, J. Wu, B. Pham, K. J. Tomaselli, *Bioorg. Med. Chem. Lett.* 1998, 8, 2557-2762.

Templates (d2) can be prepared according to: C. Xiong, J. Zhang, P. Davies, W. Wang, J. Ying, F. Porreca, V. J. Hruby, *J. Chem. Soc. Chem. Commun.* 2003, 1598-99; J. E. Baldwin, R. T. Freedman, Ch. Lowe, Ch. Schofield, E. Lee, *Tetrahedron*, 1989, 45, 4537-4550; P. W. Baures, W. H. Ojala, W. J. Costain, M. C. Ott, A. Pradhan, W. B. Gleason, R. K. Mishra, R. L. Johnson, *J. Med. Chem.* 1997, 40, 3594-3600; D. S. Karanewsky, X. Bai, S. T. Linton, J. F. Krebs, J. Wu, B. Pham, K. J. Tomaselli, *Bioorg. Med. Chem. Lett.* 1998, 8, 2557-2762; Templates of type (d3) can be prepared according to: W. Quin, X. Gu, V. A. Soloshonok, M. D. Garduzzi, V. Hrubi, *Tetrahedron Lett.* 2001, 42, 145-148.

Templates (e1) and (e2): See J. Cluzeau, W. D. Lubell, *Biopolymers* 2005, 80, 98-150; R. Mueller, L. Revesz, *Tetrahedron Lett.* 1994, 35, 4091; H.-G. Lubell, W. D. Lubell, *J. Org. Chem.* 1996, 61, 9437; L. Colombo, M. DiGiacomo, G. Papeo, O. Carugo, C. Scolastico, L. Manzoni, *Tetrahedron Lett.* 1994, 35, 4031.

Templates (e3): See Cluzeau, W. D. Lubell, *Biopolymers* 2005, 80, 98-150; S. Hanessian, B. Ronan, A. Laoui, *Bioorg. Med. Chem. Lett.* 1994, 4, 1397; M. Angiolini, S. Araneo, L. Belvisi, E. Cesarotti, A. Checca, L. Crippa, L. Manzoni, C. Scolastico, *Eur. J. Org. Chem.* 2000, 2571-2581; L. Belvisi, A. Caporale, M. Colombo, L. Manzoni, D. Potenza, C. Scolastico, M. Castorina, M. Cati, G. Giannini, C. Pisano, *Helv. Chim. Acta* 2002, 85, 4353-4368; F. Gosselin, W. D. Lubell, *J. Org. Chem.* 2000, 65, 2163-2171; M. Shimizu, H. Nemoto, H. Kakuda, H. Takahata, *Heterocycles*, 2003, 59, 245-255; F. Gosselin, W. D. Lubell, *J. Org. Chem.* 1998, 63, 7463-71; F. Gosselin, D. Tourvé, M. Ceusters, T. Meert, L. Heylen, M. Jurzak, W. D. Lubell, *J. Pept. Chem.* 2001, 57, 337-44; L. Halab, J. A. J. Becker, Z. Darula, D. Tourvé, B. L. Kieffer, F. Simonin, W. D. Lubell, *J. Med. Chem.* 2002, 45, 5353-5357; R. Liu, D. L.-Y. Dong, R. Sherlock, H. P. Nestler, C. Cennari, A. Mielgo, C. Scoslastico, *Bioorg. Med. Chem. Lett.* 1999, 9, 847-852; A. Salimbeni, F. Peleari, R. Canevolti, M. Criscuoli, A. Lippi, M. Angiolini, L. Belvisi, C. Scolastico, L. Colombo, *Bioorg. Med. Chem. Lett.* 1997, 7, 2205-2210; F. Gosselin, W. D. Lubell, *J. Org. Chem.* 2001, 66, 1181-1185.

Templates (e4) see: S. Hanessian, G. McNaughton-Smith, *Bioorg. Med. Chem. Lett.* 1996, 6, 1567; F. Polyak, W. D. Lubell, *J. Org. Chem.* 2001, 66, 1171-1180; F. Polyak, W. D. Lubell, *J. Org. Chem.* 1998, 63, 5937-5949.

Templates (e5) see: Cluzeau, W. D. Lubell, *Biopolymers* 2005, 80, 98-150; R. St. Charles, J. H. Matthews, E. Zhang, A. Tulinsky, *J. Med. Chem.* 1999, 42, 1376-83; W. Wang, J. Yang, J. Ying, J. Zhang, Ch. Cai, V. J. Hrubi, *J. Org. Chem.* 2002, 67, 6352-60.

Templates (e6) see: Cluzeau, W. D. Lubell, *Biopolymers* 2005, 80, 98-150; F. Gosselin, W. D. Lubell, *J. Org. Chem.* 2000, 65, 2163-2171; F. Polyak, W. D. Lubell, *J. Org. Chem.* 1998, 63, 5937-5949.

Templates (e7) see: J. Cluzeau, W. D. Lubell, *Biopolymers* 2005, 80, 98-150; F. Polyak, W. D. Lubell, *J. Org. Chem.* 1998, 63, 5937-5949; W. Wang, J. Yang, J. Ying, J. Zhang, Ch. Cai, V. J. Hrubi, *J. Org. Chem.* 2002, 67, 6352-60; E. Artale, G. Banfi, L. Belvisi, L. Colombo, M. Colombo, L. Manzoni, C. Scolastico, *Tetrahedron* 2003, 59, 6241-6250; Z. Feng, W. D. Lubell, *J. Org. Chem.* 2001, 66, 1181-1185.

Templates (e8) and (e9): J. Cluzeau, W. D. Lubell, *Biopolymers* 2005, 80, 98-150; R. St. Charles, J. H. Matthews, E. Zhang, A. Tulinsky, *J. Med. Chem.* 1999, 42, 1376-83;

Templates (e10) see: J. Cluzeau, W. D. Lubell, *Biopolymers* 2005, 80, 98-15; F. Gosselin, D. Tourvé, M. Ceusters, T. Meert, L. Heylen, M. Jurzak, W. D. Lubell, *J. Pept. Chem.* 2001, 57, 337-44; L. Halab, J. A. J. Becker, Z. Darula, D. Tourvé, B. L. Kieffer, F. Simonin, W. D. Lubell, *J. Med. Chem.* 2002, 45, 5353-5357; U. Nagai, K. Sato, *Tetrahedron Lett.* 1985, 26, 647-650; J. A. J. Becker, A. Wallau, A. Garzon, P. Ingallinella, E. Bianchi, R. Cortese, F. Simonin, B. L. Kieffer, A. Pessi, *J. Biol. Chem.* 1999, 274, 27513-22; J. Wagner, J. Kallen, C. Eberhardt, J.-P. Evenou, D. Wagner, *J. Med. Chem.* 1998, 41, 3664-74; R. E. Dolle, C. V. C. Prasad, C. P. Prouty, J. M. Salvino, M. M. A. Awad, St. J. Smith, D. Hoyer, T. M. Ross, T. L. Graybill, G. J. Speiser, J. Uhl, B. E. Miller, C. T. Helaszek, M. A. Ator, *J. Med. Chem.* 1997, 40, 1941-46; F. Weisskirchen, P. M. Doyle, S. L. Gough, C. J. Harris, I. Marshall, *Brit. J. Pharmacol.* 1999, 126, 1163-70.

Template (e11): The preparation of these starting and pre-starting materials are described in International Application PCT/EP02/01711 of the same applicants, published as WO 02/070547 A1 (m).

Templates (e12): See U. Slomcynska, D. K. Chalmers, F. Cornille, M. L. Smythe, D. D. Benson, K. D. Moeller, G. R. Marshall, *J. Org. Chem.* 1996, 61, 1198-1204; F. Gosselin, D. Tourvé, M. Ceusters, T. Meert, L. Heylen, M. Jurzak, W. D. Lubell, *J. Pept. Chem.* 2001, 57, 337-44.

Templates (e13): See D. Gramberg, C. Weber, R. Beeli, J. Inglis, C. Bruns, J. A. Robinson, *Helv. Chem. Acta* 1995, 78, 1588-1606; K. H. Kim, J. P. Dumas, J. P. Germanas, *J. Org. Chem.* 1996, 61, 3138-3144.

Templates (f): J. Cluzeau, W. D. Lubell, *Biopolymers* 2005, 80, 98-15; F. Gosselin, D. Tourvé, M. Ceusters, T. Meert, L. Heylen, M. Jurzak, W. D. Lubell, *J. Pept. Chem.* 2001, 57, 337-44; L. Halab, J. A. J. Becker, Z. Darula, D. Tourvé, B. L. Kieffer, F. Simonin, W. D. Lubell, *J. Med. Chem.* 2002, 45, 5353-5357; F. Gosselin, W. D. Lubell, *J. Org. Chem.* 1998, 63, 7463-71.

Templates (g1-g4): See J. Cluzeau, W. D. Lubell, *Biopolymers* 2005, 80, 98-15; F. Gosselin, D. Tourvé, M. Ceusters, T. Meert, L. Heylen, M. Jurzak, W. D. Lubell, *J. Org. Chem.* 2000, 65, 2163-2171; M. Mizutani, W.-H. Chiou, I. Ojima, *Org. Lett.* 2002, 4, 4575-78.

Templates (h1): See J. Cluzeau, W. D. Lubell, *Biopolymers* 2005, 80, 98-15; M. Angiolini, S. Araneo, L. Belvisi, E. Cesarotti, A. Checca, L. Crippa, L. Manzoni, C. Scolastico, *Eur. J. Org. Chem.* 2000, 2571-2581; L. Colombo, M. Di Giacomo, V. Vinci, M. Colombo, L. Manzoni, C. Scolastico, *Tetrahedron* 2003, 59, 4353-68; F. Gosselin, W. D. Lubell, *J. Org. Chem.* 2000, 65, 2163-2171; R. Liu, D. L.-Y. Dong, R. Sherlock, H. P. Nestler, C. Cennari, A. Mielgo, C. Scoslastico, *Bioorg. Med. Chem. Lett.* 1999, 9, 847-852; E. Artale, G. Banfi, L. Belvisi, L. Colombo, M. Colombo, L. Manzoni, C. Scolastico, *Tetrahedron* 2003, 59, 6241-6250.

Templates (h2): See J. Cluzeau, W. D. Lubell, *Biopolymers* 2005, 80, 98-15; D. S. Karanewsky, X. Bai, S. T. Linton, J. F. Krebs, J. Wu, B. Pham, K. J. Tomaselli, *Bioorg. Med. Chem. Lett.* 1998, 8, 2557-2762.

Templates (h3): See J. Cluzeau, W. D. Lubell, *Biopolymers* 2005, 80, 98-15; T. P. Curran, P. M. McEnay, *Tetrahedron Lett.* 1995, 36, 191-194.

Templates (i): See J. Cluzeau, W. D. Lubell, *Biopolymers* 2005, 80, 98-15; M. R. Attwood, C. H. Hassal, A. Kröhn, G. Lawton, S. Redshaw, *J. Chem. Soc. Perkin Trans.* 1, 1986, 1011-19; R. E. Dolle, C. V. C. Prasad, C. P. Prouty, J. M. Salvino, M. M. A. Awad, St. J. Smith, D. Hoyer, T. M. Ross, T. L. Graybill, G. J. Speiser, J. Uhl, B. E. Miller, C. T. Helaszek, M. A. Ator, *J. Med. Chem.* 1997, 40, 1941-46; F. Weisskirchen, P. M. Doyle, S. L. Gough, C. J. Harris, I. Marshall, *Brit. J. Pharmacol.* 1999, 126, 1163-70.

Templates (k): D. Tourvé et al. *Biopolymers* 1996, 38, 1-12; commercially available (NeoMPS FB 04901).

Templates (l1): See J. Cluzeau, W. D. Lubell, *Biopolymers* 2005, 80, 98-15; J. A. Robl, L. M. Simpkins, J. Stevenson, Ch.-Q. Sun, N. Marugesan, J. C. Banish, M. M. Asaad; J. E. Bird, T. R. Schaeffer, N. C. Trippodo, E. W. Petrillo, D. S. Karanewsky, *Bioorg. Med. Chem. Lett.* 1994, 4, 1789-94; R. E. Dolle, C. V. C. Prasad, C. P. Prouty, J. M. Salvino, M. M. A. Awad, St. J. Smith, D. Hoyer, T. M. Ross, T. L. Graybill, G. J. Speiser, J. Uhl, B. E. Miller, C. T. Helaszek, M. A. Ator, *J. Med. Chem.* 1997, 40, 1941-46; for $R^{11}$=$R^{22}$=H; commercially available (NeoMPS FB05001).

Templates (l2): See J. Cluzeau, W. D. Lubell, *Biopolymers* 2005, 80, 98-15; J. A. Robl, L. M. Simpkins, J. Stevenson, Ch.-Q. Sun, N. Marugesan, J. C. Barrish, M. M. Asaad; J. E. Bird, T. R. Schaeffer, N.C. Trippodo, E. W. Petrillo, D. S. Karanewsky, *Bioorg. Med. Chem. Lett.* 1994, 4, 1789-94; M. Amblard et al. *J. Med. Chem.* 1999, 42, 4185; for $R^{11}$=$R^{22}$=H; commercially available (NeoMPS FB04801).

Templates (l3-l4): See J. Cluzeau, W. D. Lubell, *Biopolymers* 2005, 80, 98-15; J. A. J. Becker, A. Wallau, A. Garzon, P. Ingallinella, E. Bianchi, R. Cortese, F. Simonin, B. L. Kieffer, A. Pessi, *J. Biol. Chem.* 1999, 274, 27513-22; L. Halab, J. A. J. Becker, Z. Darula, D. Tourvé, B. L. Kieffer, F. Simonin, W. D. Lubell, *J. Med. Chem.* 2002, 45, 5353-5357; (13) for $R^{11}$=$R^{22}$=H; commercially available (NeoMPS FB02401).

Templates (m): See J. Cluzeau, W. D. Lubell, *Biopolymers,* 2005, 80, 98-15; J. A. J. Becker, A. Wallau, A. Garzon, P. Ingallinella, E. Bianchi, R. Cortese, F. Simonin, B L Kieffer, A. Pessi, *J. Biol. Chem.* 1999, 274, 27513-22.

Templates (n): See J. Cluzeau, W. D. Lubell, *Biopolymers* 2005, 80, 98-15; P. Ward, G. B. Evan, C. C. Jordan, S. J. Ireland, R. M. Hagan, J. R. Brown, *J. Med. Chem.* 1990, 33, 1848-51.

Templates (o): See J. Cluzeau, W. D. Lubell, *Biopolymers* 2005, 80, 98-15; S. de Lombart, L. Blanchard, L. B. Stamford, D. M. Sperbeck, M. D. Grim, T. M. Jenson, H. R.

Rodriguez, *Tetrahedron Lett.* 1994, 35, 7513-7516; F. Weisskirchen, P. M. Doyle, S. L. Gough, C. J. Harris, I. Marshall, *Brit. J. Pharmacol.* 1999, 126, 1163-70; J. A. J. Becker, A. Wallau, A. Garzon, P. Ingallinella, E. Bianchi, R. Cortese, F. Simonin, B. L. Kieffer, A. Pessi, *J. Biol. Chem.* 1999, 274, 27513-22; L. Halab, J. A. J. Becker, Z. Darula, D. Tourvé, B. L. Kieffer, F. Simonin, W. D. Lubell, *J. Med. Chem.* 2002, 45, 5353-5357.

Templates (p1-p4): See J. Cluzeau, W. D. Lubell, *Biopolymers* 2005, 80, 98-15; J. A. Robl, D. S. Karanewski, M. M. Asaad, *Tetrahedron Lett.* 1995, 5, 773-758; T. P. Burkholder, T.-B. Le, E. L. Giroux, G. A. Flynn, *Bioorg. Med. Chem. Lett.* 1992, 2, 579; L. M. Simpkins, J. A. Robl, M. P. Cimarusti, D. E. Ryono, J. Stevenson, C.-Q. Sun, E. W. Petrillo, D. S. Karanewski, M. M. Asaad, J. E. Bird, T. R. Schaeffer, N.C. Trippodo, Abstracts of papers, 210$^{th}$ Am. Chem. Soc Meeting, Chicago, Ill., MEDI 064 (1995).

Templates (q): See J. Cluzeau, W. D. Lubell, *Biopolymers* 2005, 80, 98-15; D. Benlshai, A. R. McMurray, *Tetrahedron* 1993, 49, 6399.

Templates (r): See J. Cluzeau, W. D. Lubell, *Biopolymers* 2005, 80, 98-15; F. Esser, A. Carpy, H. Briem, H. Köppen, K.-H. Pook, *Int. J. Pept. Res.* 1995, 45, 540-546.

Templates (s): See J. Cluzeau, W. D. Lubell, *Biopolymers* 2005, 80, 98-15; N. De la Figuera, I. Alkorta, T. Garcia-Lopez, R. Herranz, R. Gonzalez-Muniz, *Tetrahedron* 1995, 51, 7841.

The β-hairpin peptidomimetics of the invention can be used in a wide range of applications in order to agonize or to antagonize GPCR receptors.

They can be used, for example, for treating or preventing cardiovascular disorders, dermatological disorders, endocrine system and hormone disorders, metabolic diseases, inflammatory diseases, neurological diseases, respiratory diseases, haematological diseases and cancer.

For use as medicaments the β-hairpin peptidomimetics can be administered singly, as mixtures of several β-hairpin peptidomimetics or in combination with other pharmaceutically active agents. The β-hairpin peptidomimetics may be administered per se or may be applied as an appropriate formulation together with carriers, diluents or excipients well known in the art.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin pepdidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free base forms.

The β-hairpin peptidomimetics of the invention, or compositions thereof, will generally be used in an amount effective to achieve the intended purpose. It is to be understood that the amount used will depend on a particular application.

For use to treating or preventing cardiovascular disorders, dermatological disorders, endocrine system and hormone disorders, metabolic diseases, inflammatory diseases, neurological diseases, respiratory diseases, haematological diseases and cancer, the β-hairpin pepidomimetics of the invention, or compositions thereof, are administered or applied in a therapeutically effective amount. By therapeutically effective amount is meant an amount effective in ameliorating the symptoms of, or in ameliorating, treating or preventing microbial infections or diseases related thereto. Determination of a therapeutically effective amount is well within the capacities of those skilled in the art, especially in view of the detailed disclosure provided herein.

For systemic administration, a therapeutically effective dose can be estimated initially from in vitro assays. For example, a dose can be formulated in animal models to achieve a circulating β-hairpin peptidomimetic concentration range that includes the $IC_{50}$ as determined in the cell culture (i.e. the concentration of a test compound that is lethal to 50% of a cell culture), the MIC, as determined in cell culture (i.e. the concentration of a test compound that is lethal to 100% of a cell culture). Such information can be used to more accurately determine useful doses in humans.

Initial dosages can also be determined from in vivo data, e.g. animal models, using techniques that are well known in the art. One having ordinary skills in the art could readily optimize administration to humans based on animal data.

Dosage amount for applications as antimicrobial agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the skills in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

Normally, a therapeutically effective dose of the β-hairpin peptidomimetics described herein will provide therapeutic benefit without causing substantial toxicity.

Toxicity of the β-hairpin peptidomimetics of the invention herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch. 1, p. 1).

The following Examples illustrate the invention in more detail but are not intended to limit its scope in any way. The following abbreviations are used in these Examples:

HBTU: 1-benzotriazol-1-yl-tetramethylurounium hexafluorophosphate (Knorr et al. *Tetrahedron Lett.* 1989, 30, 1927-1930);

HCTU: 1-Benzotriazol 1-[bis(dimethylamino)methylene]-5chloro-hexafluorophosphate-(1-),3-oxide HOBt: 1-hydroxybenzotriazole;

DIEA: diisopropylethylamine;

HOAT: 7-aza-1-hydroxybenzotriazole;

HATU: O-(7-aza-benzotriazole-1-yl)-N,N,N',N'-tetramethyluronoium hexafluorophosphate (Carpino et al. *Tetrahedron Lett.* 1994, 35, 2279-2281).

EXAMPLES

1. Peptide Synthesis

Coupling of the First Protected Amino Acid Residue to the Resin 0.5 g of 2-chlorotritylchloride resin (Barlos et al. *Tetrahedron Lett.* 1989, 30, 3943-3946) (1.4 mMol/g, 0.7 mmol) was filled into a dried flask. The resin was suspended in $CH_2Cl_2$ (2.5 ml) and allowed to swell at room temperature under constant stirring for 30 min. The resin was treated with 0.49 mMol (0.7 eq) of the first suitably protected amino acid residue or building block (see below) and 488 µl (4 eq) of diisopropylethylamine (DIEA) in $CH_2Cl_2$ (2.5 ml), the mixture was shaken at 25° C. for 4 hours. The resin was shaken ($CH_2Cl_2$/MeOH/DIEA: 17/2/1), 30 ml for 30 min; then washed in the following order with $CH_2Cl_2$ (1×), DMF (1×), $CH_2Cl_2$ (1×), MeOH (1×), $CH_2Cl_2$(1×), MeOH (1×), $CH_2Cl_2$ (2×), $Et_2O$ (2×) and dried under vacuum for 6 hours.

Loading was typically 0.6-0.9 mMol/g.

The following preloaded resins were prepared: Fmoc-Tic-2-chlorotritylresin, Fmoc-Azt-2-chlorotritylresin, Fmoc-b1-$x^1$-2-chlorotritylresin, Fmoc-c1-$x^2$-2-chlorotritylresin,

[1] b1-x is (2S,6S,9S)-6-amino-2-carboxymethyl-3,8-diazabicyclo-[4,3,0]-nonane-1,4-dione

[2] c1-X is 5-aminomethyl-3,6-dimethoxy-9,9-dimethyl-9H-xanthen-4-yl-acetic acid Synthesis of the Fully Protected Peptide Fragment The synthesis was carried out on a Syro-peptide synthesizer (MultiSynTech GmbH) using 24 to 96 reaction vessels. In each vessel were placed approximately 60 mg (weight of the resin before loading) of the above resin. The following reaction cycles were programmed and carried out:

| Step | Reagent | Time |
|---|---|---|
| 1 | $CH_2Cl_2$, wash and swell (manual) | 1 × 3 min. |
| 2 | DMF, wash and swell | 1 × 60 min |

-continued

| Step | Reagent | Time |
|---|---|---|
| 3 | 40% piperidine/DMF | 2 × 5 min. |
| 4 | DMF, wash | 5 × 1 min. |
| 5 | 5 equiv. Fmoc amino acid/DMF +5 eq. HCTU +10 eq. DIEA | 2 × 60 min. |
| 6 | DMF, wash | 5 × 1 min. |
| 7 | 40% piperidine/DMF | 2 × 5 min. |
| 8 | DMF, wash | 5 × 1 min. |
| 9 | $CH_2Cl_2$, wash (at the end of the synthesis) | 3 × 1 min. |

Steps 3 to 6 are repeated to add each amino-acid.

After the synthesis of the fully protected peptide fragment had been terminated, the cleavage, cyclization and work up procedure as described hereinbelow, was used for the preparation of the peptides.

Analytical Method A:

Analytical HPLC retention times (RT, in minutes) were determined using an Jupiter Proteo 90A, 150×2.0 mm, (cod. 00F4396-B0—Phenomenex) with the following solvents A ($H_2O$+0.1% TFA) and B ($CH_3CN$+0.1% TFA) and the gradient: 0-0.5 min: 95% A, 5% B; 15 min 40% A 60% B; 15.05-21.0 min: 0% A, 100% B; 21.1-30 95% A, 5% B.

Analytical Method B:

Analytical HPLC retention times (RT, in minutes) were determined using an Jupiter Proteo 90A, 50×2.0 mm, (cod. 00B-4396-B0-Phenomenex) with the following solvents A ($H_2O$+0.1% TFA) and B ($CH_3CN$+0.1% TFA) and the gradient: 0-0.5 min: 95% A, 5% B; 20 min: 40% A 60% B; 20.5-27 min: 0% A, 100% B; 27.1-40 min: 95% A, 5% B.

Analytical Method C:

Analytical HPLC retention times (RT, in minutes) were determined using an ACQUITY HPLC™ BEH C18 2.1×100 mm 1.7 μm (cod. 186002352—WATERS) with the following solvents A ($H_2O$+0.1% TFA) and B ($CH_3CN/H_2O$ 95/5+ 0.085% TFA) and the gradient: 0-0.2 mini: 95% A, 5% B; 4 min: 35% A 65% B; 4.2 min: 5% A, 95% B; 4.25 min: 95% A, 5% B.

Analytical Method D:

Analytical HPLC retention times (RT, in minutes) were determined using an Jupiter Proteo 90A, 50×2.0 mm, (cod. 00B-4396-B0-Phenomenex) with the following solvents A ($H_2O$+0.1% TFA) and B ($CH_3CN$+0.1% TFA) and the gradient: 0-0.5 min: 95% A, 5% B; 10 min: 40% A 60% B; 10.05-15.0 min: 0% A, 100% B; 15.1-20 min: 95% A, 5% B.

Cleavage, Backbone Cyclization, Deprotection and Purification of the Peptide

After assembly of linear peptide, the resin was suspended in 1 ml (0.14 mMol) of 1% TFA in $CH_2Cl_2$ (v/v) for 3 minutes and filtered, and the filtrate was neutralized with 1 ml (1.15 mMol) of 20% DIEA in $CH_2Cl_2$ (v/v). This procedure was repeated twice to ensure completion of the cleavage. The resin was washed three times with 1 ml of $CH_2Cl_2$. The $CH_2Cl_2$ layer was evaporated to dryness.

The fully protected linear peptide was solubilised in 8 ml of dry DMF. Then 2 eq. of HATU in dry DMF (1 ml) and 4 eq. of DIEA in dry DMF (1 ml) were added to the peptide, followed by stirring for 16 h. The volatiles were evaporated to dryness. The crude cyclic peptide was dissolved in 7 ml of $CH_2Cl_2$ and extracted with 10% acetonitrile in water (4.5 ml), three times. The $CH_2Cl_2$ layer was evaporated to dryness. To fully deprotect the peptide, 4 ml of cleavage cocktail TFA: TIS:$H_2O$ (95:2.5:2.5) were added, and the mixture was stirred for 4 h at room temperature. The volatile was evaporated to dryness and the crude peptide was dissolved in 20% AcOH in water (7 ml) and extracted with diisopropyl ether (4 ml) for three times. The aqueous layer was collected and evaporated to dryness, and the residue was purified by preparative reverse phase LC-MS.

After lyophilisation the products were obtained as white powders and analysed by HPLC-ESI-MS methods as described above. Analytical data after preparative HPLC purification are shown in Table 1.

Examples 1-3, 17-19, are shown in Table I. The peptides were synthesized starting with the amino acid L-Tic which was grafted to the resin. Starting resin was Fmoc-Tic-2-chlorotrityl resin, which was prepared as described above. The linear peptides were synthesized on solid support according to the procedure described above in the following sequence: Resin-Tic-$^D$Pro-P4-P3-P2-P1. The products were cleaved from the resin, cyclized, deprotected and purified as indicated by preparative reverse phase LC-MS.

After lyophilisation the products were obtained as white powders and analysed by HPLC-ESI-MS method A as described above for 1-3, method C as described above for 17 and 18 and method D as described above for 19.

HPLC-retention times (minutes) were determined using the analytical method as described above.

Examples 4-7 are also shown in Table 1. The peptides were synthesized starting with the amino acid L-Azt which was grafted to the resin. Starting resin was Fmoc-Azt-2-chlorotrityl resin, which was prepared as described above. The linear peptides were synthesized on solid support according to the procedure described above in the following sequence: Resin-Azt-$^D$Pro-P4-P3-P2-P1. The products were cleaved from the resin, cyclized, deprotected and purified as indicated by preparative reverse phase LC-MS.

After lyophilisation the products were obtained as white powders and analysed by HPLC-ESI-MS method A as described above.

HPLC-retention times (minutes) were determined using the analytical method as described above.

Examples 8-13, are likewise shown in Table 1. The peptides were synthesized starting with the template c1-x which was grafted to the resin. Starting resin was Fmoc-c1-x-2-chlorotrityl resin, which was prepared as described above. The linear peptides were synthesized on solid support according to the procedure described above in the following sequence: Resin-c1-x-P4-P3-P2-P1. The products were cleaved from the resin, cyclized, deprotected and purified as indicated by preparative reverse phase LC-MS.

After lyophilisation the products were obtained as white powders and analysed by HPLC-ESI-MS method A as described above.

HPLC-retention times (minutes) were determined using the analytical method as described above.

Examples 14, is shown in Table 1, too. The peptide was synthesized starting with the template b1-x which was grafted to the resin. Starting resin was Fmoc-b1-x-2-chlorotrityl resin, which was prepared as described above. The linear peptide was synthesized on solid support according to the procedure described above in the following sequence: Resin-b1-x-P4-P3-P2-P1. The product was cleaved from the resin, cyclized, deprotected and purified as indicated by preparative reverse phase LC-MS.

After lyophilisation the product was obtained as white powder and analysed by HPLC-ESI-MS method A as described above.

HPLC-retention time (minutes) was determined using the analytical method as described above.

Examples 15-16, finally, are also shown in Table 1. The peptides were synthesized starting with the amino acid L-Azt which was grafted to the resin. Starting resin was Fmoc-Azt-2-chlorotrityl resin, which was prepared as described above. The linear peptides were synthesized on solid support according to the procedure described above in the following sequence: Resin-Azt-$^D$Pro-P4-P3-P2-P1. The products were cleaved from the resin, cyclized, deprotected and purified as indicated by preparative reverse phase LC-MS.

After lyophilisation the products were obtained as white powders and analysed by HPLC-ESI-MS method B as described above.

HPLC-retention times (minutes) were determined using the analytical method as described above.

2.3. CCR10 and CXCR3

Peptides for CCR10 (Marchese et. al. 1994, Homey et. al.) and CXCR3 (Loetscher et. al. 1998, Marchese et. al. 1995) antagonism were assayed in a mouse pre-B cell line 300-19 stably transfected with either human CCR10 or CXCR3 (Marchese et. al. 1995). Antagonism at each receptor was measured with a calcium flux assay in these cells as described above for UTR2 assays using human CCL27 and human CXCL10 (Cole et. al.) for CCR10 and CXCR3 respectively.

Selectivity was measured using the calcium flux assay on a panel of human chemokine receptor bearing cell lines (CCR1, CCR2, CCR3, CCR4, CCR5, CCR6, CCR7, CCR8, CCR9,

TABLE 1

Examples

| Example | Sequ. ID | P1 | P2 | P3 | P4 | Template | Purity %[a] | [M + H] | RT |
|---|---|---|---|---|---|---|---|---|---|
| 1 | SEQ ID NO: 1 | Phe | Trp | Lys | Tyr | $^D$Pro$^L$Tic | 95 | 881.2 | 12.63 |
| 2 | SEQ ID NO: 2 | Ile | Trp | Lys | Tyr | $^D$Pro$^L$Tic | 92 | 847.2 | 12.48 |
| 3 | SEQ ID NO: 3 | Gln | Trp | Lys | Tyr | $^D$Pro$^L$Tic | 91 | 862.2 | 9.59 |
| 4 | SEQ ID NO: 4 | Phe | Trp | Lys | Tyr | $^D$Pro$^L$Azt | 95 | 805.2 | 10.68 |
| 5 | SEQ ID NO: 5 | Ile | Trp | Lys | Tyr | $^D$Pro$^L$Azt | 92 | 771.4 | 10.49 |
| 6 | SEQ ID NO: 6 | Gln | Trp | Lys | Tyr | $^D$Pro$^L$Azt | 88 | 786.2 | 7.67 |
| 7 | SEQ ID NO: 7 | Thr | Trp | Lys | Tyr | $^D$Pro$^L$Azt | 89 | 759.2 | 8.21 |
| 8 | SEQ ID NO: 8 | Phe | Trp | Lys | Tyr | c1-x | 92 | 964.2 | 14.41 |
| 9 | SEQ ID NO: 9 | Thr | Trp | Lys | Tyr | c1-x | 92 | 918.3 | 12.97 |
| 10 | SEQ ID NO: 10 | Gln | Trp | Lys | Tyr | c1-x | 95 | 945.1 | 12.01 |
| 11 | SEQ ID NO: 11 | Ile | Trp | Lys | Tyr | c1-x | 95 | 930.2 | 14.18 |
| 12 | SEQ ID NO: 12 | Trp | Lys | Tyr | His | c1-x | 95 | 954.5 | 11.64 |
| 13 | SEQ ID NO: 13 | Glu | Trp | Lys | Tyr | c1-x | 92 | 946.2 | 12.39 |
| 14 | SEQ ID NO: 14 | Ile | Trp | Lys | Tyr | b1-x | 84 | 800.6 | 10.84 |
| 15 | SEQ ID NO: 15 | Tyr | Trp | Arg | Gly | $^D$Pro$^L$Azt | 95 | 742.8 | 9.17 |
| 16 | SEQ ID NO: 16 | Tyr | Trp | Arg | Ala | $^D$Pro$^L$Azt | 93 | 756.8 | 10.10 |
| 17 | SEQ ID NO: 17 | Trp | $^D$Val | Trp | Orn | $^D$Pro$^L$Tic | 95 | 842.8 | 3.22 |
| 18 | SEQ ID NO: 18 | Trp | $^D$Val | Trp | Lys | $^D$Pro$^L$Tic | 95 | 856.8 | 3.26 |
| 19 | SEQ ID NO: 19 | Ile | $^D$Arg | Aib | Ile | $^D$Pro$^L$Tic | 92 | 724.2 | 8.38 |

[a]%-purity of compounds after prep. HPLC.
b1-x is (2S,6S,9S)-6-amino-2-carboxymethyl-3,8-diazabicyclo-[4,3,0]-nonane-1,4-dione
c1-x is (5-aminomethyl-3,6-dimethoxy-9,9-dimethyl-9H-xanthen-4yl-acetic acid 2. Biological Methods 2.1. Preparation of the Peptide Samples.

Lyophilized peptides were weighed on a Microbalance (Mettler MX5) and dissolved in sterile water to a final concentration of 1 mM less stated otherwise. Stock solutions were kept at +4° C., and protected from light.

2.2. Urotensin

The mouse pre-B cell line 300-19 was stably transfected with the cDNA encoding the human UTR2 receptor (GenBank Acc# NM_018949), and expression was confirmed with a positive calcium signal in response to human urotensin (Sigma Aldrich). Increases in intracellular calcium were monitored using a Flexstation 384 (Molecular Devices, Sunnyvale, Calif.). The cells were batch loaded with the Calcium 3 Assay kit (Molecular Devices) in assay buffer (Hanks Balanced salt solution, HBSS, 20 mM HEPES, pH 7.4, 0.1% BSA) for 1 h at room temperature and labeled cells were dispensed into either black 96 well or 384 well assay plates (Greiner). Calcium mobilization induced by urotensin or compounds was measured in the Flexstation 384 (excitation, 485 nM; emission, 525 nM) for 70 seconds. Agonist activity was determined by direct addition of ligand or peptides, while antagonists were identified by pre-incubation of compounds with cells prior to urotensin addition. A dose response curve (compound concentration versus % maximum response for urotensin) was determined for each active agonist and antagonist and was fitted to a four parameter logistic equation using SoftmaxPro 4.6 (Molecular Devices), from which EC50% and IC50% values were calculated.

CCR10, CXCR1, CXCR2, CXCR2, CXCR4, CXCR6 and CXCCR1) using the same method as above 3. Results

TABLE 1

| Ex. | EC50% (nM) ± SD, Urotensin receptor |
|---|---|
| 1 | 54 ± 12 |
| 2 | 68 ± 32 |
| 3 | 82 ± 13 |
| 4 | 20 ± 5 |
| 5 | 45 ± 22 |
| 6 | 134 ± 61 |
| 7 | 286 ± 66 |
| 8 | 18 ± 3 |
| 9 | 160 ± 81 |
| 10 | 170 ± 40 |
| 11 | 192 ± 14 |
| 12 | 218 |
| 13 | 274 ± 5 |
| 14 | 189 ± 13 |

TABLE 2

| Ex. | IC50% (µM) ± SD, Urotensin receptor |
|---|---|
| 19 | 6.2 ± 1.5 |

Examples 1-14 were highly selective at 10 μM against the CXCR4 chemokine receptor

TABLE 3

| Ex. | IC50% (μM) ± SD, CXCR3 receptor |
|---|---|
| 15 | IC50% = 8.6 ± 1.9 μM |
| 16 | IC50% = 8.1 ± 2.6 μM |

Examples 15 and 16 were highly selective at 10 μM against the following chemokine receptors: CCR1, CCR2, CCR3, CCR4, CCR5, CCR6, CCR7, CCR8, CCR9, CCR10, CXCR1, CXCR2, CXCR2, CXCR4, CXCR6 and CXCCR1.

TABLE 4

| Ex. | IC50% (μM), CCR10 receptor |
|---|---|
| 17 | IC50% = 0.31 μM |
| 18 | IC50% = 0.29 μM |

REFERENCES

1. Cole K E, Strick C A, Paradis T J, Ogborne K T, Loetscher M, Gladue R P, Lin W, Boyd J G, Moser B, Wood D E, Sahagan B G, Neote K. *J Exp Med.* 1998 Jun. 15; 187(12): 2009-21.
1. Marchese, A.; Docherty, J. M.; Nguyen, T.; Heiber, M.; Cheng, R.; Heng, H. H. Q.; Tsui, L.-C.; Shi, X.; George, S. R.; O'Dowd, B. F. *Genomics* 23: 609-618, 1994.
6. Homey, B.; Wang, W.; Soto, H.; Buchanan, M. E.; Wiesenborn, A.; Catron, D.; Müller, A.; McClanahan, T. K.; Dieu-Nosjean, M.-C.; Orozco, R.; Ruzicka, T.; Lehmann, P.; Oldham, E.; Zlotnik, A. *J. Immun.* 164: 3465-3470, 2000.
7. Loetscher, M.; Loetscher, P.; Brass, N.; Meese, E.; Moser, B. *Europ. J. Immun.* 28: 3696-3705, 1998.
8. Marchese, A.; Heiber, M.; Nguyen, T.; Heng, H. H. Q.; Saldivia, V. R.; Cheng, R.; Murphy, P. M.; Tsui, L.-C.; Shi, X.; Gregor, P.; George, S. R.; O'Dowd, B. F.; Docherty, J. M. *Genomics* 29: 335-344, 1995

The invention claimed is:

1. A compound of the formula

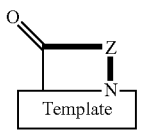

(I)

(i) in which

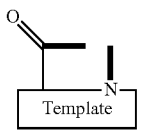

is either (a) a group of one of the formulae

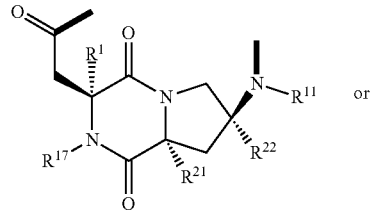

(b1)

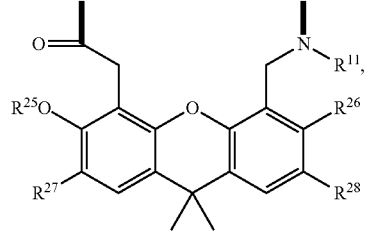

(c1)

wherein in formula b1

$R^1$ is H; lower alkyl; lower alkenyl; —$(CH_2)_p(CHR^{53})_s$ $OR^{47}$; —$(CH_2)_p(CHR^{53})_sSR^{48}$; —$(CH_2)_p(CHR^{53})_s$ $NR^{23}R^{24}$; —$(CH_2)_p(CHR^{53})_sOCONR^{50}R^{67}$; —$(CH_2)_p$ $(CHR^{53})_sNR^{11}CONR^{50}R^{51}$; —$(CH_2)_p(CHR^{53})_s$ $NR^{11}COR^{56}$; —$(CH_2)_o(CHR^{53})_sCOOR^{49}$; —$(CH_2)_o$ $(CHR^{53})_sCONR^{50}R^{51}$; —$(CH_2)_o(CHR^{53})_sPO(OR^{52})_2$; —$(CH_2)_o(CHR^{53})_sSO_2R^{54}$; or —$(CH_2)_o(CHR^{53})_sR^{69}$; and $R^{17}$ is H; lower alkyl; lower alkenyl; —$(CH_2)_m(CHR^{53})_s$ $OR^{47}$; —$(CH_2)_m(CHR^{53})_sSR^{48}$; —$(CH_2)_m(CHR^{53})_s$ $NR^{23}R^{24}$; —$(CH_2)_m(CHR^{53})_sOCONR^{50}R^{67}$; —$(CH_2)_m$ $(CHR^{53})_sNR^{11}CONR^{50}R^{51}$; —$(CH_2)_m(CHR^{53})_s$ $NR^{11}COR^{56}$; —$(CH_2)_r(CHR^{53})_sCOOR^{49}$; —$(CH_2)_r$ $(CHR^{53})_sCONR^{50}R^{51}$; —$(CH_2)_r(CHR^{53})_sPO(OR^{52})_2$; —$(CH_2)_r(CHR^{53})_sSO_2R^{54}$; or —$(CH_2)_o(CHR^{53})_sR^{69}$, wherein the variable defined in $R^1$ and $R^{17}$ are as follows:

$R^{11}$ is H; lower alkyl; lower alkenyl; or aryl-lower alkyl;

$R^{23}$ is H; lower alkyl; lower alkenyl; —$(CH_2)_m(CHR^{53})_s$ $OR^{47}$; $(CH_2)_m(CHR^{53})_sNR^{24}R^{55}$; —$(CH_2)_m$ $(CHR^{53})_s$ $OCONR^{50}R^{67}$; —$(CH_2)_m(CHR^{53})_s$ $NR^{11}CONR^{50}R^{51}$; —$(CH_2)_m(CHR^{53})_sNR^{11}COR^{56}$; —$(CH_2)_o(CHR^{53})_sCOOR^{49}$; —$(CH_2)_o(CHR^{53})_s$ $CONR^{50}R^{51}$; —$(CH_2)_o(CHR^{53})_sCOR^{56}$; —$(CH_2)_o$ $(CHR^{53})_sPO(OR^{52})_2$; —$(CH_2)_o(CHR^{53})_sSO_2R^{54}$; or —$(CH_2)_o(CHR^{53})_sR^{69}$;

$R^{24}$ is H; lower alkyl; aryl, or aryl-lower alkyl; or $R^{23}$ and $R^{24}$, taken together, are —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{47}$ is H; lower alkyl; lower alkenyl; aryl-lower alkyl; —$(CH_2)_m(CHR^{53})_sOR^{49}$; —$(CH_2)_m(CHR^{53})_s$ $NR^{23}R^{24}$; —$(CH_2)_m(CHR^{53})_sOCONR^{50}R^{67}$; —$(CH_2)_m(CHR^{53})_sNR^{11}CONR^{50}R^{51}$; —$(CH_2)_m$ $(CHR^{53})_sNR^{11}COR^{56}$; —$(CH_2)_o(CHR^{53})_sCOOR^{49}$; —$(CH_2)_o(CHR^{53})_sCONR^{50}R^{51}$; or —$(CH_2)_o$ $(CHR^{53})_sR^{69}$;

$R^{48}$ is H; lower alkyl; lower alkenyl; aryl-lower alkyl; —$(CH_2)_m(CHR^{53})_sOR^{49}$; —$(CH_2)_m(CHR^{53})_s$ $NR^{23}R^{24}$; —$(CH_2)_m(CHR^{53})_sOCONR^{50}R^{67}$; —$(CH_2)_m(CHR^{53})_sNR^{11}CONR^{50}R^{51}$; —$(CH_2)_m$ $(CHR^{53})_sNR^{11}COR^{56}$; —$(CH_2)_o(CHR^{53})_sCOOR^{49}$; or —$(CH_2)_o(CHR^{53})_sCONR^{50}R^{51}$;

$R^{49}$ is H; lower alkyl; lower alkenyl; aryl lower alkyl; or heteroaryl lower alkyl;

R$^{50}$ is H; lower alkyl; lower alkenyl; aryl; heteroaryl; aryl-lower alkyl; or heteroaryl-lower alkyl;

R$^{51}$ is H; lower alkyl; lower alkenyl; aryl; heteroaryl; aryl-lower alkyl; or heteroaryl-lower alkyl; or R$^{50}$ and R$^{51}$, taken together, are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—;

R$^{52}$ is H; lower alkyl; lower alkenyl; aryl; or aryl-lower alkyl;

R$^{53}$ is H, lower alkyl; lower alkenyl; aryl; heteroaryl; aryl-lower alkyl; heteroaryl-lower alkyl; —(CH$_2$)$_p$OR$^{47}$; —(CH$_2$)$_p$OCONR$^{50}$R$^{67}$; —(CH$_2$)$_p$NR$^{11}$CONR$^{50}$R$^{51}$; —(CH$_2$)$_p$NR$^{11}$COR$^{56}$; —(CH$_2$)$_o$COOR$^{49}$; —(CH$_2$)$_o$CONR$^{50}$R$^{51}$; or —(CH$_2$)$_o$PO(OR$^{52}$)$_2$;

R$^{54}$ is lower alkyl; lower alkenyl; aryl, heteroaryl; or aryl-lower alkyl;

R$^{56}$ is H; lower alkyl; lower alkenyl; —(CH$_2$)$_p$(CHR$^{53}$)$_s$OR$^{57}$; —(CH$_2$)$_p$(CHR$^{53}$)$_s$SR$^{58}$; —(CH$_2$)$_p$(CHR$^{53}$)$_s$NR$^{24}$R$^{55}$; —(CH$_2$)$_p$(CHR$^{53}$)$_s$OCONR$^{50}$R$^{67}$; —(CH$_2$)$_p$(CHR$^{53}$)$_s$NR$^{11}$CONR$^{50}$R$^{51}$; —(CH$_2$)$_p$(CHR$^{53}$)$_s$NR$^{11}$COR$^{56}$; or —(CH$_2$)$_o$(CHR$^{53}$)$_s$R$^{69}$;

R$^{67}$ is lower alkyl; lower alkenyl; or aryl-lower alkyl; or

R$^{50}$ and R$^{67}$, taken together, are —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—;

R$^{69}$ is —C$_6$R$^{59}$R$^{60}$R$^{61}$R$^{62}$R$^{68}$; or a heteroaryl group of one of the formulae

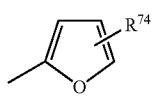 H1

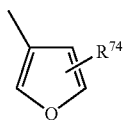 H2

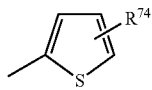 H3

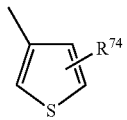 H4

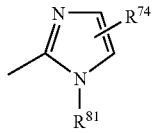 H5

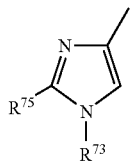 H6

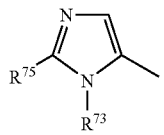 H7

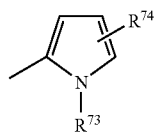 H8

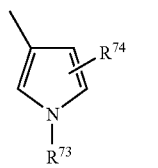 H9

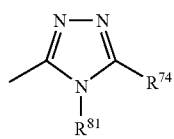 H10

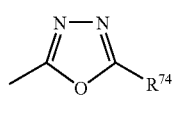 H11

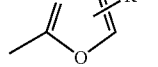 H12

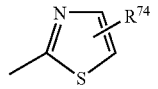 H13

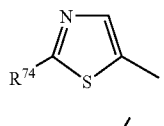 H14

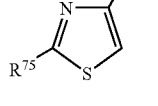 H15

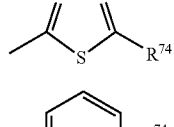 H16

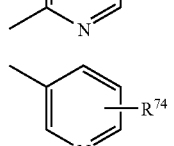 H17

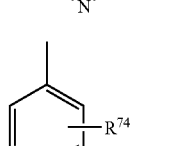 H18

 H19

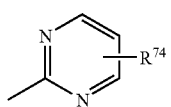 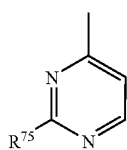 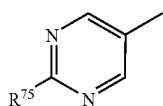 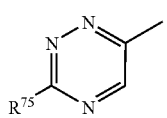 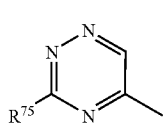 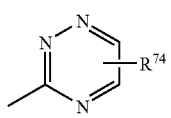 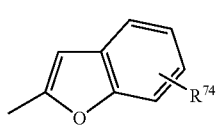 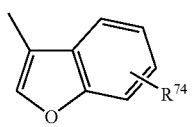 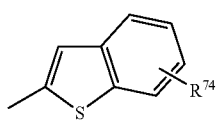 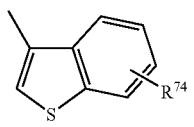 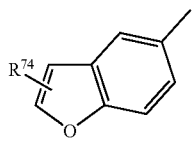 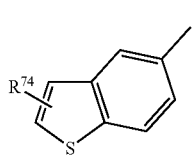
H20 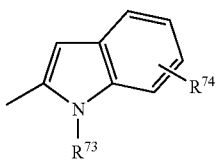
H21 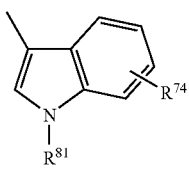
H22 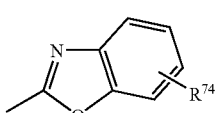
H23 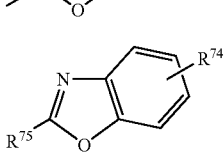
H24 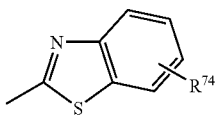
H25 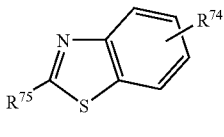
H26 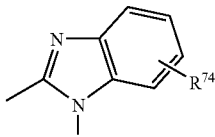
H27 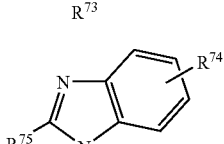
H28 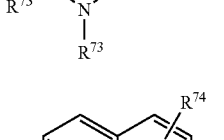
H29 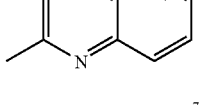
H30 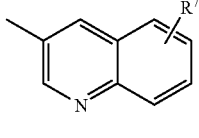
H31 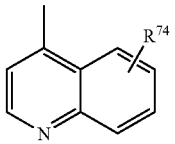
H32
H33
H34
H35
H36
H37
H38
H39
H40
H41
H42

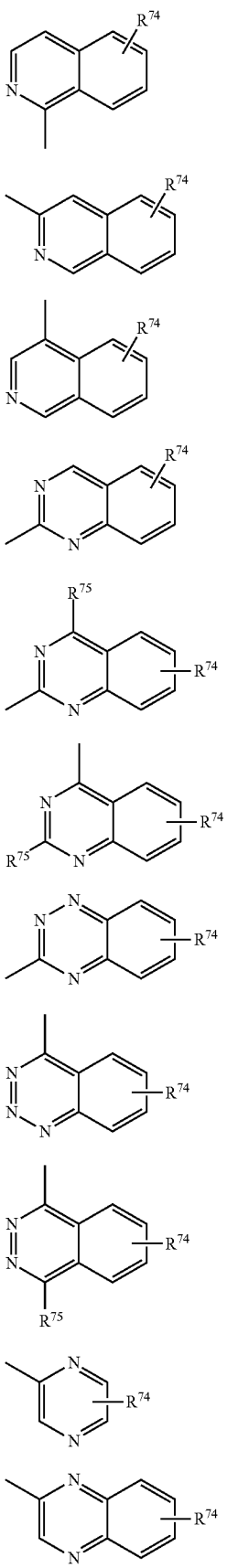

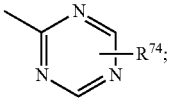

m is 2 to 4;
o is 0 to 4;
p is 1 to 4;
r is 1 or 2; and
s is 0 or 1,
wherein the variables defined in $R^{23}$, $R^{24}$, $R^{47}$, $R^{48}$, $R^{50}$, $R^{51}$, $R^{53}$, $R^{56}$, $R^{67}$ and $R^{69}$, each of the variables $R^{11}$, $R^{23}$, $R^{24}$, $R^{47}$, $R^{49}$, $R^{50}$, $R^{51}$, $R^{52}$, $R^{53}$, $R^{54}$, $R^{56}$, $R^{67}$, $R^{69}$, m, o, p and s has a meaning as defined above;

$R^{55}$ is H; lower alkyl; lower alkenyl; aryl; heteroaryl; aryl-lower alkyl; heteroaryl-lower alkyl; —$COR^{56}$; —$COOR^{49}$; —$CONR^{50}R^{51}$; —$SO_2R^{54}$; or —$PO(OR^{52})_2$; or $R^{24}$ and $R^{55}$, taken together, are —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{57}$ is H; lower alkyl; lower alkenyl; aryl, aryl-lower alkyl; heteroaryl-lower alkyl; —$COR^{56}$; —$COOR^{49}$; or —$CONR^{50}R^{51}$;

$R^{58}$ is H; lower alkyl; lower alkenyl; aryl; aryl-lower alkyl; heteroaryl-lower alkyl; or —$CONR^{50}R^{51}$;

$R^{59}$ is H; Cl; Br; F; $NO_2$; $CF_3$; CN; $OCF_3$; $OCHF_2$; —$NR^{24}COR^{56}$; lower alkyl; or lower alkenyl;

$R^{60}$ is H; Cl; Br; F; $NO_2$; $CF_3$; CN; $OCF_3$; $OCHF_2$; —$NR^{24}COR^{56}$; lower alkyl; or lower alkenyl;

$R^{61}$ is H; Cl; Br; F; $NO_2$; $CF_3$; CN; $OCF_3$; $OCHF_2$; —$NR^{24}COR^{56}$; lower alkyl; or lower alkenyl;

$R^{62}$ is H; Cl; Br; F; $NO_2$; $CF_3$; CN; $OCF_3$; $OCHF_2$; —$NR^{24}COR^{56}$; lower alkyl; or lower alkenyl;

with the proviso, that at least two of $R^{59}$, $R^{60}$, $R^{61}$ and $R^{62}$ are H;

$R^{68}$ is H; lower alkyl; lower alkenyl; aryl-lower alkyl; —$(CH_2)_oOR^{64}$; —$(CH_2)_oSR^{64}$; —$(CH_2)_oNR^{23}R^{24}$; —$(CH_2)_oOCONR^{50}R^{67}$; —$(CH_2)_oNR^{11}CONR^{50}R^{51}$; —$(CH_2)_oNR^{11}COR^{56}$; —$(CH_2)_oCOOR^{67}$; —$(CH_2)_oCONR^{50}R^{51}$; —$(CH_2)_oPO(OR^{52})_2$; —$(CH_2)_oSO_2R^{54}$; or —$(CH_2)_oCOOR^{56}$;

$R^{73}$ is H; lower alkyl; or aryl-lower alkyl;

$R^{74}$ is H; lower alkyl; aryl; heteroaryl; or aryl-lower alkyl; and $R^{75}$ is H; lower alkyl; aryl; or —$NR^{70}R^{71}$, in which meanings of the variables $R^{55}$, $R^{57}$, $R^{58}$, $R^{59}$, $R^{60}$, $R^{61}$, $R^{62}$, $R^{68}$ and $R^{75}$ wherein each of the variables $R^{11}$, $R^{23}$, $R^{24}$, $R^{49}$, $R^{50}$, $R^{51}$, $R^{52}$, $R^{54}$, $R^{56}$, $R^{57}$, $R^{67}$ and o has a meaning as defined above;

$R^{64}$ is H; lower alkyl; lower alkenyl; —$(CH_2)_p(CHR^{78})_sOR^{77}$; or —$(CH_2)_p(CHR^{78})_sSR^{77}$;

$R^{70}$ is H; lower alkyl; aryl; or aryl-lower alkyl; and $R^{71}$ is H; lower alkyl; aryl; or aryl-lower alkyl; or $R^{70}$ and $R^{71}$, taken together, are —$(CH_2)_{2-7}$—; —$(CH_2)_2O(CH_2)_2$—; or —$(CH_2)_2NR^{57}(CH_2)_2$—, wherein in the variables $R^{64}$, $R^{70}$ and $R^{71}$, each of the variables $R^{57}$, p and s has a meaning as defined above;

$R^{77}$ is lower alkyl; or lower alkenyl; and $R^{78}$ is H; lower alkyl; lower alkenyl; —$(CH_2)_pOR^{77}$; or —$(CH_2)_pSR^{77}$, wherein in the variable $R^{78}$, each of the variables $R^{77}$ and p has a meaning as defined above, wherein in which formulae b1 and c1 $R^{11}$ is H; or lower alkyl,
in which formula b1
$R^{21}$ is
- H;
- lower alkyl;
- lower alkenyl;
- —$(CH_2)_pOR^{47}$ (where $R^{47}$: lower alkyl; or lower alkenyl);
- —$(CH_2)_pNR^{23}R^{24}$ (where $R^{23}$: lower alkyl; or lower alkenyl; $R^{24}$: H; or lower alkyl; or $R^{23}$ and $R^{24}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_pOCONR^{50}R^{67}$ (where $R^{50}$: H; or lower alkyl; or lower alkenyl; $R^{67}$: lower alkyl; or $R^{50}$ and $R^{67}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_pNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_pN(R^{11})COR^{56}$ (where: $R^{11}$: H; or lower alkyl; $R^{56}$: lower alkyl; or lower alkenyl);
- —$(CH_2)_oCOOR^{49}$ (where $R^{49}$: lower alkyl; or lower alkenyl);
- (—$CH_2)_oCONR^{50}R^{51}$ (where $R^{50}$: lower alkyl, or lower alkenyl; $R^{51}$: H; lower alkyl; or $R^{50}$ and $R^{51}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_oPO(OR^{52})_2$ (where $R^{52}$: lower alkyl; or lower alkenyl);
- —$(CH_2)_oSO_2R^{54}$ (where $R^{54}$: lower alkyl; or lower alkenyl); or
- —$(CH_2)_rC_6H_4R^3$ (where $R^3$: H; F; Cl; $CF_3$; $OCF_3$; $OCHF_2$; lower alkyl; lower alkenyl; or lower alkoxy), wherein in the variable $R^{21}$, each of the variables o, p and r has a meaning as defined above, and
$R^{22}$ is H or methyl
with the proviso that formula b1 excludes where $R^1$ is H, $R^{11}$ is H, $R^{17}$ is H, $R^{22}$ is H and $R^{21}$ is either H or —$(CH_2)_oCOOR^{49}$ wherein o is 1 and $R^{49}$ is a lower alkyl; and
in which formula c1
$R^{25}$ is
- H;
- lower alkyl;
- lower alkenyl;
- —$(CH_2)_mOR^{47}$ (where $R^{47}$: lower alkyl; or lower alkenyl);
- —$(CH_2)_mNR^{23}R^{24}$ (where $R^{23}$: lower alkyl; or lower alkenyl; $R^{24}$: H; or lower alkyl; or $R^{23}$ and $R^{24}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- $(CH_2)_mOCONR^{50}R^{67}$ (where $R^{50}$: H; or lower alkyl; or lower alkenyl; $R^{67}$: lower alkyl; or $R^{50}$ and $R^{67}$, taken together, are: —$(CH_2)_{2-6}$—$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_mNR^{11}CONR^{50}R^{51}$ (where $R^{11}$: H; or lower alkyl; $R^{50}$: H; or lower alkyl; or lower alkenyl; $R^{51}$: H; or lower alkyl; or $R^{50}$ and $R^{51}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_mN(R^{11})COR^{56}$ (where: $R^{11}$: H; or lower alkyl; $R^{56}$: lower alkyl; or lower alkenyl);
- —$(CH_2)_oCOOR^{49}$ (where $R^{49}$: lower alkyl; or lower alkenyl);
- —$(CH_2)_oCONR^{50}R^{51}$ (where $R^{50}$: lower alkyl; or lower alkenyl; $R^{51}$: H; lower alkyl; or $R^{50}$ and $R^{51}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl); or
- $(CH_2)_pC_6H_4R^3$ (where $R^3$: H; F; Cl; $CF_3$; $OCF_3$; $OCHF_2$; lower alkyl; lower alkenyl; or lower alkoxy);

$R^{26}$ is lower alkyl; lower alkenyl; aryl-lower alkyl; or$(CH_2)_pC_6H_4R^3$ (where $R^3$: H; F; Cl; $CF_3$; $OCF_3$; $OCHF_2$; lower alkyl; lower alkenyl; or lower alkoxy);
$R^{27}$ is
- H;
- lower alkyl;
- lower alkenyl;
- —$(CH_2)_pOR^{47}$ (where $R^{47}$: lower alkyl; or lower alkenyl);
- —$(CH_2)_pNR^{23}R^{24}$ (where $R^{23}$: lower alkyl; or lower alkenyl; $R^{24}$: H; or lower alkyl; or $R^{23}$ and $R^{24}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_pOCONR^{50}R^{67}$ (where $R^{50}$: H; lower alkyl; or lower alkenyl; $R^{67}$: lower alkyl; or $R^{50}$ and $R^{67}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_pNR^{11}CONR^{50}R^{51}$ (where $R^{11}$: H; or lower alkyl; $R^{50}$: H; lower alkyl; or lower alkenyl; $R^{51}$: H; or lower alkyl; or $R^{50}$ and $R^{51}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_pN(R^{11})COR^{56}$ (where: $R^{11}$: H; or lower alkyl; $R^{56}$: lower alkyl; or lower alkenyl);
- —$(CH_2)_oCOOR^{49}$ (where $R^{49}$: lower alkyl; or lower alkenyl);
- —$(CH_2)_oCONR^{50}R^{51}$ (where $R^{50}$: lower alkyl, or lower alkenyl; $R^{51}$: H; or lower alkyl; or $R^{50}$ and $R^{51}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);
- —$(CH_2)_oPO(OR^{52})_2$ (where $R^{52}$: lower alkyl; or lower alkenyl);
- —$(CH_2)_oSO_2R^{54}$ (where $R^{54}$: lower alkyl; or lower alkenyl); or
- —$(CH_2)_qC_6H_4R^3$ (where $R^3$: H; F; Cl; $CF_3$; $OCF_3$; $OCHF_2$; lower alkyl; lower alkenyl; or lower alkoxy); and $R^{28}$ is
- H;
- lower alkyl;
- lower alkenyl;
- —$(CH_2)_pOR^{47}$ (where $R^{47}$: lower alkyl; or lower alkenyl);
- —$(CH_2)_pNR^{23}R^{24}$ (where $R^{23}$: lower alkyl; or lower alkenyl; $R^{24}$: H; or lower alkyl; or $R^{23}$ and $R^{24}$, taken together, are: —$(CH_2)_{2-6}$—; —$(CH_2)_2O(CH_2)_2$—; —$(CH_2)_2S(CH_2)_2$—; or —$(CH_2)_2NR^{49}(CH_2)_2$—; where $R^{49}$: H; or lower alkyl);

—(CH$_2$)$_p$OCONR$^{50}$R$^{67}$ (where R$^{50}$: H; lower alkyl; or lower alkenyl; R$^{67}$: lower alkyl; or R$^{50}$ and R$^{67}$, taken together, are: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl);

—(CH$_2$)$_p$NR$^{11}$CONR$^{50}$R$^{51}$ (where R$^{11}$: H; or lower alkyl; R$^{50}$: H; lower alkyl; or lower alkenyl; R$^{51}$: H; or lower alkyl; or R$^{50}$ and R$^{51}$, taken together, are: —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl);

—(CH$_2$)$_p$N(R$^{11}$)COR$^{56}$ (where: R$^{11}$: H; or lower alkyl; R$^{56}$: lower alkyl; or lower alkenyl);

—(CH$_2$)$_o$COOR$^{49}$ (where R$^{49}$: lower alkyl; or lower alkenyl);

—(CH$_2$)$_o$CONR$^{50}$R$^{51}$ (where R$^{50}$: lower alkyl, or lower alkenyl; R$^{51}$: H; or lower alkyl; or R$^{50}$ and R$^{51}$, taken together, are —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; where R$^{49}$: H; or lower alkyl);

—(CH$_2$)$_o$PO(OR$^{52}$)$_2$ (where R$^{52}$: lower alkyl; or lower alkenyl);

—(CH$_2$)$_o$SO$_2$R$^{54}$ (where R$^{54}$: lower alkyl; or lower alkenyl); or

—(CH$_2$)$_q$C$_6$H$_4$R$^3$ (where R$^3$: H; F; Cl; CF$_3$; lower alkyl; lower alkenyl; or lower alkoxy), wherein in variables R$^{25}$, R$^{26}$, R$^{27}$ and R$^{28}$, each of the variables m, o, p and q has a meaning as defined above, with the provisor that formula c1 excludes where R$^{25}$ is a lower alkyl, R$^{26}$ is a lower alkyl, and R$^{27}$ is either H or a lower alkyl;

or (b) a dipeptide residue made up of two different amino acid building blocks, the dipeptide being selected from the group consisting of $^D$Pro$^L$Azt and $^D$Pro$^L$Tic, and Z is a tetrapeptide chain made up of four alpha-amino acid residues, in which
  the P1 residue is Gly or of type C, D, E or F;
  the P2 residue is Gly or of type C, D or E;
  the P3 residue is Gly or of type D or E; and
  the P4 residue is Gly or of type C, D, E or F,
  at positions P2 and P3 also D-isomers being possible,
  the residue of type C being —NR$^{11}$CH(R$^{64}$)CO—;
  the residue of type D being —NR$^{11}$CH(R$^{65}$)CO—;
  the residue of type E being —NR$^{11}$CH(R$^{66}$)CO—; and
  the residue of type F being —NR$^{11}$CH(R$^{76}$)CO—,
wherein in which residues of type C, D, E or F, each of the variables R$^{11}$ and R$^{64}$ has a meaning as defined above;

R$^{65}$ is —(CH$_2$)$_o$R$^{69}$; —(CH$_2$)$_r$O(CH$_2$)$_o$R$^{69}$; —(CH$_2$)$_r$S(CH$_2$)$_o$R$^{69}$; or —(CH$_2$)$_r$NR$^{11}$(CH$_2$)$_o$R$^{69}$;

R$^{66}$ is —(CH$_2$)$_p$NR$^{70}$R$^{71}$; —(CH$_2$)$_p$NR$^{69}$R$^{72}$; —(CH$_2$)$_p$C(=NR$^{72}$)NR$^{70}$R$^{71}$; —(CH$_2$)$_p$C(=NOR$^{42}$)NR$^{70}$R$^{71}$; —(CH$_2$)$_p$C(=NNR$^{40}$R$^{71}$)NR$^{70}$R$^{71}$; —(CH$_2$)$_p$NR$^{72}$C(=NR$^{72}$)NR$^{70}$R$^{71}$; —(CH$_2$)$_p$N=C(NR$^{70}$R$^{72}$)NR$^{71}$R$^{72}$; —(CH$_2$)$_p$C$_6$H$_4$NR$^{70}$R$^{71}$; —(CH$_2$)$_p$C$_6$H$_4$NR$^{69}$R$^{72}$; —(CH$_2$)$_p$C$_6$H$_4$C(=NR$^{72}$)NR$^{70}$R$^{71}$; —(CH$_2$)$_p$C$_6$H$_4$C(=NOR$^{42}$)NR$^{70}$R$^{71}$; —(CH$_2$)$_p$C$_6$H$_4$C(=NNR$^{70}$R$^{71}$)NR$^{70}$R$^{71}$; —(CH$_2$)$_p$C$_6$H$_4$NR$^{72}$C(=NR$^{72}$)NR$^{70}$R$^{71}$; —(CH$_2$)$_p$C$_6$H$_4$N=C(NR$^{70}$R$^{72}$)NR$^{71}$R$^{72}$; —(CH$_2$)$_r$O(CH$_2$)$_m$NR$^{70}$R$^{71}$; —(CH$_2$)$_r$O(CH$_2$)$_m$NR$^{69}$R$^{72}$; —(CH$_2$)$_r$O(CH$_2$)$_p$C(=NR$^{72}$)NR$^{70}$R$^{71}$; —(CH$_2$)$_r$O(CH$_2$)$_p$C(=NOR$^{72}$)NR$^{70}$R$^{71}$; —(CH$_2$)$_r$O(CH$_2$)$_m$NR$^{72}$C(=NR$^{72}$)NR$^{70}$R$^{71}$; —(CH$_2$)$_r$O(CH$_2$)$_m$N=C(NR$^{70}$R$^{72}$)NR$^{71}$R$^{72}$; —(CH$_2$)$_r$O(CH$_2$)$_p$C$_6$H$_4$CNR$^{70}$R$^{71}$; —(CH$_2$)$_r$O(CH$_2$)$_p$C$_6$H$_4$C(=NR$^{72}$)NR$^{70}$R$^{71}$; —(CH$_2$)$_r$O(CH$_2$)$_p$C$_6$H$_4$C(=NOR$^{42}$)NR$^{70}$R$^{71}$; —(CH$_2$)$_r$O(CH$_2$)$_p$C$_6$H$_4$C(=NNR$^{70}$R$^{71}$)NR$^{70}$R$^{71}$; —(CH$_2$)$_r$O(CH$_2$)$_p$C$_6$H$_4$NR$^{72}$C(=NR$^{72}$)NR$^{70}$R$^{71}$; —(CH$_2$)$_r$S(CH$_2$)$_m$NR$^{70}$R$^{71}$; —(CH$_2$)$_r$S(CH$_2$)$_m$NR$^{69}$R$^{72}$; —(CH$_2$)$_r$S(CH$_2$)$_p$C(=NR$^{72}$)NR$^{70}$R$^{71}$; —(CH$_2$)$_r$S(CH$_2$)$_p$C(=NOR$^{42}$)NR$^{70}$R$^{71}$; —(CH$_2$)$_r$S(CH$_2$)$_p$C(=NNR$^{70}$R$^{71}$)NR$^{70}$R$^{71}$; —(CH$_2$)$_r$S(CH$_2$)$_m$NR$^{72}$C(=NR$^{72}$)NR$^{70}$R$^{71}$; —(CH$_2$)$_r$S(CH$_2$)$_m$N=C(NR$^{70}$R$^{72}$)NR$^{71}$R$^{72}$; —(CH$_2$)$_r$S(CH$_2$)$_p$C$_6$H$_4$CNR$^{70}$R$^{71}$; —(CH$_2$)$_r$S(CH$_2$)$_p$C$_6$H$_4$C(=NR$^{72}$)NR$^{70}$R$^{71}$; —(CH$_2$)$_r$S(CH$_2$)$_p$C$_6$H$_4$C(=NOR$^{42}$)NR$^{70}$R$^{71}$; —(CH$_2$)$_r$S(CH$_2$)$_p$C$_6$H$_4$C(=NNR$^{70}$R$^{71}$)NR$^{70}$R$^{71}$; —(CH$_2$)$_r$S(CH$_2$)$_p$C$_6$H$_4$NR$^{72}$C(=NR$^{72}$)NR$^{70}$R$^{71}$; —(CH$_2$)$_p$NR$^{72}$COR$^{56}$; or —(CH$_2$)$_p$NR$^{72}$COR$^{69}$; and R$^{76}$ is —(CH$_2$)$_p$(CHR$^{79}$)$_s$OH; —(CH$_2$)$_p$(CHR$^{79}$)$_s$CONR$^{70}$R$^{71}$; —(CH$_2$)$_p$(CHR$^{79}$)$_s$COOR$^{49}$; —(CH$_2$)$_p$(CHR$^{79}$)$_s$NR$^{72}$CONR$^{70}$R$^{71}$; —(CH$_2$)$_p$(CHR$^{79}$)$_s$NR$^{11}$COR$^{56}$; —(CH$_2$)$_p$C$_6$H$_4$CONR$^{70}$R$^{71}$; or —(CH$_2$)$_p$C$_6$H$_4$NR$^{72}$CONR$^{70}$R$^{71}$, wherein in the variables R$^{66}$ and R$^{76}$, each of the variables R$^{11}$, R$^{49}$, R$^{56}$, R$^{69}$, R$^{70}$, R$^{71}$, m, o, p, r and s has a meaning as defined above;

R$^{42}$ is lower alkyl; lower alkenyl; or aryl-lower alkyl;

R$^{72}$ is H; or lower alkyl;

R$^{69}$ and R$^{72}$, taken together, are —(CH$_2$)$_{2\text{-}6}$—; —(CH$_2$)$_2$O(CH$_2$)$_2$—; —(CH$_2$)$_2$S(CH$_2$)$_2$—; or —(CH$_2$)$_2$NR$^{49}$(CH$_2$)$_2$—; and R$^{79}$ is H; lower alkyl; lower alkenyl; aryl; heteroaryl; aryl-lower alkyl; —(CH$_2$)$_p$OR$^{77}$; —(CH$_2$)$_p$OCONR$^{50}$R$^{67}$; —(CH$_2$)$_p$NR$^{11}$CONR$^{50}$R$^{67}$; —(CH$_2$)$_p$NR$^{11}$COR$^{56}$; —(CH$_2$)$_o$COOR$^{49}$; —(CH$_2$)$_o$CONR$^{50}$R$^{51}$; —(CH$_2$)$_o$PO(OR$^{52}$)$_2$; or —(CH$_2$)$_o$SO$_2$R$^{54}$, wherein in the variables R$^{69}$, R$^{72}$ and R$^{79}$, each of the variables R$^{11}$, R$^{49}$, R$^{50}$, R$^{51}$, R$^{52}$, R$^{54}$, R$^{56}$, R$^{67}$, R$^{77}$, o and p has a meaning as defined above, or (ii) in which

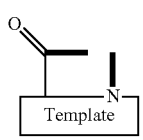

is a dipeptide residue made up of two different amino acid building blocks, the dipeptide being $^D$Pro$^L$Tic, and Z is a tetrapeptide chain made up of four alpha-amino acid residues, wherein
  the P1 residue is Ile;
  the P2 residue is $^D$Arg;
  the P3 residue is Aib; and
  the P4 residue is Ile, in each case in free form or in pharmaceutically acceptable salt form.

2. A compound according to claim 1 of the formula I, in which, in the tetrapeptide chain Z, the P1 residue is Phe, Ile, Gln, Thr, Trp, Glu or Tyr;
the P2 residue is Trp, Lys or $^D$Val;
the P3 residue is Lys, Tyr, Arg or Trp; and
the P4 residue is Tyr, His, Gly, Ala, Orn or Lys.

3. A compound according to claim 2 of the formula I, in which

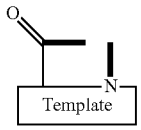

is a dipeptide residue made up of two different amino acid building blocks, the dipeptide being $^D$Pro$^L$Tic, and, in the tetrapeptide chain Z, the P1 residue is Ile;
the P2 residue is Trp;
the P3 residue is Lys; and
the P4 residue is Tyr.

4. A compound according to claim 2 of the formula I, in which

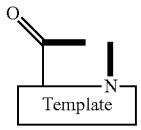

is a dipeptide residue made up of two different amino acid building blocks, the dipeptide being $^D$Pro$^L$Azt, and, in the tetrapeptide chain Z, the P1 residue is Tyr;
the P2 residue is Trp;
the P3 residue is Arg; and
the P4 residue is Gly.

5. A compound according to claim 1 of the formula I in the form of an enantiomer.

6. A medicament comprising a compound according to claim 1 of the formula I.

7. A selective G-protein-coupled receptor antagonist or agonist comprising the compound according to claim 1 of the formula I.

8. A pharmaceutical composition comprising the compound according to claim 1 of the formula I and a pharmaceutically acceptable carrier.

9. The composition according to claim 8 in a form suitable for oral, topical, transdermal, injection, buccal, transmucosal, pulmonary or inhalation administration.

10. A composition according to claim 8 in the form of a tablet, a dragee, a capsule, a solution, a liquid, a gel, a plaster, a cream, an ointment, a syrup, a slurry, a suspension, a spray, a nebuliser or a suppository.

11. A process for the preparation of a compound according to claim 1 of the formula I, which comprises
(a) coupling an appropriately functionalized solid support with a compound of the formula II,

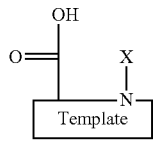

in which

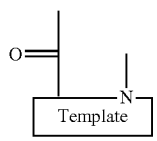

has one of the meanings defined in claim 1 and X is an N-protecting group;
(b) removing the N-protecting group from the product obtained in step (a);
(c) coupling the product thus obtained with an appropriately N-protected derivative of that amino acid, which in the desired end-product is in position 4, any functional group, which may be present in said N-protected amino acid derivative, being likewise appropriately protected;
(d) removing the N-protecting group from the product thus obtained;
(e) coupling the product thus obtained with an appropriately N-protected derivative of that amino acid, which in the desired end-product is one position farther away from position 4, any functional group, which may be present in said N-protected amino acid derivative, being likewise appropriately protected;
(f) removing the N-protecting group from the product thus obtained;
(g) repeating steps (e) and (f), until all amino acid residues have been introduced;
(h) if desired, selectively deprotecting one or several protected functional group(s) present in the molecule and appropriately substituting the reactive group(s) thus liberated;
(i) detaching the product thus obtained from the solid support;
(j) cyclizing the product cleaved from the solid support;
(k) removing any protecting groups present on functional groups of any amino acid residues in the cyclic product thus obtained and, if desired, any protecting group(s), which may in addition be present in the molecule thus obtained; and
(l) if desired, converting a compound of the formula I in free form thus obtained into a pharmaceutically acceptable salt, or converting a pharmaceutically acceptable, or unacceptable, salt thus obtained into the corresponding compound of the formula I in free form or into a different, pharmaceutically acceptable, salt.

12. The process according to claim 11, wherein said compound of the formula I is in the form of an enantiomer and wherein said process comprises a chiral starting material in the form of an enantiomer.

* * * * *